(12) United States Patent
Ramdas et al.

(10) Patent No.: US 9,073,943 B2
(45) Date of Patent: Jul. 7, 2015

(54) ANTIVIRAL COMPOUNDS WITH A DIBENZOOXAHETEROCYCLE MOIETY

(71) Applicant: Lupin Limited, Mumbai, Maharashtra (IN)

(72) Inventors: Vidya Ramdas, Pune (IN); Advait Arun Joshi, Pune (IN); Moloy Manoj Banerjee, Pune (IN); Amit Kumar Das, Pune (IN); Deepak Sahebrao Walke, Pune (IN); Venkata P. Palle, Pune (IN); Rajender Kumar Kamboj, Pune (IN)

(73) Assignee: Lupin Limited, Mumbai (IN)

( * ) Notice: Subject to any disclaimer, the term of this patent is extended or adjusted under 35 U.S.C. 154(b) by 0 days.

(21) Appl. No.: 14/375,534

(22) PCT Filed: Feb. 8, 2013

(86) PCT No.: PCT/IB2013/051062
§ 371 (c)(1),
(2) Date: Jul. 30, 2014

(87) PCT Pub. No.: WO2013/118097
PCT Pub. Date: Aug. 15, 2013

(65) Prior Publication Data
US 2015/0010505 A1 Jan. 8, 2015

(30) Foreign Application Priority Data

Feb. 10, 2012 (IN) .............................. 147/KOL/2012
Sep. 4, 2012 (IN) ............................ 1017/KOL/2012

(51) Int. Cl.
| C07D 405/14 | (2006.01) |
| A61K 31/4178 | (2006.01) |
| A61K 45/06 | (2006.01) |
| C07D 495/04 | (2006.01) |
| C07D 409/14 | (2006.01) |
| C07D 417/14 | (2006.01) |
| A61K 31/428 | (2006.01) |

(52) U.S. Cl.
CPC ............ *C07D 495/04* (2013.01); *C07D 409/14* (2013.01); *C07D 417/14* (2013.01); *A61K 31/4178* (2013.01); *A61K 45/06* (2013.01); *C07D 405/14* (2013.01); *A61K 31/428* (2013.01)

(58) Field of Classification Search
USPC ........................................ 514/397; 548/311.7
See application file for complete search history.

(56) References Cited

U.S. PATENT DOCUMENTS

| 4,235,871 A | 11/1980 | Papahadjopoulos et al. |
| 4,501,728 A | 2/1985 | Geho et al. |
| 4,837,028 A | 6/1989 | Allen |
| 5,019,369 A | 5/1991 | Presant et al. |
| 8,008,263 B2 | 8/2011 | Britt et al. |
| 8,008,264 B2 | 8/2011 | Butler et al. |
| 8,012,941 B2 | 9/2011 | Cho et al. |
| 8,012,942 B2 | 9/2011 | Butler et al. |
| 8,012,982 B2 | 9/2011 | Conte et al. |
| 8,093,243 B2 | 1/2012 | Bachand et al. |
| 8,101,643 B2 | 1/2012 | Qiu et al. |
| 8,133,884 B2 | 3/2012 | Martin et al. |
| 8,143,288 B2 | 3/2012 | Serrano-Wu et al. |
| 8,143,301 B2 | 3/2012 | Belema et al. |
| 8,143,414 B2 | 3/2012 | Lavoie et al. |
| 8,147,818 B2 | 4/2012 | Bachand et al. |
| 8,188,132 B2 | 5/2012 | Or et al. |
| 8,198,449 B2 | 6/2012 | Pracitto et al. |
| 2005/0113374 A1 | 5/2005 | Gobbi et al. |
| 2009/0202478 A1 | 8/2009 | Bachand et al. |
| 2009/0202483 A1 | 8/2009 | Bachand et al. |
| 2011/0217261 A1 | 9/2011 | Or et al. |

(Continued)

FOREIGN PATENT DOCUMENTS

| EP | 2121697 B1 | 8/2011 |
| EP | 2385048 A1 | 11/2011 |

(Continued)

OTHER PUBLICATIONS

International Search Report in corresponding International Application No. PCT/IB2013/051062, mailed Jun. 27, 2013.

(Continued)

*Primary Examiner* — Kristin Vajda
(74) *Attorney, Agent, or Firm* — Leydig, Voit & Mayer, Ltd.

(57) ABSTRACT

Disclosed are compounds of formula (I) for use as antiviral agents, particularly as anti-hepatitis virus C agents, wherein R-R 6 and q are as described herein. Also disclosed are pharmaceutical compositions and methods of treating or preventing viral infection in a host by the use of these compounds, either alone or in combination with other pharmaceutically active agents. Further disclosed are methods of preparing such compounds. (I).

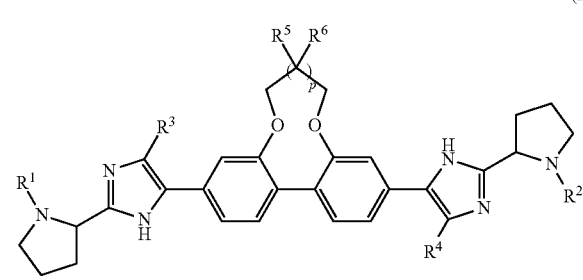

22 Claims, No Drawings

(56) References Cited

U.S. PATENT DOCUMENTS

| | | |
|---|---|---|
| 2011/0217265 A1 | 9/2011 | Glenn et al. |
| 2011/0223134 A1 | 9/2011 | Nair et al. |
| 2011/0236348 A1 | 9/2011 | Graupe et al. |
| 2011/0237579 A1 | 9/2011 | Li et al. |
| 2011/0237636 A1 | 9/2011 | Belema et al. |
| 2011/0250172 A1 | 10/2011 | Qiu et al. |
| 2011/0250176 A1 | 10/2011 | Lemm et al. |
| 2011/0269956 A1 | 11/2011 | Pack et al. |
| 2011/0274648 A1 | 11/2011 | Lavoie et al. |
| 2011/0281910 A1 | 11/2011 | Lavoie et al. |
| 2011/0286961 A1 | 11/2011 | Belema et al. |
| 2011/0293563 A1 | 12/2011 | Butler et al. |
| 2011/0294819 A1 | 12/2011 | Lopez et al. |
| 2011/0300104 A1 | 12/2011 | Qiu et al. |
| 2012/0004196 A1 | 1/2012 | DeGoey et al. |
| 2012/0028978 A1 | 2/2012 | Zhong et al. |
| 2012/0040962 A1 | 2/2012 | Li et al. |
| 2012/0040977 A1 | 2/2012 | Li et al. |
| 2012/0076755 A1 | 3/2012 | Qiu et al. |
| 2012/0083483 A1 | 4/2012 | Coburn et al. |

FOREIGN PATENT DOCUMENTS

| | | |
|---|---|---|
| EP | 2049116 B1 | 2/2012 |
| EP | 2086995 B1 | 2/2012 |
| EP | 2146984 B1 | 5/2012 |
| WO | WO 2004/014852 A2 | 2/2004 |
| WO | WO 2005/030694 A1 | 4/2005 |
| WO | WO 2006/079833 A1 | 8/2006 |
| WO | WO 2006/133326 A1 | 12/2006 |
| WO | WO 2007/031791 A1 | 3/2007 |
| WO | WO 2007/070556 A1 | 6/2007 |
| WO | WO 2007/070600 A2 | 6/2007 |
| WO | WO 2007/082554 A1 | 7/2007 |
| WO | WO 2008/021927 A2 | 2/2008 |
| WO | WO 2008/021928 A2 | 2/2008 |
| WO | WO 2008/021936 A2 | 2/2008 |
| WO | WO 2008/048589 A2 | 4/2008 |
| WO | WO 2008/064218 A2 | 5/2008 |
| WO | WO 2008/070447 A2 | 6/2008 |
| WO | WO 2008/144380 A1 | 11/2008 |
| WO | WO 2008/154601 A1 | 12/2008 |
| WO | WO 2009/020825 A1 | 2/2009 |
| WO | WO 2009/020828 A1 | 2/2009 |
| WO | WO 2009/034390 A1 | 3/2009 |
| WO | WO 2009/102318 A1 | 8/2009 |
| WO | WO 2009/102325 A1 | 8/2009 |
| WO | WO 2009/102568 A1 | 8/2009 |
| WO | WO 2009/102694 A1 | 8/2009 |
| WO | WO 2010/096462 A1 | 8/2010 |
| WO | WO 2010/111673 A1 | 9/2010 |
| WO | WO 2010/132601 A1 | 11/2010 |
| WO | WO 2010/148006 A1 | 12/2010 |
| WO | WO 2011/015657 A1 | 2/2011 |
| WO | WO 2011/031904 A1 | 3/2011 |
| WO | WO 2011/031934 A1 | 3/2011 |
| WO | WO 2011/079327 A1 | 6/2011 |
| WO | WO 2011/081918 A1 | 7/2011 |
| WO | WO 2011/087740 A1 | 7/2011 |
| WO | WO 2011/106929 A1 | 9/2011 |
| WO | WO 2011/106992 A1 | 9/2011 |
| WO | WO 2011/151651 A1 | 12/2011 |
| WO | WO 2011/151652 A1 | 12/2011 |
| WO | WO 2011/153396 A1 | 12/2011 |
| WO | WO 2011/156543 A2 | 12/2011 |
| WO | WO 2012/018325 A1 | 2/2012 |
| WO | WO 2012/018534 A2 | 2/2012 |
| WO | WO 2012/021591 A1 | 2/2012 |
| WO | WO 2012/021704 A1 | 2/2012 |
| WO | WO 2012/024363 A2 | 2/2012 |
| WO | WO 2012/039717 A1 | 3/2012 |
| WO | WO 2012/041014 A1 | 4/2012 |
| WO | WO 2012/041227 A1 | 4/2012 |
| WO | WO 2012/068234 A2 | 5/2012 |
| WO | WO 2013/118102 A1 | 8/2013 |

OTHER PUBLICATIONS

Avis, Kenneth E., "Parenteral Preparations," *Remington's Pharmaceutical Sciences*, 17$^{th}$ Edition, Chapter 85, Mack Publishing Company, Easton, PA, pp. 1518-1541 (1985).

Barnes, E., "Hepatitis C," World Health Organization Fact Sheet No. 164, http://www.who.int/mediacentre/factsheets/fs164/en/ (Apr. 2014).

Deluca, Patrick P., et al., "Parenteral Drug-Delivery Systems," *Pharmaceutics and Pharmacy Practice*, Chapter 8, J.B. Lippincott Company, Philadelphia, PA, pp. 238-250 (1982).

Fried, Michael W., et al., "Peginterferon Alfa-2a Plus Ribavirin for Chronic Hepatitis C Virus Infection," *The New England Journal of Medicine*, vol. 347, No. 13, pp. 975-982 (Sep. 26, 2002).

Hoofnagle, Jay H., "Hepatitis C: The Clinical Spectrum of Disease," *Hepatology*, vol. 26, No. 3, suppl. 1, pp. 15S-20S (Sep. 1997).

Jesudian, Arun B., et al., "Advances in the Treatment of Hepatitis C Virus Infection," *Gastroenterology & Hepatology*, vol. 8, No. 2, pp. 91-101 (Feb. 2012).

"Product Identification Guide," *Physicians' Desk Reference*, 58$^{th}$ Edition, Thomson PDR, Montvale, NJ, pp. 303-340 (2004).

"Product Information—Eisai," *Physicians' Desk Reference*, 58$^{th}$ Edition, Thomson PDR, Montvale, NJ, pp. 1221-1223 (2004).

"Product Information—Janssen," *Physicians' Desk Reference*, 58$^{th}$ Edition, Thomson PDR, Montvale, NJ, pp. 1759-1764 (2004).

"Product Information—Novartis Pharmaceuticals," *Physicians' Desk Reference*, 58$^{th}$ Edition, Thomson PDR, Montvale, NJ, pp. 2252-2259 (2004).

"Product Information—Pfizer," *Physicians' Desk Reference*, 58$^{th}$ Edition, Thomson PDR, Montvale, NJ, pp. 2570-2573 (2004).

Remingtons' Pharmaceutical Sciences, 18$^{th}$ Edition, p. 1445 (1990).

Shi, Junxing, et al., "Synthesis and biological evaluation of new potent and selective HCV NS5A inhibitors," *Bioorganic & Medicinal Chemistry Letters*, vol. 22, pp. 3488-3491 (2012).

Stahl, P. Heinrich, et al., *Handbook of Pharmaceutical Salts: Properties, Selection, and Use*, Wiley-VCH, Weinheim, pp. 1-374 (2002).

Szabó, Erzsébet, et al., "Viral Hepatitis: New Data on Hepatitis C Infection," *Pathology Oncology Research*, vol. 9, No. 4, pp. 215-221 (2003).

Szoka, Jr., Francis, et al., "Comparative Properties and Methods of Preparation of Lipid Vesicles (Liposomes)," *Annual Review of Biophysics & Bioengineering*, vol. 9, pp. 467-508 (1980).

Tusco, Salvatore J., et al., "Intravenous Admixtures," *Remington's Pharmaceutical Sciences*, 17$^{th}$ Edition, Chapter 86, Mack Publishing Company, Easton, PA, pp. 1542-1552 (1985).

Trissel, Lawrence A., "Intravenous Infusion Solutions," *ASHP Handbok on Injectable Drugs*, Fourth Edition, American Society of Hospital Pharmacists, Inc., Bethesda, MD, pp. 622-630 (1986).

Wasserman, Todd H., et al., "Clinical Comparison of the Nitrosoureas," *Cancer*, vol. 36, pp. 1258-1268 (1975).

ANTIVIRAL COMPOUNDS WITH A DIBENZOOXAHETEROCYCLE MOIETY

FIELD OF THE INVENTION

The present invention relates to antiviral compounds, their tautomeric forms, their stereoisomers, and their pharmaceutically acceptable salts, pharmaceutical compositions comprising one or more such compounds, and methods of treating viral infection.

CROSS-REFERENCE TO RELATED APPLICATION APPLICATIONS

This application is the U.S. National Phase of International Patent Application No. PCT/IB2013/051062, filed Feb. 8, 2013, which claims the benefit of Indian Provisional Patent Application Nos. 0147/KOL/2012, filed 10 Feb. 2012, and 1017/KOL/2012, filed 4 Sep. 2012, the disclosures of which are incorporated herein by reference in their entireties.

BACKGROUND OF THE INVENTION

Persistent hepatitis C virus (HCV) infection is a major health problem globally affecting ~3% of the world population and is an important contributor to chronic liver disease culminating with liver cirrhosis, hepatocellular carcinoma and liver failure [Szabo E, Lotz G, et al., *Pathol. Oncol. Res.* 2003, 9, 215-221; Hoofnagle J H., *Hepatology* 1997, 26 15S-20]. An estimated 170 million chronic carriers worldwide are at risk of developing liver disease. In the United States alone ~3 million are chronically infected with HCV and the number of HCV related deaths is increasing significantly over the years [Barnes E., WHO factsheet 2010. Available at: http://www.who.int/vaccine_research diseases/viral_cancers/en/index2.html].

Clinically, chronic infection is often asymptomatic with latent periods lasting for decades before manifestation by which time extensive liver damage has occurred. HCV is spread primarily by unscreened blood transfusions and use of contaminated needles and syringes; the highest risk groups are intravenous drug users and people who received blood transfusions (mainly haemophiliacs) before 1990 when screening for HCV was introduced. Factors that have been reported to influence the rate of HCV disease progression include age (increasing age is associated with more rapid progression), gender (males have more rapid disease progression than females), alcohol consumption (associated with an increased rate of disease progression), HIV co-infection (associated with a markedly increased rate of disease progression), and fatty liver.

The standard therapy for HCV was a combination of pegylated interferon (PEG-IFN) α and weight based ribavarin (RBV), which was inadequate for majority of the patients and therapy associated side effects such as pancytopenia, flu-like symptoms or depression were commonly observed leading to early treatment discontinuation [Fried M W, et al., *N. Engl. J. Med.,* 2002, 347, 975-982]. The approval of two direct acting agents (DAA) i.e. 1st generation protease inhibitors, Incivek and Victrelis in May 2011 ushered in the era of specifically targeted HCV therapy [Jesudian A B, Gambarin-Gelwan M and Jacobson I M., *Gastroenterology Hepatol.,* 2012, 8, 91-101].

The combination of above mentioned DAAs, PEG-IFN and RBV (triple therapy) substantially increased the rate of sustained virologic response in the treatment naive and experienced patients. However, a number of issues restrict the usage of these drugs—i) complex treatment algorithms issued by the regulatory bodies; ii) they are restricted to genotype 1; iii) low barrier to resistance mutations and/or iv) increased cost of therapy leading to only limited access to care. Hence, there exists a need for alternative therapeutic strategies that provide a broader genotype coverage, better efficacy, better tolerance and/or limited selection of resistant HCV variants.

The sequence diversity of HCV is complex with the virus organized into 6 distinct genotypes and over 100 subtypes. Additionally, HCV exists as many closely related viral sequences, termed as quasi-species, in the infected individual, making specific pharmaceutical targeting of HCV proteins challenging due to the rapid evolution of escape mutants. It is increasingly evident that a broad collection of specific, pan genotypic anti-viral drugs targeting multiple essential viral functions, in addition to the current viral therapies will be required for effective global control of HCV.

Disclosures describing HCV inhibitors include US 2009/0202478, US 2009/0202483, WO 2009/020828, WO 2009/020825, WO 2009/102318, WO 2009/102325, WO 2009/102694, WO 2008/144380, WO 2008/021927, WO 2008/021928, WO 2008/021936, WO 2006/133326, WO 2004/014852, WO 2008/070447, WO 2009/034390, WO 2006/079833, WO 2007/031791, WO 2007/070556, WO 2007/070600, WO 2008/064218, WO 2008/154601, WO 2007/082554, WO 2008/048589, EP 2121697, U.S. Pat. Nos. 8,008,264, 8,008,263, US 2011/0217265, US 2011/0217261, U.S. Pat. Nos. 8,012,982, 8,012,942, 8,012,941, US 2011/0223134, WO 2011/106992, WO 2011/106929, US 2011/0237636, US 2011/0237579, US 2011/0236348, US 2011/0250176, US 2011/0250172, US 2011/269956, US 2011/274648, EP 2385048, US 2011/0281910, US 2011/0286961, US 2011/0294819, US 2011/0293563, US 2011/300104, WO 2011/156543, WO 2011/153396, WO 2011/151652, WO 2011/151651, US 2012/004196, U.S. Pat. Nos. 8,093,243, 8,101,643, US 2012/0028978, WO 2012/018534, WO 2012/018325, WO 2012/021704, WO 2012/021591, US 2012/0040977, US 2012/0040962, WO 2012/024363, EP 2086995, EP 2049116, U.S. Pat. No. 8,133,884, US 2012/0076755, EP 2250163, U.S. Pat. Nos. 8,143,414, 8,143,301, 8,143,288, US 2012/0083483, U.S. Pat. No. 8,147,818, WO 2012/039717, WO 2012/041227, WO 2012/041014, EP 2146984, U.S. Pat. Nos. 8,188,132, and 8,198,449, the disclosure of which are incorporated by reference.

BRIEF SUMMARY OF THE INVENTION

The present invention provides antiviral compounds of the general formula (I):

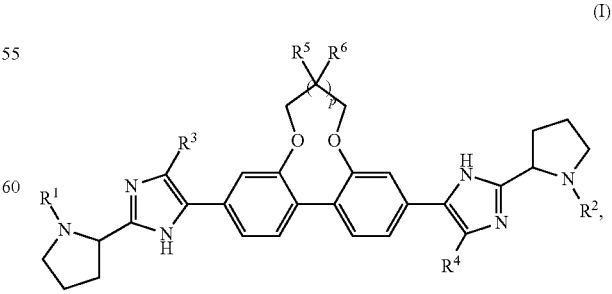

their tautomeric forms, their stereoisomers, their pharmaceutically acceptable salts, pharmaceutical composition containing them, methods of making the above compounds, and their use as antiviral compounds; wherein $R^1$-$R^6$ and p are described in detail below.

According to one aspect of the present invention there is provided compounds represented by the general formula I, its tautomeric forms, its stereoisomers, its pharmaceutically acceptable salts, their combinations with suitable medicament and pharmaceutical compositions containing them having a broader spectrum of activity as they show inhibitory actions against multiple genotypes of HCV with high potency.

The present invention also provide compounds represented by the general formula I, its tautomeric forms, its stereoisomers, its pharmaceutically acceptable salts, their combinations with suitable medicament and pharmaceutical compositions containing them having good stability in human liver microsomes and promising oral bioavailability with enhanced liver concentrations and high liver to plasma ratio.

DETAILED DESCRIPTION OF THE INVENTION

The present invention provides compounds of the general formula (I):

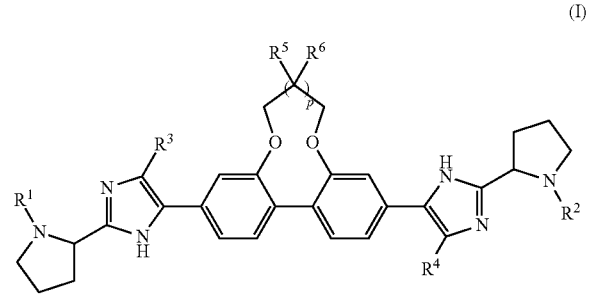

their tautomeric forms, their isomers, their pharmaceutically acceptable salts, pharmaceutical composition containing them, methods of making of the above compounds, and their use as antiviral compounds;
wherein,
$R^1$ and $R^2$ are each independently selected from hydrogen, substituted- or unsubstituted-alkyl, substituted- or unsubstituted-cycloalkyl, substituted- or unsubstituted-aryl, substituted- or unsubstituted-heteroaryl, substituted- or unsubstituted-heterocyclyl, $R^{7a}C(=O)$—, $R^{7a}S(=O)_2$—, $R^{7a}OC(=O)$—, $(R^8)R^7NC(=O)$—, $R^{7a}OC(=O)N(R^8)CR^b(R^a)C(=O)$—, $R^{7a}OC(=O)N(R^8)CR^b(R^aC(R^d)(R^c)C(=O)$—, $R^{7a}C(=O)N(R^8)C(R^b)(R^a)C(=O)$—, $R^{7a}C(=O)N(R^8)CR^b(R^a)C(R^d)(R^c)C(=O)$—, $(R^8)R^{7a}NC(=O)N(R^9)C(R^b)(R^a)C(=O)$—, and $R^8(R^7)NC(=O)N(R^9)CR^b(R^a)C(R^d)(R^cC(=O)$—;

$R^3$ and $R^4$ are each independently selected from hydrogen, halogen, substituted- or unsubstituted- alkyl, and substituted- or unsubstituted-cycloalkyl;
$R^5$ and $R^6$ are independently selected form hydrogen, substituted- or unsubstituted- alkyl; or
$R^5$ and $R^6$ are groups, which together with the carbon atom to which they are attached form a substituted- or unsubstituted-3 to 6 membered carbocycle or a substituted- or unsubstituted-5 to 6 membered heterocycle; or $R^5$ and $R^6$ are groups, wherein two $R^5$ groups attached to two different carbon atoms, two $R^6$ groups attached to two different carbon atoms, or an $R^5$ group attached to one carbon atom and an $R^6$ group attached to a different carbon atom, together with the carbon atoms to which they are attached form a substituted- or unsubstituted-3 to 6 membered carbocycle or a substituted- or unsubstituted-5 to 6 membered heterocycle;
$R^7$ is selected from hydrogen, substituted- or unsubstituted-alkyl, substituted- or unsubstituted-cycloalkyl, substituted- or unsubstituted-aryl, substituted- or unsubstituted-heteroaryl, and substituted- or unsubstituted-heterocyclyl;
$R^8$ and $R^9$ are each independently selected from hydrogen and substituted- or unsubstituted- alkyl;
$R^{7a}$ is independently selected from substituted- or unsubstituted- alkyl, substituted- or unsubstituted-cycloalkyl, substituted- or unsubstituted- aryl, substituted- or unsubstituted-heteroaryl, and substituted- or unsubstituted-heterocyclyl;
$R^a$, $R^b$, $R^c$ and $R^d$ are independently selected from hydrogen, substituted- or unsubstituted-$C_{1-6}$ alkyl, substituted- or unsubstituted- aryl, substituted- or unsubstituted-heteroaryl, substituted- or unsubstituted-cycloalkyl, and substituted- or unsubstituted-heterocyclyl, or $R^a$, $R^b$, $R^c$ and $R^d$ together with the carbon atom(s) to which they are attached forming substituted- or unsubstituted-carbocycle, substituted- or unsubstituted-heterocycle;
p is an integer selected from 1, 2, and 3;
when the alkyl group is a substituted alkyl group, the alkyl group is substituted with 1 to 4 substituents selected independently from oxo, halogen, cyano, perhaloalkyl, cycloalkyl, aryl, heteroaryl, heterocyclyl, $R^{10a}O$—, (alkyl)$S(=O)_2$—, (alkyl)$C(=O)$—, (alkyl)$OC(=O)$—, (alkyl)$C(=O)O$—, $R^{10}N(H)C(=O)$—, $R^{10}$(alkyl)NC(=O)—, (alkyl)$C(=O)N(H)$—, $R^{10}N(H)$—, $R^{10}$(alkyl)N—, $R^{10}(H)NC(=O)N(H)$—, and $R^{10}$(alkyl)NC(=O)N(H)—;
when the 'cycloalkyl' and the carbocyclic groups are substituted, each of them is substituted with 1 to 3 substituents selected independently from oxo, halogen, cyano, $C_{1-6}$ alkyl, perhaloalkyl, $R^{10a}O$—, (alkyl)$S(=O)_2$—, (alkyl)$C(=O)$—, (alkyl) $OC(=O)$—, (alkyl)$C(=O)O$—, $R^{10}(H)NC(=O)$—, $R^{10}$(alkyl)NC(=O)—, (alkyl)$C(=O)N(H)$—, $R^{10}(H)N$—, $R^{10}$(alkyl)N—, $R^{10}(H)NC(=O)N(H)$—, and $R^{10}$(alkyl)NC(=O)N(H)—;
when the aryl group is substituted, it is substituted with 1 to 3 substituents selected independently from halogen, cyano, hydroxy, $C_{1-6}$ alkyl, perhaloalkyl, alkyl-O—, perhaloalkyl-O—, alkyl(alkyl)N—, alkyl(H)N—, $H_2N$—, alkyl-$S(=O)_2$—, alkyl-$C(=O)$(alkyl)N—, alkyl-$C(=O)N(H)$—, alkyl(alkyl)NC(=O)—, alkyl(H)NC(=O)—, $H_2NC(=O)$—, alkyl(alkyl)NS(=O)_2—, alkyl(H)NS$(=O)_2$—, and $H_2NS(=O)_2$—;
when the heteroaryl group is substituted, it is substituted with 1 to 3 substituents selected independently from halogen, cyano, hydroxy, $C_{1-6}$ alkyl, perhaloalkyl, alkyl-O—, perhaloalkyl-O—, alkyl(alkyl)N—, alkyl(H)N—, $H_2N$—, alkyl-$S(=O)_2$—, alkyl-$C(=O)$(alkyl)N—, alkyl-$C(=O)N(H)$—, alkyl(alkyl)NC(=O)—, alkyl(H)NC(=O)—, $H_2NC(=O)$—, alkyl(alkyl)NS(=O)_2—, alkyl(H)NS$(=O)_2$—, and $H_2NS(=O)_2$—;
when the heterocyclic group is substituted, it can be substituted either on a ring carbon atom or on a ring heteroatom, when it substituted on a ring carbon atom, it is substituted with 1-3 substituents selected independently from halogen, cyano, oxo, $C_{1-6}$ alkyl, perhaloalkyl, $R^{10a}O$—, (alkyl)OC$(=O)$—, (alkyl)$C(=O)O$—, $R^{10}(H)NC(=O)$—, $R^{10}$(alkyl)NC(=O)—, (alkyl)$C(=O)N(H)$—, $R^{10}(H)N$—, $R^{10}$(alkyl)N—, $R^{10}(H)NC(=O)N(H)$—, and $R^{10}$(alkyl) NC(=O)N(H)—;
when the 'heterocyclic' group is substituted on a ring nitrogen(s), it is substituted with a substituent selected from $C_{1-6}$ alkyl, (alkyl)SO$_2$—, (alkyl)C(=O)—, (alkyl)OC(=O)—, R$^{10}$(H)NC(=O)—, and R$^{10}$(alkyl)NC(=O)—;

R$^{10}$ is selected from hydrogen, alkyl, cycloalkyl, aryl, heteroaryl, and heterocyclyl; and R$^{10a}$ is selected from hydrogen, alkyl, perhaloalkyl, cycloalkyl, aryl, heteroaryl, and heterocyclyl.

R$^1$ and R$^2$ are each independently selected from R$^{7a}$C(=O)—, R$^{7a}$S(=O)$_2$—, R$^{7a}$OC(=O)—, (R$^8$)R$^7$NC(=O)—, R$^{7a}$OC(=O)N(R$^8$)CR$^b$(R$^a$)C(=O)—, R$^{7a}$OC(=O)N(R$^8$)CR$^b$(R$^a$)C(R$^d$)(R$^c$)C(=O)—, R$^{7a}$C(=O)N(R$^8$)C(R$^b$)(R$^a$)C(=O)—, R$^{7a}$C(=O)N(R$^8$)CR$^b$(R$^a$)C(R$^d$)(R$^c$)C(=O)—, (R$^8$)R$^7$NC(=O)N(R$^9$)C(R$^b$)(R$^a$)C(=O)—, and R$^8$(R$^7$)NC(=O)N(R$^9$)CR$^b$(R$^a$)C(R$^d$)(R$^c$)C(=O)—;

R$^1$ and R$^2$ are each independently selected from R$^{7a}$OC(=O)N(R$^8$)CR$^b$(R$^a$)C(=O)—, R$^{7a}$OC(=O)N(R$^8$)CR$^b$(R$^a$)C(R$^d$)(R$^c$)C(=O)—, R$^{7a}$C(=O)N(R$^8$)C(R$^b$)(R$^a$)C(=O)—, R$^{7a}$C(=O)N(R$^8$)CR$^b$(R$^a$)C(R$^d$)(R$^c$)C(=O)—, (R$^8$)R$^7$NC(=O)N(R$^9$)C(R$^b$)(R$^a$)C(=O)—, and R$^8$(R$^7$)NC(=O)N(R$^9$)CR$^b$(R$^a$)C(R$^d$)(R$^c$)C(=O)—;

R$^1$ and R$^2$ both are particularly selected as R$^{7a}$OC(=O)N(R$^8$)CR$^b$(R$^a$)C(=O)—.

R$^3$ and R$^4$ are each selected from hydrogen, halo, alkyl, and cycloalkyl.

R$^3$ and R$^4$ are each particularly selected from hydrogen, chloro, ethyl, and cyclopropyl;

Whenever a range of the number of atoms in a structure is indicated (e.g., a C$_{1-12}$, C$_{1-8}$, C$_{1-6}$, or C$_{1-4}$ alkyl, alkylamino, etc.), it is specifically contemplated that any sub-range or individual number of carbon atoms falling within the indicated range also can be used. Thus, for instance, the recitation of a range of 1-8 carbon atoms (e.g., C$_1$-C$_8$), 1-6 carbon atoms (e.g., C$_1$-C$_6$), 1-4 carbon atoms (e.g., C$_1$-C$_4$), 1-3 carbon atoms (e.g., C$_1$-C$_3$), or 2-8 carbon atoms (e.g., C$_2$-C$_8$) as used with respect to any chemical group (e.g., alkyl, alkylamino, etc.) referenced herein encompasses and specifically describes 1, 2, 3, 4, 5, 6, 7, 8, 9, 10, 11, and/or 12 carbon atoms, as appropriate, as well as any sub-range thereof (e.g., 1-2 carbon atoms, 1-3 carbon atoms, 1-4 carbon atoms, 1-5 carbon atoms, 1-6 carbon atoms, 1-7 carbon atoms, 1-8 carbon atoms, 1-9 carbon atoms, 1-10 carbon atoms, 1-11 carbon atoms, 1-12 carbon atoms, 2-3 carbon atoms, 2-4 carbon atoms, 2-5 carbon atoms, 2-6 carbon atoms, 2-7 carbon atoms, 2-8 carbon atoms, 2-9 carbon atoms, 2-10 carbon atoms, 2-11 carbon atoms, 2-12 carbon atoms, 3-4 carbon atoms, 3-5 carbon atoms, 3-6 carbon atoms, 3-7 carbon atoms, 3-8 carbon atoms, 3-9 carbon atoms, 3-10 carbon atoms, 3-11 carbon atoms, 3-12 carbon atoms, 4-5 carbon atoms, 4-6 carbon atoms, 4-7 carbon atoms, 4-8 carbon atoms, 4-9 carbon atoms, 4-10 carbon atoms, 4-11 carbon atoms, and/or 4-12 carbon atoms, etc., as appropriate).

One of the embodiments of the present invention is a compound of formula (Ia):

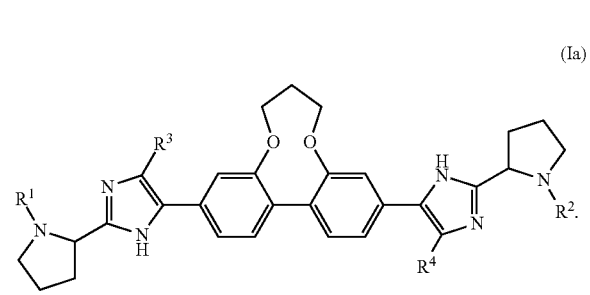

(Ia)

Another embodiment of the present invention is a compound of formula (Ib):

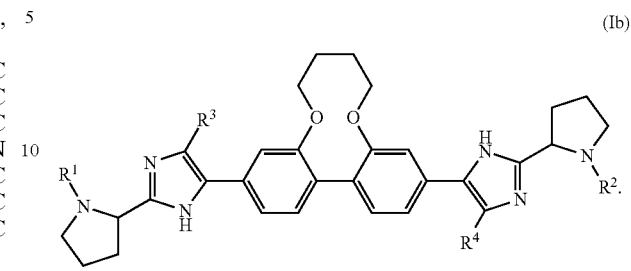

(Ib)

Yet another embodiment of the present invention is a compound of formula (Ic):

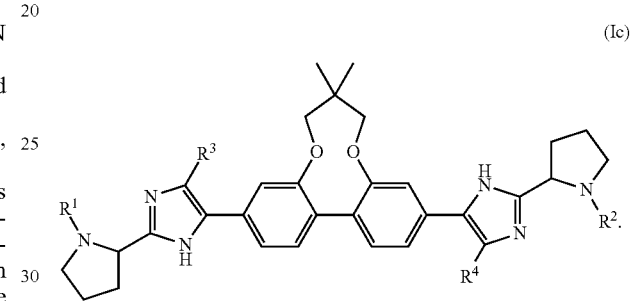

(Ic)

Further embodiment of the present invention is a compound of formula (Id):

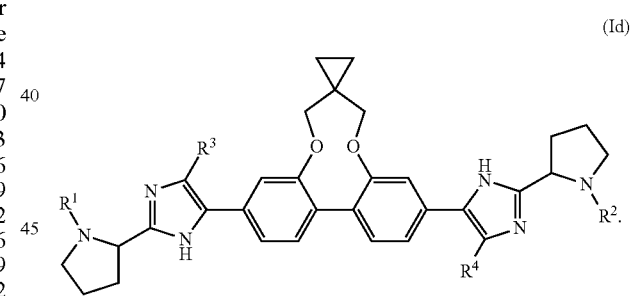

(Id)

Yet another embodiment of the present invention is a compound of formula (Ie):

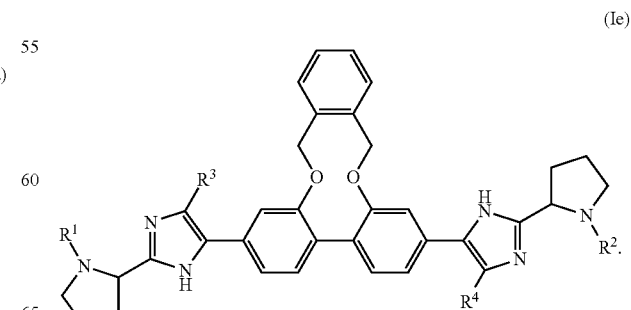

(Ie)

In any of the embodiments described above, $R^1$ and $R^2$ both are particularly selected as $R^{7a}OC(=O)N(R^8)CR^b(R^a)C(=O)—$.

General terms used in the description of the formula above can be defined as follows; however, the meaning stated should not be interpreted as limiting the scope of the term per se.

The term "alkyl", as used herein, means a straight or branched hydrocarbyl chain containing from 1 to 20 carbon atoms. Preferably, the alkyl group contains 1 to 10 carbon atoms. More preferably, alkyl group contains up to 6 carbon atoms. Examples of alkyl groups include, but are not limited to, methyl, ethyl, n-propyl, iso-propyl, n-butyl, sec-butyl, iso-butyl, tert-butyl, n-pentyl, isopentyl, neopentyl, and n-hexyl.

In a substituted alkyl group, the alkyl group is substituted with 1 to 4 substituents selected independently from oxo, halogen, cyano, perhaloalkyl, cycloalkyl, aryl, heteroaryl, heterocyclyl, $R^{11a}O—$, (alkyl)S(=O)$_2$—, (alkyl)C(=O)—, (alkyl) OC(=O)—, (alkyl) C(=O)O—, $R^{11}N(H)C(=O)—$, $R^{11}$(alkyl)NC(=O)—, (alkyl)C(=O)N(H)—, $R^{11}N(H)—$, $R^{11}$(alkyl)N—, $R^{11}(H)NC(=O)N(H)—$, and $R^{11}$(alkyl)NC(=O)N(H)—; wherein, $R^{11}$ is selected from hydrogen, alkyl, cycloalkyl, aryl, heteroaryl, and heterocyclyl; and $R^{11a}$ is selected from hydrogen, alkyl, perhaloalkyl, cycloalkyl, aryl, heteroaryl, and heterocyclyl.

The term "cycloalkyl" as used herein, means a monocyclic, bicyclic, or tricyclic non-aromatic ring system containing from 3 to 14 carbon atoms, preferably monocyclic cycloalkyl ring containing 3 to 6 carbon atoms. Examples of monocyclic ring systems include cyclopropyl, cyclobutyl, cyclopentyl, cyclohexyl, cycloheptyl, and cyclooctyl. Bicyclic ring systems include monocyclic ring system fused across a bond with another cyclic system which may be an alicyclic ring or an aromatic ring. Bicyclic rings also include spirocyclic systems wherein the second ring gets annulated on a single carbon atom. Bicyclic ring systems are also exemplified by a bridged monocyclic ring system in which two non-adjacent carbon atoms of the monocyclic ring are linked by an alkylene bridge. Examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1] nonane, and bicyclo[4.2.1]nonane, bicyclo[3.3.2]decane, bicyclo[3.1.0]hexane, bicyclo[410]heptane, bicyclo[3.2.0] heptanes, octahydro-1H-indene, spiro[2.5]octane, spiro[4.5] decane, spiro[bicyclo[4.1.0]heptane-2,1'-cyclopentane], hexahydro-2'H-spiro[cyclopropane-1,1'-pentalene]. Tricyclic ring systems are the systems wherein the bicyclic systems as described about are further annulated with third ring, which may be alicyclic ring or aromatic ring. Tricyclic ring systems are also exemplified by a bicyclic ring system in which two non-adjacent carbon atoms of the bicyclic ring are linked by a bond or an alkylene bridge. Examples of tricyclic-ring systems include, but are not limited to, tricyclo [3.3.1.0$^{3.7}$]nonane and tricyclo[3.3.1.1$^{3.7}$]decane (adamantane).

The term "carbocycle" as used herein, means a cyclic system made up of carbon atoms, which includes cycloalkyl, cycloalkenyl and aryl.

When the cycloalkyl or the carbocyclic groups are substituted, they are substituted with 1 to 3 substituents selected independently from oxo, halogen, cyano, $C_{1-6}$ alkyl, perhaloalkyl, $R^{11a}O—$, (alkyl)S(=O)$_2$—, (alkyl)C(=O)—, (alkyl)OC(=O)—, (alkyl)C(=O)O—, $R^{11}H(N)C(=O)—$, $R^{11}$(alkyl)NC(=O)—, (alkyl)C(=O)N(H)—, $R^{11}(H)N—$, $R^{11}$(alkyl)N—, $R^{11}(H)NC(=O)N(H)—$, and $R^{11}$(alkyl)NC(=O)N(H)—; wherein, $R^{11}$ is selected from hydrogen, alkyl, cycloalkyl, aryl, heteroaryl, and heterocyclyl; and $R^{11a}$ is selected from hydrogen, alkyl, perhaloalkyl, cycloalkyl, aryl, heteroaryl, and heterocyclyl.

The term "aryl" refers to a monocyclic, bicyclic or tricyclic aromatic hydrocarbon ring system. Examples of aryl groups include phenyl, naphthyl, anthracenyl, fluorenyl, indenyl, azulenyl, and the like. Aryl group also includes partially saturated bicyclic and tricyclic aromatic hydrocarbons such as tetrahydro-naphthalene.

When the aryl group is substituted, it is substituted with 1 to 3 substituents selected independently from halogen, nitro, cyano, hydroxy, $C_{1-6}$ alkyl, perhaloalkyl, alkyl-O—, perhaloalkyl-O—, alkyl(alkyl)N—, alkyl(H)N—, $H_2N—$, alkyl-S(=O)$_2$—, alkyl-C(=O)(alkyl)N—, alkyl-C(=O)N(H)—, alkyl(alkyl)NC(=O)—, alkyl(H)NC(=O)—, $H_2NC(=O)—$, alkyl(alkyl)NS(=O)$_2$—, alkyl(H)NS(=O)$_2$—, and $H_2NS(=O)_2—$.

The term "heteroaryl" refers to a 5-14 membered monocyclic, bicyclic, or tricyclic ring system having 1-4 ring heteroatoms selected from O, N, or S, and the remainder ring atoms being carbon (with appropriate hydrogen atoms unless otherwise indicated), wherein at least one ring in the ring system is aromatic. Heteroaryl groups may be optionally substituted with one or more substituents. In one embodiment, 0, 1, 2, 3, or 4 atoms of each ring of a heteroaryl group may be substituted by a substituent. Examples of heteroaryl groups include, but not limited to pyridyl, 1-oxo-pyridyl, furanyl, thienyl, pyrrolyl, oxazolyl, oxadiazolyl, imidazolyl, thiazolyl, isoxazolyl, quinolinyl, pyrazolyl, isothiazolyl, pyridazinyl, pyrimidinyl, pyrazinyl, triazinyl, triazolyl, thiadiazolyl, isoquinolinyl, benzoxazolyl, benzofuranyl, indolizinyl, imidazopyridyl, tetrazolyl, benzimidazolyl, benzothiazolyl, benzothiadiazolyl, benzoxadiazolyl, indolyl, azaindolyl, imidazopyridyl, quinazolinyl, purinyl, pyrrolo[2,3]pyrimidinyl, pyrazolo[3,4]pyrimidinyl, and benzo(b)thienyl, 2,3-thiadiazolyl, 1H-pyrazolo[5,1-c]-1,2,4-triazolyl, pyrrolo[3,4-d]-1,2, 3-triazolyl, cyclopentatriazolyl, 3H-pyrrolo[3,4-c]isoxazolyl, 2,3-dihydro-benzo[1,4]dioxin-6-yl, 2,3-dihydro-benzo[1,4]dioxin-5-yl, 2,3-dihydro-benzofuran-5-yl, 2,3-dihydro-benzofuran-4-yl, 2,3-dihydro-benzofuran-6-yl, 2,3-dihydro-benzofuran-6-yl, 2,3-dihydro-1H-indol-5-yl, 2,3-dihydro-1H-indol-4-yl, 2,3-dihydro-1H-indol-6-yl, 2,3-dihydro-1H-indol-7-yl, benzo[1,3]dioxol-4-yl, benzo[1,3] dioxol-5-yl, 1,2,3,4-tetrahydroquinolinyl, 1,2,3,4-tetrahydroisoquinolinyl, 2,3-dihydrobenzothien-4-yl, 2-oxoindolin-5-yl and the like.

When the heteroaryl group is substituted, it is substituted with 1 to 3 substituents selected independently from halogen, nitro, cyano, hydroxy, $C_{1-6}$ alkyl, perhaloalkyl, alkyl-O—, perhaloalkyl-O—, alkyl(alkyl)N—, alkyl(H)N—, $H_2N—$, alkyl-S(=O)$_2$—, alkyl-C(=O)(alkyl)N—, alkyl-C(=O)N (H)—, alkyl(alkyl)NC(=O)—, alkyl(H)NC(=O)—, $H_2NC(=O)—$, alkyl(alkyl)NS(=O)$_2$—, alkyl(H)NS(=O)$_2$—, and $H_2NS(=O)_2—$.

The term "heterocycle" or "heterocyclic" as used herein, means a 'cycloalkyl' group wherein one or more of the carbon atoms replaced by —O—, —S—, —S(O$_2$)—, —S(O)—, —N(R$^m$)—, —Si(R$^m$)R$^n$—, wherein, R$^m$ and R$^n$ are independently selected from hydrogen, alkyl, aryl, heteroaryl, cycloalkyl, and heterocyclyl. The heterocycle may be connected to the parent molecular moiety through any carbon atom or any nitrogen atom contained within the heterocycle. Examples of monocyclic heterocycle include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1.1-dioxidothiomorpholinyl (thiomorpholine sulfone), thiopyranyl, and trithianyl. Examples of bicyclic heterocycle include, but are not limited to 1,3-benzodioxolyl, 1,3-benzodithiolyl, 2,3-dihydro-1,4-benzodioxinyl, 2,3-dihydro-1-benzofuranyl, 2,3-dihydro-1-benzothienyl, 2,3-dihydro-1H-indolyl and 1,2,3,4-tetrahydroquinolinyl. The term heterocycle also include bridged heterocyclic systems such as azabicyclo[3.2.1]octane, azabicyclo[3.3.1]nonane and the like.

The heterocyclic group, when it is substituted, it may be substituted on a ring carbon atom or a ring hetero atom. For example, it is substituted on a ring carbon with 1-3 substituents selected independently from halogen, nitro, cyano, oxo, $C_{1-6}$ alkyl, perhaloalkyl, $R^{11a}O—$, (alkyl)OC(=O)—, (alkyl)C(=O)O—, $R^{11}(H)NC(=O)—$, $R^{11}(alkyl)NC(=O)—$, (alkyl)C(=O)N(H)—, $R^{11}(H)N—$, $R^{11}(alkyl)N—$, $R^{11}(H)NC(=O)N(H)—$, and $R^{11}(alkyl)NC(=O)N(H)—$; wherein, $R^{11}$ is selected from hydrogen, alkyl, cycloalkyl, aryl, heteroaryl, and heterocyclyl; and $R^{11a}$ is selected from hydrogen, alkyl, perhaloalkyl, cycloalkyl, aryl, heteroaryl, and heterocyclyl.

When the heterocyclic group is substituted on ring nitrogen, it is substituted with a substituent selected from $C_{1-6}$ alkyl, (alkyl)SO$_2$—, (alkyl)C(=O)—, (alkyl)OC(=O)—, $R^{11}(H)NC(=O)—$, and $R^{11}(alkyl)NC(=O)—$; wherein, $R^{11}$ is selected from hydrogen, alkyl, cycloalkyl, aryl, heteroaryl, and heterocyclyl; and $R^{11a}$ is selected from hydrogen, alkyl, perhaloalkyl, cycloalkyl, aryl, heteroaryl, and heterocyclyl.

When a parent group is substituted with an "oxo" group, it means a divalent oxygen (=O) becomes attached to a carbon atom of the parent group. For example, when a CH$_2$ group is substituted with an oxo substituent, the parent CH$_2$ group becomes a carbonyl (C=O) group; thus, oxo substituted on cyclohexane forms a cyclohexanone, for example.

The term "annulated" means the ring system under consideration is either annulated with another ring at a carbon atom of the cyclic system or across a bond of the cyclic system as in the case of spiro or fused ring systems.

The term "bridged" means the ring system under consideration contain an alkylene bridge having 1 to 4 methylene units joining two non-adjacent ring atoms.

In a specific embodiment, the invention provides a compound, its stereoisomers, racemates, pharmaceutically acceptable salts thereof as described hereinabove wherein the compound of general formula I is selected from:

1. dimethyl ((2S,2'S)-((2S,2'S)-2,2'-(5,5'-(7,8-dihydro-6H-dibenzo[f,h][1,5]dioxonine-3,11-diyl)bis(1H-imidazole-5,2-diyl))bis(pyrrolidine-2,1-diyl))bis(3-methyl-1-oxobutane-2,1-diyl))dicarbamate (Compound 1);
2. methyl ((S)-1-((S)-2-(5-(11-(2-((S)-1-((S)-2-(methoxycarbonyl)amino-3-methylbutanoyl)pyrrolidin-2-yl)-1H-imidazol-5-yl)-7,8-dihydro-6H-dibenzo[f,h][1,5]dioxonin-3-yl)-4-chloro-1H-imidazol-2-yl)pyrrolidin-1-yl)-3-methyl-1-oxobutan-2-yl)carbamate (Compound 2);
3. dimethyl ((2S,2'S)-((2S,2'S)-2,2'-(5,5'-(7,8-dihydro-6H-dibenzo[f,h][1,5]dioxonine-3,11-diyl)bis(4-chloro-1H-imidazole-5,2-diyl))bis(pyrrolidine-2,1-diyl))bis(3-methyl-1-oxobutane-2,1-diyl))dicarbamate (Compound 3);
4. dimethyl ((2S,2'S)-((2S,2'S)-2,2'-(5,5'-(6,7,8,9-tetrahydrodibenzo[b,d][1,6]dioxecine-3,12-diyl)bis(1H-imidazole-5,2-diyl))bis(pyrrolidine-2,1-diyl))bis(3-methyl-1-oxobutane-2,1-diyl))dicarbamate (Compound 4);
5. dimethyl ((2S,2'S)-((2S,2'S)-2,2'-(5,5'-(7,7-dimethyl-7,8-dihydro-6H-dibenzo[f,h][1,5]dioxonine-3,11-diyl)bis(1H-imidazole-5,2-diyl))bis(pyrrolidine-2,1-diyl))bis(3-methyl-1-oxobutane-2,1-diyl))dicarbamate (Compound 5);
6. methyl ((S)-1-((S)-2-(5-(11-(2-((S)-1-((S)-2-(methoxycarbonyl)amino-3-methylbutanoyl)pyrrolidin-2-yl)-4-chloro-1H-imidazol-5-yl)-7,7-dimethyl-7,8-dihydro-6H-dibenzo[f,h][1,5]dioxonin-3-yl)-1H-imidazol-2-yl)pyrrolidin-1-yl)-3-methyl-1-oxobutan-2-yl)carbamate (Compound 6);
7. dimethyl ((2S,2'S)-((2S,2'S)-2,2'-(5,5'-(7,7-dimethyl-7,8-dihydro-6H-dibenzo[f,h][1,5]dioxonine-3,11-diyl)bis(4-chloro-1H-imidazole-5,2-diyl))bis(pyrrolidine-2,1-diyl))bis(3-methyl-1-oxobutane-2,1-diyl))dicarbamate (Compound 7);
8. dimethyl ((2S,2'S)-((2S,2'S)-2,2'-(5,5'-(7,7-dimethyl-7,8-dihydro-6H-dibenzo[f,h][1,5]dioxonine-3,11-diyl)bis(4-ethyl-1H-imidazole-5,2-diyl))bis(pyrrolidine-2,1-diyl))bis(3-methyl-1-oxobutane-2,1-diyl))dicarbamate (Compound 8);
9. dimethyl ((2S,2'S)-((2S,2'S)-2,2'-(5,5'-(7,7-dimethyl-7,8-dihydro-6H-dibenzo[f,h][1,5]dioxonine-3,11-diyl)bis(4-cyclopropyl-1H-imidazole-5,2-diyl))bis(pyrrolidine-2,1-diyl))bis(3-methyl-1-oxobutane-2,1-diyl))dicarbamate. (Compound 9);
10. dimethyl ((2S,2'S)-((2S,2'S)-2,2'-(5,5'-(6',8'-dihydrospiro[cyclopropane-1,7'-dibenzo[f,h][1,5]dioxonine]-3',11'-diyl)bis(1H-imidazole-5,2-diyl))bis(pyrrolidine-2,1-diyl))bis(3-methyl-1-oxobutane-2,1-diyl))dicarbamate (Compound 10); and
11. dimethyl ((2S,2'S)-((2S,2'S)-2,2'-(5,5'-(6,11-dihydrotribenzo[b,d,h][1,6]dioxecine-3,14-diyl)bis(1H-imidazole-5,2-diyl))bis(pyrrolidine-2,1-diyl))bis(3-methyl-1-oxobutane-2,1-diyl))dicarbamate (Compound 11).

According to an embodiment of the present invention, the compounds of general formula (I) where all the symbols are as defined earlier can be prepared by methods illustrated in the Schemes below and in the examples. Representative procedures are shown below, however; the disclosure should not be construed to limit the scope of the invention arriving at compound of formula (I) as disclosed hereinabove.

SCHEME 1

Scheme 1:

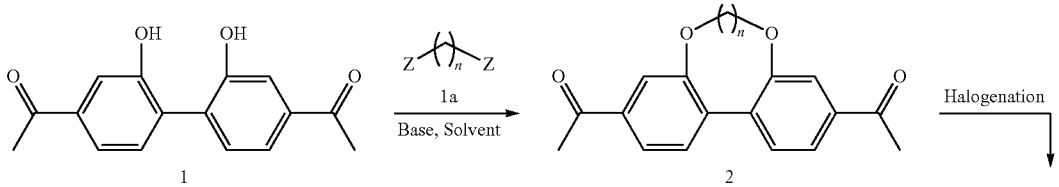

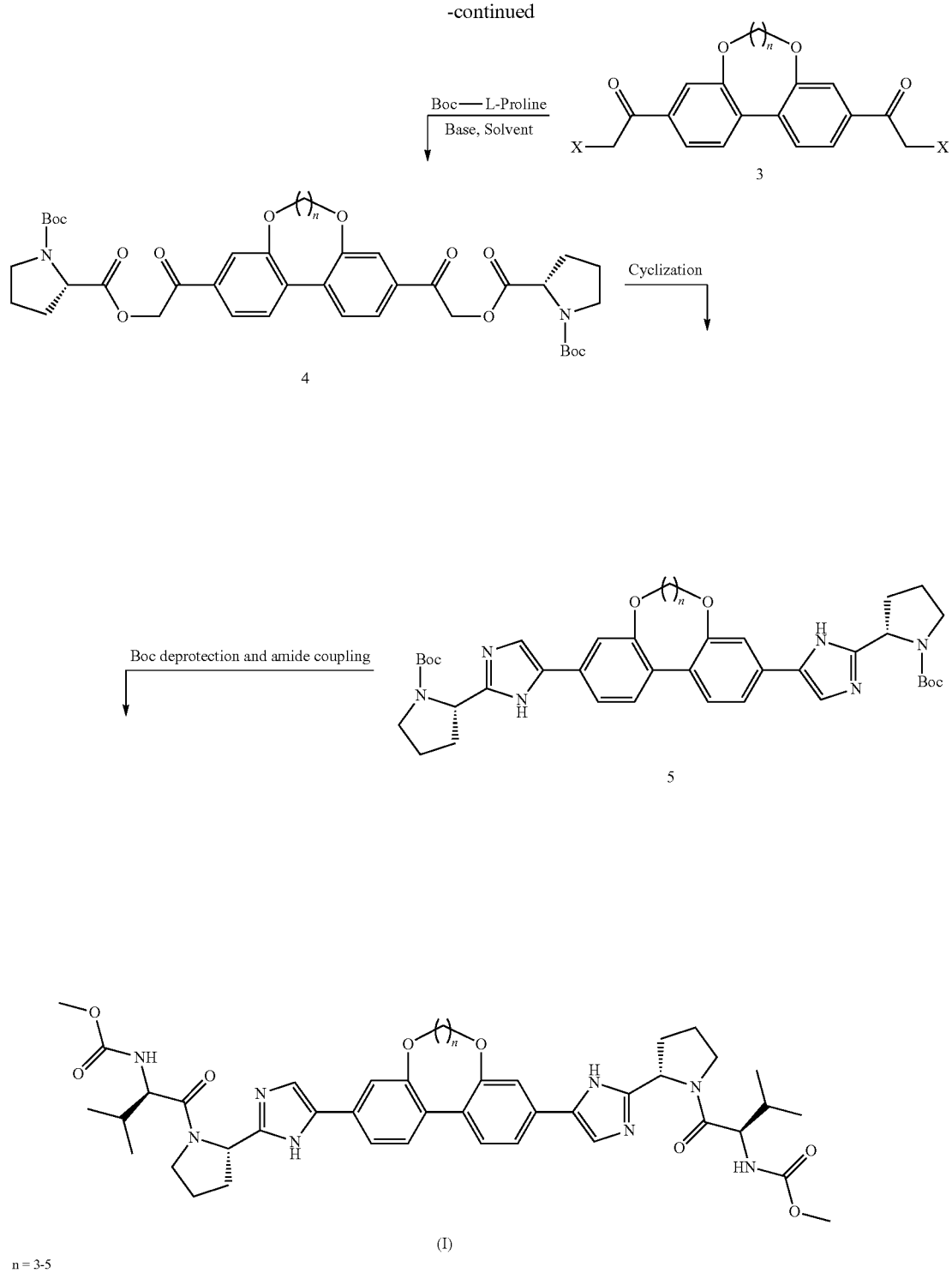

Reaction of 1 (synthesized according to methods described in WO 2010/111673) with 1a (where Z depicts leaving groups such as Br, I, Cl, OTs, or OMs) in presence of an organic or inorganic base, for example, $K_2CO_3$, $Cs_2CO_3$, $Na_2CO_3$ or $Et_3N$ and solvents, for example, DMF and DMSO, lead to the formation of 2. Halogenation of 2 using halogenating agents like NBS, NCS, NIS, bromine and iodine leads to the synthesis of 3 (where X=halogen) which undergoes O-alkylation using Boc-L-proline leading to the formation of 4. Cyclization of 4 using a suitable reagent, for example, ammonium acetate in toluene, xylene, or 1,4-dioxane leads to the formation of 5. The intermediate 5 thus obtained is deprotected under acidic conditions and the amine thus obtained is coupled with an acid such as (S)-2-[(methoxycarbonyl)-amino]-3-methylbutanoic acid using methods known in the art to generate compounds of formula (I).

SCHEME 2
Scheme 2:
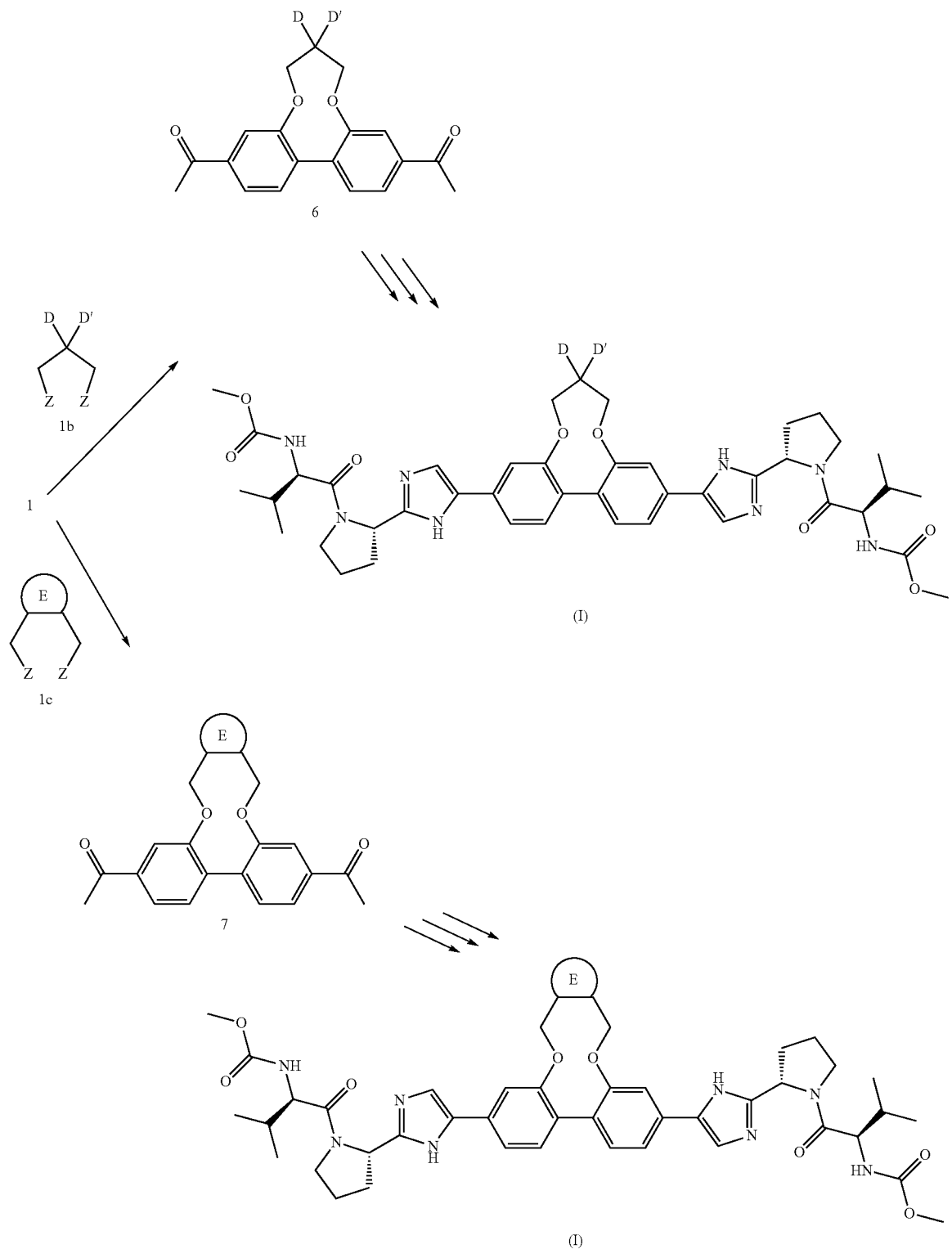
In accordance with an embodiment, 1 is treated with 1b (where D and D' are dialkyl, difluoro or both D and D' are fused to form a saturated ring system with or without heteroa- tom in the ring) or 1c (where E is 3-6 membered carbocyclic or heterocyclic ring system) in a similar way as depicted in Scheme 1 to generate 6 or 7, respectively. Intermediates 6 or 7 is further elaborated to compound having the general formula (I) using reaction conditions and reagent depicted in Scheme 1.

amino)-3-methylbutanoic acid in a similar manner as depicted in scheme 1 to generate the final compound of formula (I).

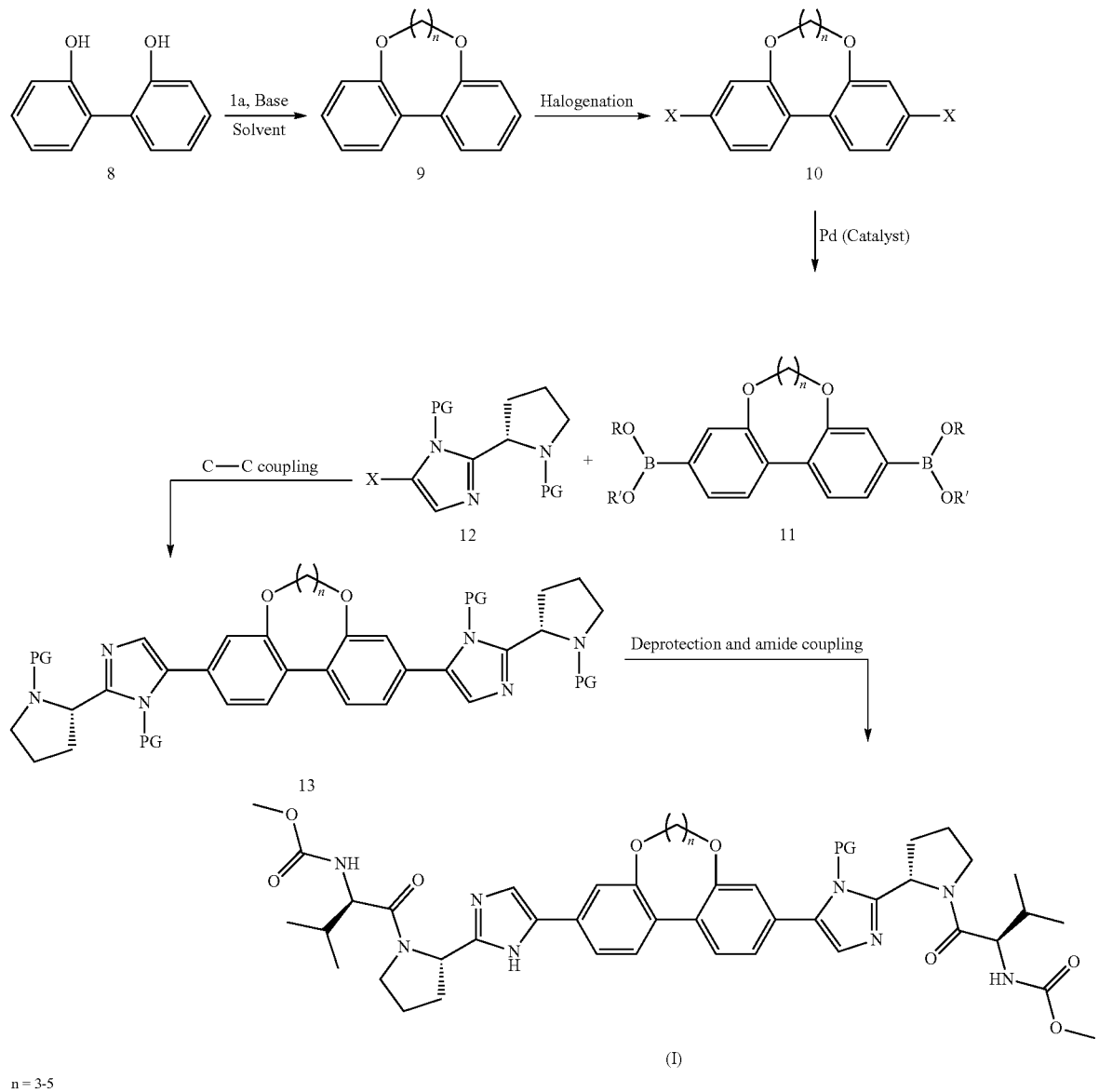

SCHEME 3

Scheme 3:

n = 3-5

Treatment of 8 with 1a in presence of a suitable base and solvent (as illustrated in Scheme 1) leads to the formation of 9 which on halogenation with a suitable halogenating agent according to the methods known in the art lead to the formation of 10. The halo group (X) in 10 is converted to the boronate ester boronic acid functionality (11) via Pd-catalysis and coupled with 12 (synthesized according to methods described in WO 2011/15657, wherein PG=Protecting Group) to obtain 13 which is de-protected under acidic conditions and then coupled with (S)-2-((methoxycarbonyl)-

Scheme 4:

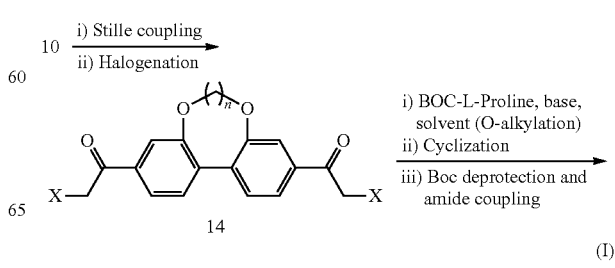

i) Stille coupling
ii) Halogenation i) BOC-L-Proline, base, solvent (O-alkylation)
ii) Cyclization
iii) Boc deprotection and amide coupling (I)

Alternatively, 10 is subjected to Stille coupling by methods well known in the literature followed by halogenation of acetyl group to yield 14 (X=Cl, Br, I) which is further elaborated to generate the final compound of formula (I) by following the synthetic sequence depicted in Scheme 1.
SCHEME 5
Scheme 5:
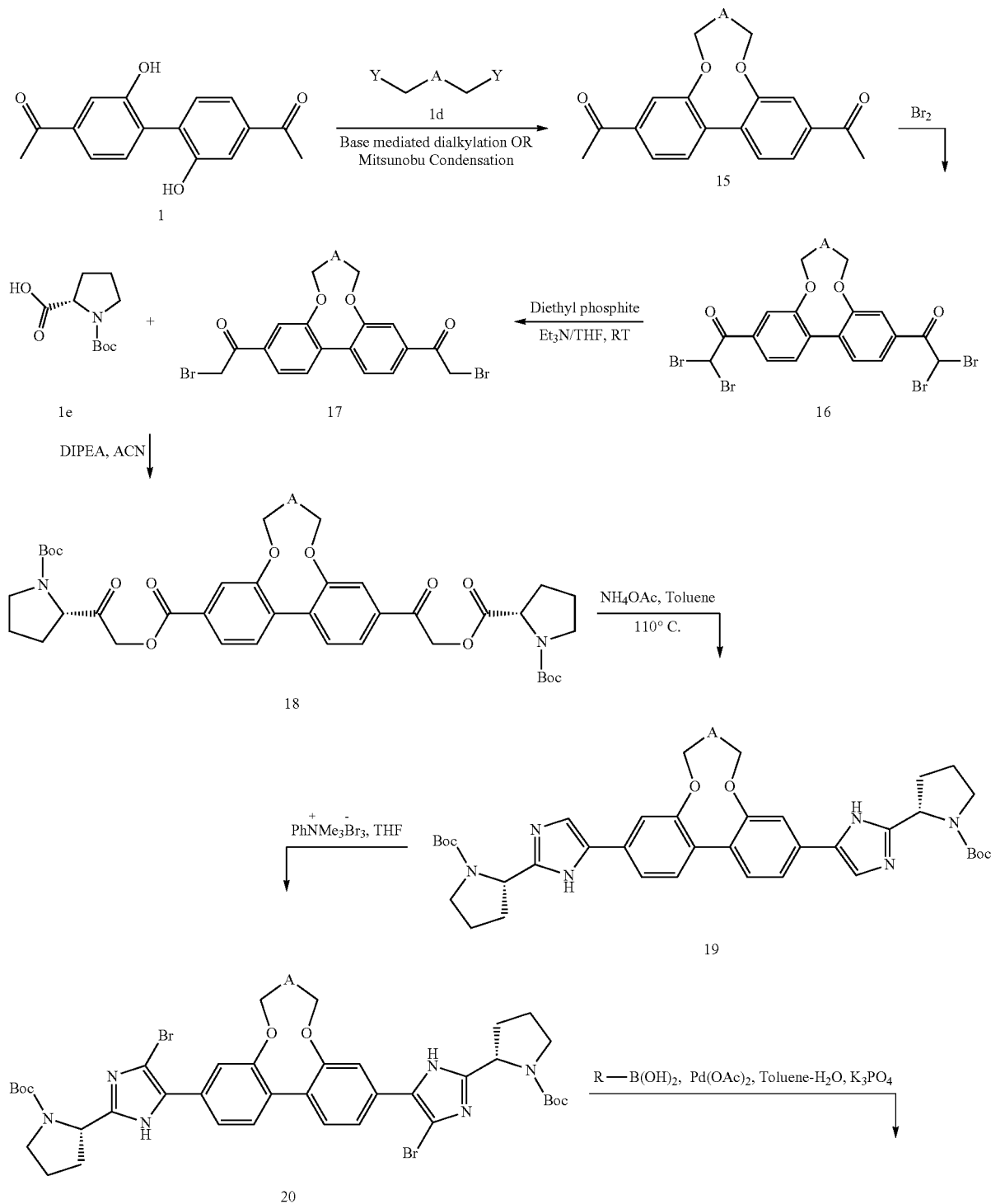

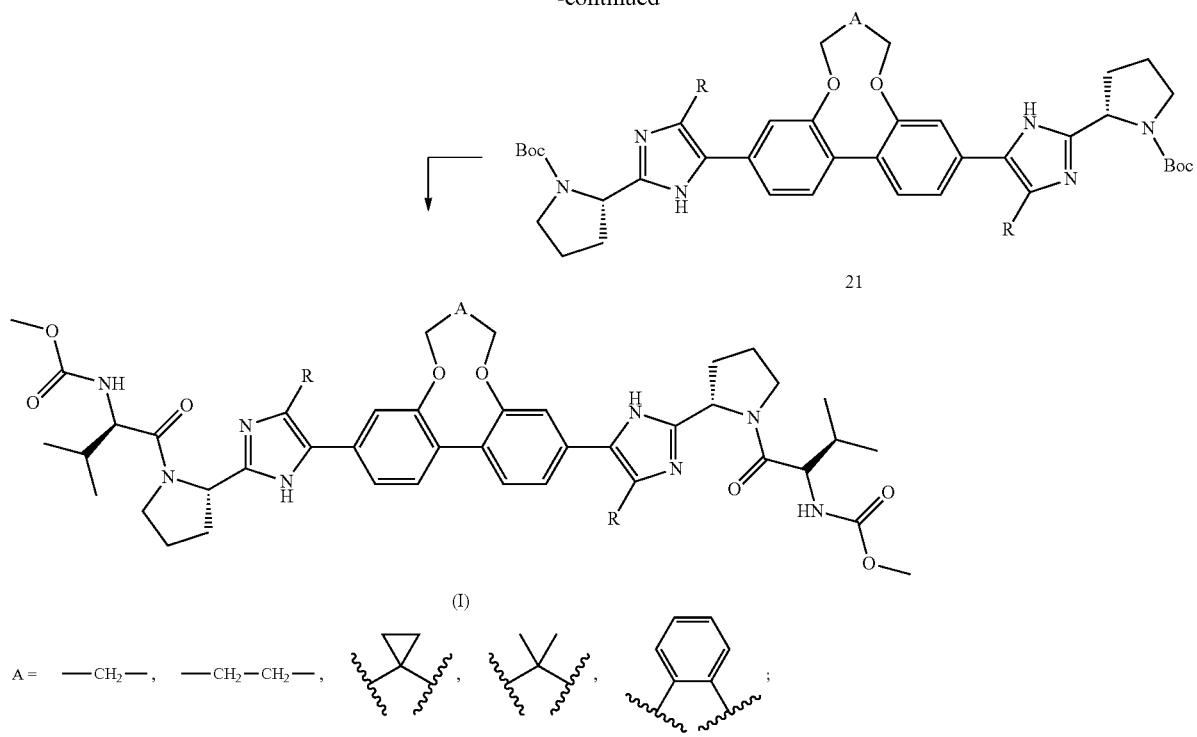
(I)
A = —CH₂—, —CH₂—CH₂—, [cyclopropyl], [gem-dimethyl], [benzo];
R = Ethyl, Cyclopropyl
Compound of formula (I) is obtained from 1 by following the synthetic routes depicted in Scheme 5.
SCHEME 6
Scheme 6:
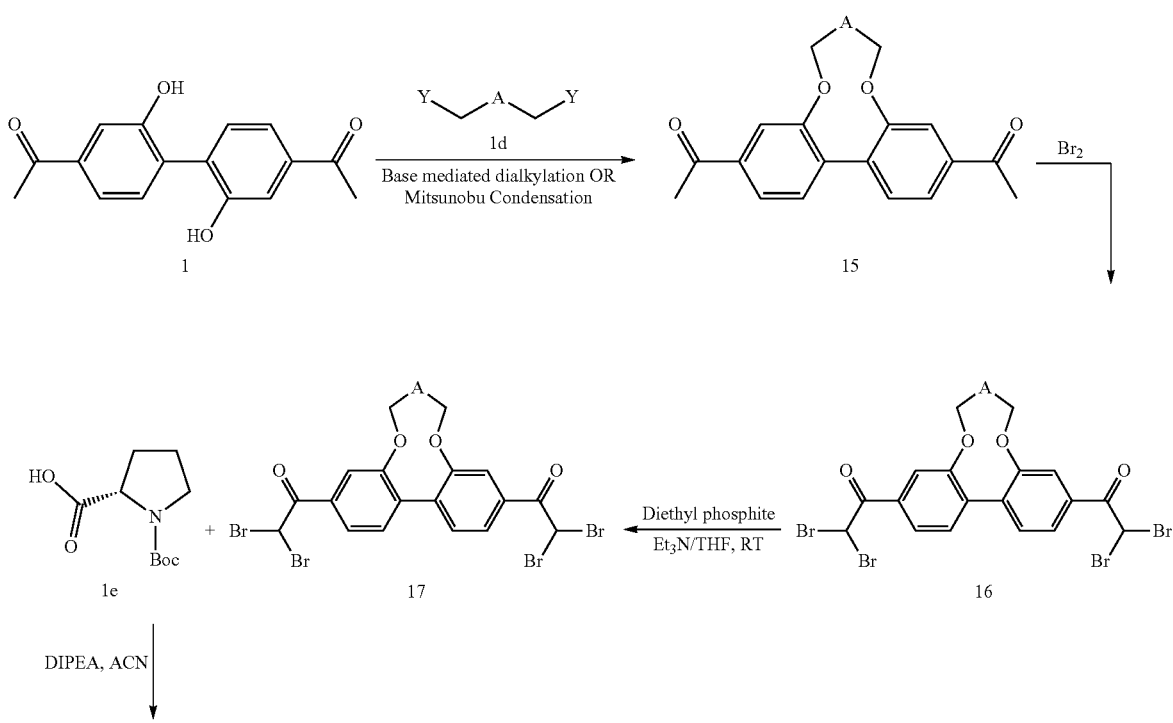

-continued

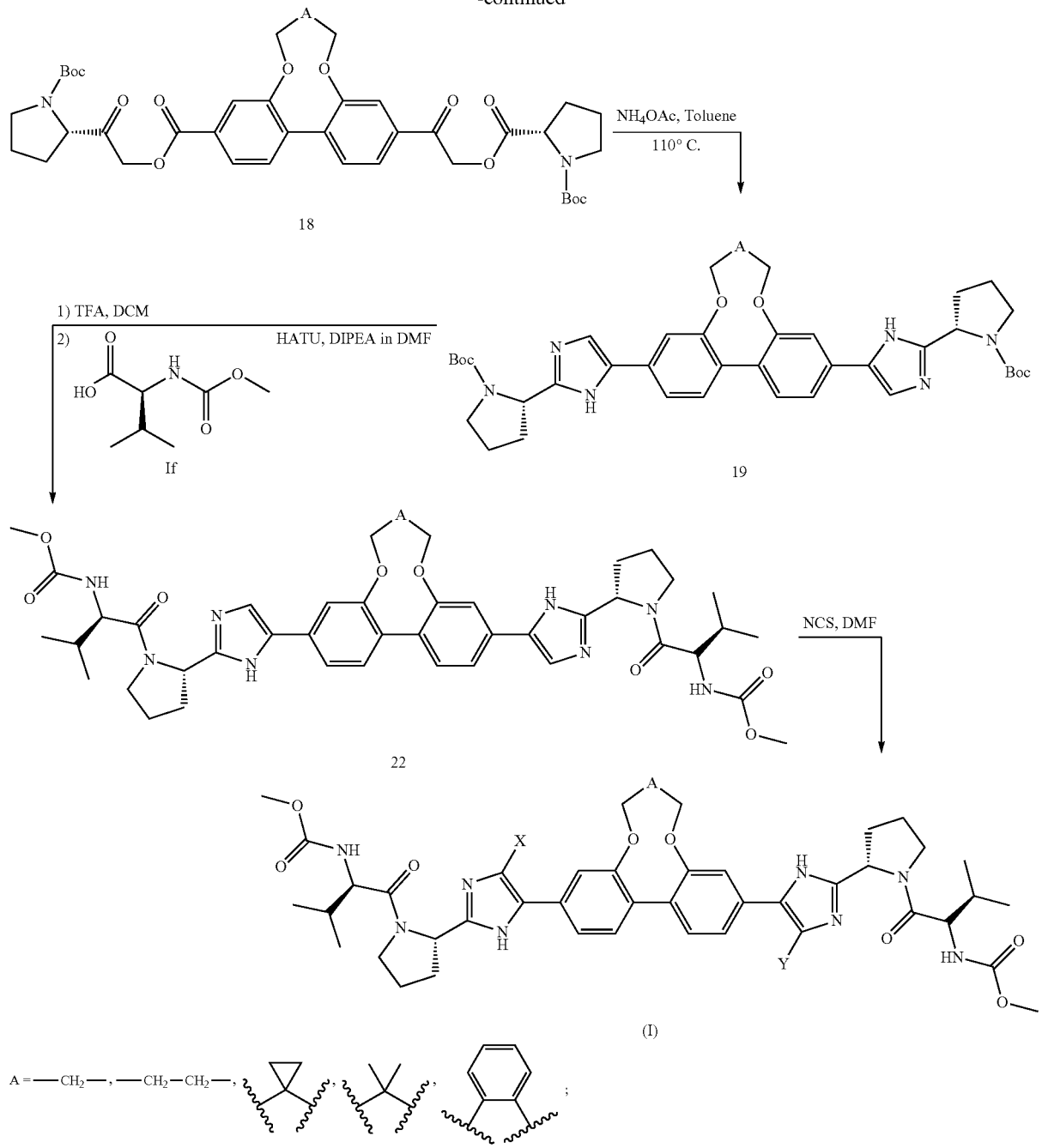

X = Y = Cl or X = H and Y = Cl

Compound of formula (I) is also obtained from 1 by following the synthetic routes depicted in Scheme 6.

The intermediates and the compounds of the present invention are obtained, e.g., in pure form, in a manner known per se, for example by distilling off the solvent in vacuum and recrystallizing the residue obtained from a suitable solvent, such as pentane, diethyl ether, isopropyl ether, chloroform, dichloromethane, ethyl acetate, acetone or their combinations or subjecting it to one of the purification methods, such as column chromatography (e.g., flash chromatography) on a suitable support material such as alumina or silica gel using eluent such as dichloromethane, ethyl acetate, hexane, methanol, acetone and their combinations. Preparative HPLC method is also used for the purification of molecules described herein.

Salts of the compounds of formula (I) are obtained by dissolving the compound in a suitable solvent, for example, a chlorinated hydrocarbon, such as methylene chloride or chloroform or a low molecular weight aliphatic alcohol, for example, ethanol or isopropanol, which is then treated with the desired acid or base, for example, as described in Berge S. M. et al., "Pharmaceutical Salts, a review article," *Journal of*

*Pharmaceutical Sciences*, volume 66, page 1-19 (1977) and in the Handbook of Pharmaceutical Salts—Properties, Selection, and Use, by P. H. Einrich Stahland Camille G. wermuth, Wiley-VCH (2002). Lists of suitable salts can also be found in *Remington's Pharmaceutical Sciences,* 18th ed., Mack Publishing Company, Easton, Pa., 1990, p. 1445, and *Journal of Pharmaceutical Science,* 66, 2-19 (1977). For example, they can be a salt of an alkali metal (e.g., sodium or potassium), alkaline earth metal (e.g., calcium), or ammonium salt.

The compound of the invention or a composition thereof can potentially be administered as a pharmaceutically acceptable acid-addition, base neutralized or addition salt, formed by reaction with inorganic acids, such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base, such as sodium hydroxide, potassium hydroxide. The conversion to a salt is accomplished by treatment of the base compound with at least a stoichiometric amount of an appropriate acid. Typically, the free base is dissolved in an inert organic solvent such as diethyl ether, ethyl acetate, chloroform, ethanol, methanol, and the like, and the acid is added in a similar solvent. The mixture is maintained at a suitable temperature (e.g., between 0° C. and 50° C.). The resulting salt precipitates spontaneously or can be brought out of solution with a less polar solvent.

The stereoisomers of the compounds of formula I of the present invention may be prepared by stereospecific synthesis or resolution of the racemic compound using an optically active amine, acid or complex forming agent, and separating the diastereomeric salt/complex by fractional crystallization or by column chromatography.

The compounds of the invention, their tautomeric forms, their stereoisomers, their pharmaceutically acceptable salts, their combinations with suitable medicament and pharmaceutical compositions containing them exhibited a broader spectrum of activity as they show inhibitory actions against multiple genotypes of HCV with high potency.

The compounds of the invention, their tautomeric forms, their stereoisomers, their pharmaceutically acceptable salts, their combinations with suitable medicament and pharmaceutical compositions containing them, have demonstrated good stability in human liver microsomes and exhibited promising oral bioavailability in preclinical species with enhanced liver concentrations and high liver to plasma ratio.

Compounds of the present invention were prepared using synthetic Scheme I provided below:

SCHEME I
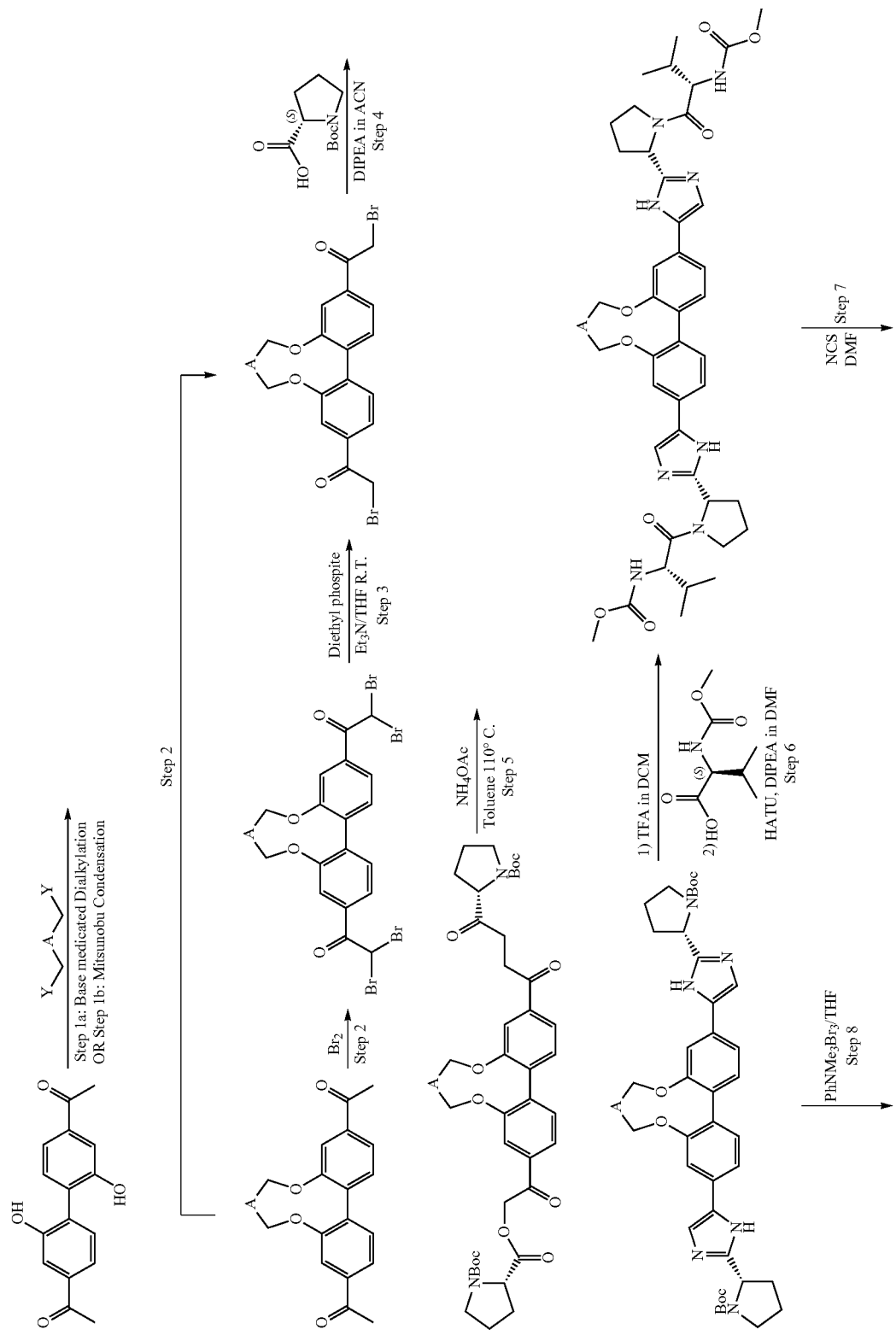

-continued
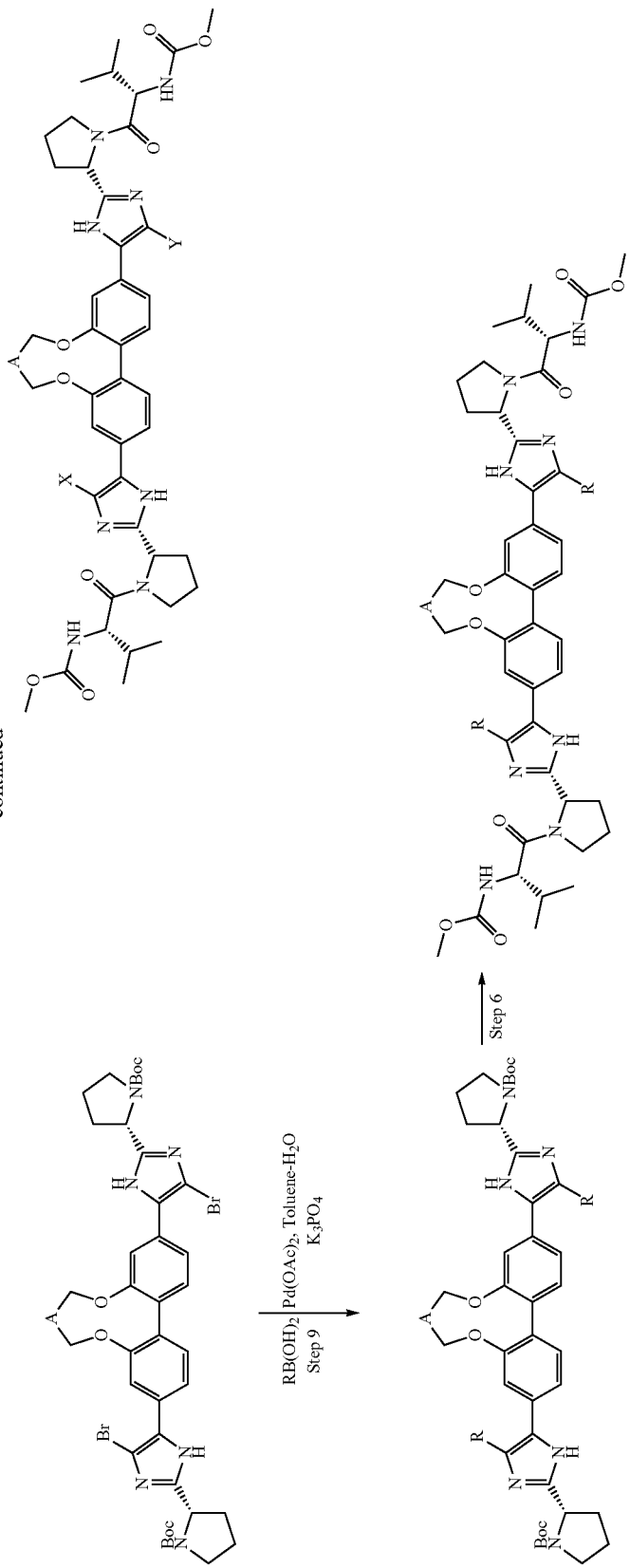
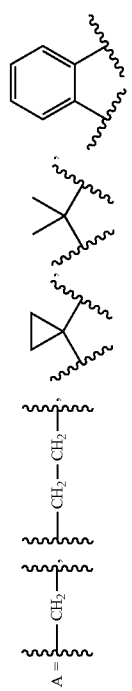
A = —CH₂—CH₂—, —CH₂—;
X = Y = Cl or X = H & Y = Cl
R = Et, Cyclopropyl A further embodiment of the present invention includes pharmaceutical compositions comprising any single compound, a tautomer, or isomer thereof, a combination of two or more compounds delineated herein, tautomers, or isomers thereof, or a pharmaceutically acceptable salt or salts thereof, with a pharmaceutically acceptable carrier or excipient.

Yet a further embodiment of the present invention is a pharmaceutical composition comprising any single compound, a tautomer, or isomer thereof, or a combination of two or more compounds delineated herein, tautomers, or isomers thereof, or a pharmaceutically acceptable salt or salts thereof, in combination with one or more agents known in the art, with a pharmaceutically acceptable carrier or excipient.

The pharmaceutically acceptable carrier (or excipient) is preferably one that is chemically inert to the compound of the invention and one that has no detrimental side effects or toxicity under the conditions of use. Such pharmaceutically acceptable carriers preferably include saline (e.g., 0.9% saline), Cremophor EL (which is a derivative of castor oil and ethylene oxide available from Sigma Chemical Co., St. Louis, Mo.) (e.g., 5% Cremophor EL/5% ethanol/90% saline, 10% Cremophor EL/90% saline, or 50% Cremophor EL/50% ethanol), propylene glycol (e.g., 40% propylene glycol/10% ethanol/50% water), polyethylene glycol (e.g., 40% PEG 400/60% saline), and alcohol (e.g., 40% ethanol/60% water). A preferred pharmaceutical carrier is polyethylene glycol, such as PEG 400, and particularly a composition comprising 40% PEG 400 and 60% water or saline. The choice of carrier will be determined in part by the particular compound chosen, as well as by the particular method used to administer the composition. Accordingly, there is a wide variety of suitable formulations of the pharmaceutical composition of the present invention.

The formulations for oral, aerosol, parenteral, subcutaneous, intravenous, intra-arterial, intramuscular, inter-peritoneal, rectal, and vaginal administration are merely exemplary and are in no way limiting.

The pharmaceutical compositions can be administered parenterally, e.g., intravenously, intra-arterially, subcutaneously, intra-dermally, intra-thecally, or intramuscularly. Thus, the invention provides compositions for parenteral administration that comprise a solution of the compound of the invention dissolved or suspended in an acceptable carrier suitable for parenteral administration, including aqueous and non-aqueous, isotonic sterile injection solutions.

Overall, the requirements for effective pharmaceutical carriers for parenteral compositions are well known to those of ordinary skill in the art. See *Pharmaceutics and Pharmacy Practice*, J.B. Lippincott Company, Philadelphia, Pa., Banker and Chalmers, eds., pages 238-250 (1982), and *ASHP Handbook on Injectable Drugs*, Toissel, 4th ed., pages 622-630 (1986). Such compositions include solutions containing antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compound can be administered in a physiologically acceptable diluent in a pharmaceutical carrier, such as a sterile liquid or mixture of liquids, including water, saline, aqueous dextrose and related sugar solutions, an alcohol, such as ethanol, isopropanol (for example in topical applications), or hexadecyl alcohol, glycols, such as propylene glycol or polyethylene glycol, dimethylsulfoxide, glycerol ketals, such as 2,2-dimethyl-1,3-dioxolane-4-methanol, ethers, such as poly(ethyleneglycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils useful in parenteral formulations include petroleum, animal, vegetable, and synthetic oils. Specific examples of oils useful in such formulations include peanut, soybean, sesame, cottonseed, corn, olive, petrolatum, and mineral oil. Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylene polypropylene copolymers, (d) amphoteric detergents such as, for example, alkyl-β-aminopropionates, and 2-alkyl-imidazoline quaternary ammonium salts, and (e) mixtures thereof.

The parenteral formulations typically will contain from about 0.5% or less to about 25% or more by weight of a compound of the invention, a tautomer, or isomer thereof, or salt thereof in solution. Preservatives and buffers can be used. In order to minimize or eliminate irritation at the site of injection, such compositions can contain one or more non-ionic surfactants having a hydrophile-lipophile balance (HLB) of from about 12 to about 17. The quantity of surfactant in such formulations will typically range from about 5% to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets.

Formulations suitable for oral administration can consist of (a) liquid solutions, such as an effective amount of a compound of the invention, a tautomer, or isomer thereof, or salt thereof dissolved in diluents, such as water, saline, or orange juice; (b) capsules, sachets, tablets, lozenges, and troches, each containing a pre-determined amount of the compound of the invention, a tautomer, or isomer thereof, or salt thereof, as solids or granules; (c) powders; (d) suspensions in an appropriate liquid; and (e) suitable emulsions. Liquid formulations can include diluents, such as water and alcohols, for example, ethanol, benzyl alcohol, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and cornstarch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible excipients. Lozenge forms can comprise the compound ingredient in a flavor, usually sucrose and acacia or tragacanth, as well as pastilles comprising a compound of the invention in an inert base, such as gelatin and glycerin, or sucrose and acacia, emulsions, gels, and the like containing, in addition to the compound of the invention, such excipients as are known in the art.

A compound of the present invention, a tautomer, or isomer thereof, or salt thereof alone or in combination with other suitable components, can be made into aerosol formulations to be administered via inhalation. A compound of the invention, a tautomer, or isomer thereof, or salt thereof is preferably supplied in finely divided form along with a surfactant and propellant. Typical percentages of the compounds of the invention can be about 0.01% to about 20% by weight, preferably about 1% to about 10% by weight. The surfactant must, of course, be nontoxic, and preferably soluble in the propellant. Representative of such surfactants are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides can be employed. The surfactant can constitute from about 0.1% to about 20% by weight of the composition, preferably from about 0.25% to about 5%. The balance of the composition is ordinarily propellant. A carrier can also be included as desired, e.g., lecithin, for intranasal delivery. These aerosol formulations can be placed into acceptable pressurized propellants, such as dichlorodifluoromethane, propane, nitrogen, and the like. They also can be formulated as pharmaceuticals for non-pressured preparations, such as in a nebulizer or an atomizer. Such spray formulations can be used to spray mucosa.

Additionally, the compound of the invention, a tautomer, or isomer thereof, or salt thereof can be made into suppositories by mixing with a variety of bases, such as emulsifying bases or water-soluble bases. Formulations suitable for vaginal administration can be presented as pessaries, tampons, creams, gels, pastes, foams, or spray formulas containing, in addition to the compound ingredient, such carriers as are known in the art to be appropriate.

The concentration of the compound, a tautomer, or isomer thereof, or salt thereof in the pharmaceutical formulations can vary, e.g., from less than about 1% to about 10%, to as much as 20% to 50% or more by weight, and can be selected primarily by fluid volumes, and viscosities, in accordance with the particular mode of administration selected.

For example, a typical pharmaceutical composition for intravenous infusion could be made up to contain 250 ml of sterile Ringer's solution, and 100 mg of at least one compound, a tautomer, or isomer thereof, or salt thereof of the invention. Actual methods for preparing parenterally administrable compounds of the invention will be known or apparent to those skilled in the art and are described in more detail in, for example, *Remington's Pharmaceutical Science* (17th ed., Mack Publishing Company, Easton, Pa., 1985).

It will be appreciated by one of ordinary skill in the art that, in addition to afore described pharmaceutical compositions, the compound of the invention, a tautomer, or isomer thereof, or salt thereof can be formulated as inclusion complexes, such as cyclodextrin inclusion complexes, or liposomes. Liposomes can serve to target a compound of the invention to a particular tissue, such as lymphoid tissue or cancerous hepatic cells. Liposomes can also be used to increase the half-life of a compound of the invention. Many methods are available for preparing liposomes, as described in, for example, Szoka et al., *Ann. Rev. Biophys. Bioeng.*, 9, 467 (1980) and U.S. Pat. Nos. 4,235,871, 4,501,728, 4,837,028, and 5,019,369.

The compounds of the invention, a tautomer, or isomer thereof, or salt thereof can be administered in a dose sufficient to treat the disease, condition or disorder. Such doses are known in the art (see, for example, the *Physicians' Desk Reference* (2004)). The compounds can be administered using techniques such as those described in, for example, Wasserman et al., Cancer, 36, pp. 1258-1268 (1975) and *Physicians' Desk Reference*, 58th ed., Thomson PDR (2004).

Suitable doses and dosage regimens can be determined by conventional range-finding techniques known to those of ordinary skill in the art. Generally, treatment is initiated with smaller dosages that are less than the optimum dose of the compound of the present invention. Thereafter, the dosage is increased by small increments until the optimum effect under the circumstances is reached. The present method can involve the administration of about 0.1 µg to about 50 mg of at least one compound of the invention per kg body weight of the individual. For a 70 kg patient, dosages of from about 10 µg to about 200 mg of the compound of the invention would be more commonly used, depending on a patient's physiological response.

By way of example and not intending to limit the invention, the dose of the pharmaceutically active agent(s) described herein for methods of treating or preventing a disease or condition as described above can be about 0.001 to about 1 mg/kg body weight of the subject per day, for example, about 0.001 mg, 0.002 mg, 0.005 mg, 0.010 mg, 0.015 mg, 0.020 mg, 0.025 mg, 0.050 mg, 0.075 mg, 0.1 mg, 0.15 mg, 0.2 mg, 0.25 mg, 0.5 mg, 0.75 mg, or 1 mg/kg body weight per day. The dose of the pharmaceutically active agent(s) described herein for the described methods can be about 1 to about 1000 mg/kg body weight of the subject being treated per day, for example, about 1 mg, 2 mg, 5 mg, 10 mg, 15 mg, 0.020 mg, 25 mg, 50 mg, 75 mg, 100 mg, 150 mg, 200 mg, 250 mg, 500 mg, 750 mg, or 1000 mg/kg body weight per day.

In accordance with embodiments, the present invention provides methods of treating, preventing, ameliorating, and/or inhibiting a hepatitis C virus infection comprising administering a compound of formula (I) or a salt thereof.

The compounds of the present invention are effective against the HCV 1b and 2a genotype. It should also be understood that the compounds of the present invention can inhibit multiple genotypes of the HCV. Hence, in accordance with an embodiment of the invention, the compounds of the present invention are active against the 1a, 1b, 2a, 2b, 3a, 4a, and 5a genotypes of the HCV.

The terms "treat," "prevent," "ameliorate," and "inhibit," as well as words stemming therefrom, as used herein, do not necessarily imply 100% or complete treatment, prevention, amelioration, or inhibition. Rather, there are varying degrees of treatment, prevention, amelioration, and inhibition of which one of ordinary skill in the art recognizes as having a potential benefit or therapeutic effect. In this respect, the inventive methods can provide any amount of any level of treatment, prevention, amelioration, or inhibition of the disorder in a mammal. For example, a disorder, including symptoms or conditions thereof, may be reduced by, for example, 100%, 90%, 80%, 70%, 60%, 50%, 40%, 30%, 20%, or 10%. Furthermore, the treatment, prevention, amelioration, or inhibition provided by the inventive method can include treatment, prevention, amelioration, or inhibition of one or more conditions or symptoms of the disorder. Also, for purposes herein, "treatment," "prevention," "amelioration," or "inhibition" can encompass delaying the onset of the disorder, or a symptom or condition thereof.

In accordance with the invention, the term subject includes an "animal" which in turn includes a mammal such as, without limitation, the order Rodentia, such as mice, and the order Lagomorpha, such as rabbits. It is preferred that the mammals are from the order Carnivora, including Felines (cats) and Canines (dogs). It is more preferred that the mammals are from the order Artiodactyla, including Bovines (cows) and Swine (pigs) or of the order Perssodactyla, including Equines (horses). It is most preferred that the mammals are of the order Primates, Ceboids, or Simoids (monkeys) or of the order Anthropoids (humans and apes). An especially preferred mammal is the human.

The term "viral infection" refers to the introduction of a virus into cells or tissues, e.g., hepatitis C virus (HCV). In general, the introduction of a virus is also associated with replication. Viral infection may be determined by measuring virus antibody titer in samples of a biological fluid, such as blood, using, e.g., enzyme immunoassay. Other suitable diagnostic methods include molecular based techniques, such as RT-PCR, direct hybrid capture assay, nucleic acid sequence based amplification, and the like. A virus may infect an organ, e.g., liver, and cause disease, e.g., hepatitis, cirrhosis, chronic liver disease and hepatocellular carcinoma.

The term "immune modulator" refers to any substance meant to alter the working of the humoral or cellular immune system of a subject. Such immune modulators include inhibitors of mast cell-mediated inflammation, interferons, interleukins, prostaglandins, steroids, cortico-steroids, colony-stimulating factors, chemotactic factors, etc.

It will be further appreciated that compounds of the present invention can be administered as the sole active pharmaceutical agent, or used in combination with one or more agents to treat or prevent hepatitis C infections or the symptoms associated with HCV infection. Other agents to be administered in combination with a compound or combination of compounds of the present invention include therapies for diseases caused by HCV infection that suppresses HCV viral replication by direct or indirect mechanisms. These agents include, but not limited to, host immune modulators (for example, interferon-alpha, pegylated interferon-alpha, consensus interferon, interferon-beta, interferon-gamma, CpG oligonucleotides and the like); antiviral compounds that inhibit host cellular functions such as inosine monophosphate dehydrogenase (for example, ribavirin and the like); cytokines that modulate immune function (for example, interleukin 2, interleukin 6, and interleukin 12); a compound that enhances the development of type 1 helper T cell response; interfering RNA; antisense RNA; vaccines comprising HCV antigens or antigen adjuvant combinations directed against the HCV; agents that interact with host cellular components to block viral protein synthesis by inhibiting the internal ribosome entry site (IRES) initiated translation step of HCV viral replication or to block viral particle maturation and release with agents targeted toward the viroporin family of membrane proteins such as, for example, HCV P7 and the like; and any agent or combination of agents that inhibit the replication of HCV by targeting other proteins of the viral genome involved in the viral replication and/or interfere with the function of other viral targets, such as inhibitors of NS3NS4A protease, NS3 helicase, NS5B polymerase, NS4A protein and NS5A protein.

According to yet another embodiment, the pharmaceutical compositions of the present invention may further comprise inhibitor(s) of other targets in the HCV life cycle, including, but not limited to, helicase, polymerase, metalloprotease, NS4A protein, NS5A protein, and internal ribosome entry site (IRES).

Accordingly, one embodiment of the present invention is directed to a method for treating or preventing an infection caused by an RNA-containing virus comprising co-administering to a patient in need of such treatment one or more agents selected from the group consisting of a host immune modulator and a second or more antiviral agents, or a combination thereof, with a therapeutically effective amount of a compound or combination of compounds of the present invention, or a pharmaceutically acceptable salt thereof. Examples of the host immune modulator are, but not limited to, interferon-alpha, pegylated-interferon-alpha, interferon-beta, interferon-gamma, a cytokine, a vaccine, and a vaccine comprising an antigen and an adjuvant, and said second antiviral agent inhibits replication of HCV either by inhibiting host cellular functions associated with viral replication or by targeting proteins of the viral genome.

A further embodiment of the present invention is directed to a method of treating or preventing infection caused by an RNA-containing virus comprising co-administering to a patient in need of such treatment an agent or combination of agents that treat or alleviate symptoms of HCV infection including cirrhosis and inflammation of the liver, with a therapeutically effective amount of a compound or combination of compounds of the present invention, or a pharmaceutically acceptable salt thereof.

Yet another embodiment of the present invention provides a method of treating or preventing infection caused by an RNA-containing virus comprising co-administering to a patient in need of such treatment one or more agents that treat patients for disease caused by hepatitis B (HBV) infection, with a therapeutically effective amount of a compound or a combination of compounds of the present invention, or a pharmaceutically acceptable salt thereof. An agent that treats patients for disease caused by hepatitis B (HBV) infection may be for example, but not limited thereto, L-deoxythymidine, adefovir, lamivudine or tenofovir, or any combination thereof.

A further embodiment of the present invention provides a method of treating or preventing infection caused by an RNA-containing virus comprising co-administering to a patient in need of such treatment one or more agents that treat patients for disease caused by human immunodeficiency virus (HIV) infection, with a therapeutically effective amount of a compound or a combination of compounds of the present invention, or a pharmaceutically acceptable salt thereof. The agent that treats patients for disease caused by human immunodeficiency virus (HIV) infection may include, but is not limited thereto, ritonavir, lopinavir, indinavir, nelfmavir, saquinavir, amprenavir, atazanavir, tipranavir, TMC-114, fosamprenavir, zidovudine, lamivudine, didanosine, stavudine, tenofovir, zalcitabine, abacavir, efavirenz, nevirapine, delavirdine, TMC-125, L-870812, S-1360, enfuvirtide (T-20) or T-1249, or any combination thereof.

An example of the RNA-containing virus in any of the above embodiments includes, but not limited to, the hepatitis C virus (HCV).

It can occur that a patient may be co-infected with hepatitis C virus and one or more other viruses, including but not limited to human immunodeficiency virus (HIV), hepatitis A virus (HAV) and hepatitis B virus (HBV). Thus also contemplated is a combination therapy to treat such co-infections by co-administering a compound according to the present invention with at least one of an HIV inhibitor, an HAV inhibitor and an HBV inhibitor.

In addition, the present invention provides the use of a compound or a combination of compounds of the invention, or a therapeutically acceptable salt thereof, and one or more agents selected from the group consisting of a host immune modulator and a second or more antiviral agents, or a combination thereof, to prepare a medicament for the treatment of an infection caused by an RNA-containing virus in a patient, particularly hepatitis C virus. Examples of the host immune modulators include, but are not limited to, interferon-alpha, pegylated-interferon-alpha, interferon-beta, interferon-gamma, a cytokine, a vaccine, and a vaccine comprising an antigen and an adjuvant, and said second antiviral agent inhibits replication of HCV either by inhibiting host cellular functions associated with viral replication or by targeting proteins of the viral genome.

When used in the above or other treatments, combination of compound or compounds of the present invention, together with one or more agents as defined herein above, can be employed in pure form or, where such forms exist, in pharmaceutically acceptable salt thereof. Alternatively, such combination of therapeutic agents can be administered as a pharmaceutical composition containing a therapeutically effective amount of the compound or combination of compounds of interest, or their pharmaceutically acceptable salt thereof, in combination with one or more agents as defined hereinabove, and a pharmaceutically acceptable carrier. Such pharmaceutical compositions can be used for inhibiting the replication of an RNA-containing virus, particularly Hepatitis C virus (HCV), by contacting said virus with said pharmaceutical composition. In addition, such compositions are useful for the treatment or prevention of an infection caused by an RNA-containing virus, particularly Hepatitis C virus (HCV).

Hence, a still further embodiment of the invention is directed to a method of treating or preventing infection caused by an RNA-containing virus, particularly a hepatitis C virus (HCV), comprising administering to a patient in need of such treatment a pharmaceutical composition comprising a compound or combination of compounds of the invention or a pharmaceutically acceptable salt thereof, and one or more agents as defined hereinabove, with a pharmaceutically acceptable carrier.

When administered as a combination, the therapeutic agents can be formulated as separate compositions which are given at the same time or within a predetermined period of time, or the therapeutic agents can be given as a single unit dosage form. The therapeutic agents can be administered simultaneously, sequentially, or cyclically.

Antiviral agents contemplated for use in such combination therapy include agents (compounds or biologicals) that are effective to inhibit the formation and/or replication of a virus in a mammal, including but not limited to agents that interfere with either host or viral mechanisms necessary for the formation and/or replication of a virus in a mammal. Such agents can be selected from another anti-HCV agent; an HIV inhibitor; an HAV inhibitor; and an HBV inhibitor.

Other agents to be administered in combination with a compound of the present invention include a cytochrome P450 monooxygenase inhibitor, which is expected to inhibit metabolism of the compounds of the invention. Therefore, the cytochrome P450 monooxygenase inhibitor would be in an amount effective to inhibit metabolism of the compounds of the present invention. Accordingly, the CYP inhibitor is administered in an amount such that the bioavailability of the compounds of the present invention is increased in comparison to the bioavailability in the absence of the CYP inhibitor.

The term "room temperature" used in the specification denotes any temperature ranging between about 20° C. to about 40° C., except and otherwise it is specifically mentioned in the specification.

Unless mentioned otherwise, abbreviations used in description herein below have following meaning:

EDCl means 1-ethyl-3-(3-dimethylaminopropyl)-dicarbodiimide; HATU means 2-(7-aza-1H-benzotriazole-1-yl)-1,1,3,3-tetramethyluronium hexafluorophosphate; DIPEA means diisopropyl ethylamine; Boc means butoxycarbonyl; DMF means dimethylformamide; DMSO means dimethylsulfoxide; NBS means N-bromosuccinimide; NCS means N-chlorosuccinimide; NIS means N-iodosuccinimide; EtOAc means ethyl acetate; THF means tetrahydrofuran; Tf means triflate; DCM means dichloromethane; $Et_3N$ means triethylamine; MeOH means methanol; SEM means [2-(trimethylsilyl)ethoxy]methyl; EDC means ethylene dichloride; DIAD means diisopropyl azodicarboxylate; ACN means acetonitrile; Ts means tosyl, Ms means mesyl, RT means room temperature; Ac means acetyl; HPLC means high performance liquid chromatography, TLC means thin layer chromatography, PEG means polyethylene glycol; TFA means trifluoroacetic acid.

The following examples are provided to further illustrate the present invention and therefore should not be construed in any way to limit the scope of the present invention. All $^1H$ NMR spectra were obtained in the solvents indicated and chemical shifts are reported in δ units downfield from the internal standard tetramethylsilane (TMS) and inter proton coupling constants are reported in Hertz (Hz). In the case of mixture of isomers, the peak values given are for the dominant isomer (rotamer/tautomer).

EXAMPLE 1

Synthesis of dimethyl ((2S,2'S)-((2S,2'S)-2,2'-(5,5'-(7,8-dihydro-6H-dibenzo[f,h][1,5]dioxonine-3,11-diyl)bis(1H-imidazole-5,2-diyl))bis(pyrrolidine-2,1-diyl))bis(3-methyl-1-oxobutane-2,1-diyl)) dicarbamate (Compound 1)

Step 1: 1,1'-(7,8-dihydro-6H-dibenzo[f,h][1,5]dioxonine-3,11-diyl)diethanone (1a)

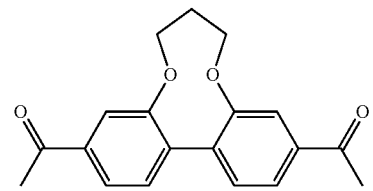 [SMILES: CC(=O)c1ccc2c(c1)OCCCOc1cc(C(C)=O)ccc1-2]

To a solution of 1,1'-(2,2'-dihydroxy-[1,1'-biphenyl]-4,4'-diyl)-diethanone (0.35 g, 1.29 mmol) (see, e.g., WO 2010/111673) in anhydrous DMF (10 mL) was added $K_2CO_3$ (0.47 g, 3.37 mmol) and the suspension was stirred at 90° C. for 30 min under nitrogen atmosphere, after which a solution of 1,3-dibromopropane (0.16 mL, 1.55 mmol) in DMF (1 mL) was added and stirring was continued for 18 h at 90° C. The reaction mixture was cooled to room temperature and crushed ice was added and stirred vigorously for 15 min. The contents of the reaction vessel were extracted with EtOAc and the organic phase was washed with brine, dried over sodium sulfate and purified by flash column chromatography (30% EtOAc-hexane) to yield a pale-yellow solid (1a) (0.29, 72%). m/z 311.1 (M+H)⁺.

¹H NMR (400 MHz, CDCl₃): δ 7.75-7.73 (m, 4H), 7.41-7.38 (m, 2H), 4.47-4.45 (m, 4H), 2.26 (s, 6H), 2.05-2.07 (m, 2H).

Step 2: 1,1'-(7,8-dihydro-6H-dibenzo[f,h][1,5]dioxonine-3,11-diyl)bis(2,2-dibromoethanone) (1b)

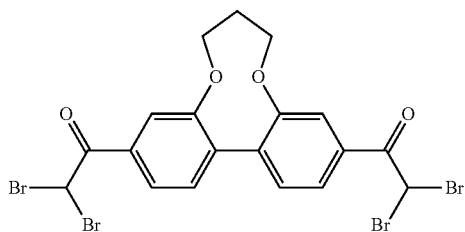 [SMILES: O=C(c1ccc2c(c1)OCCCOc1cc(C(=O)C(Br)Br)ccc1-2)C(Br)Br]

To a solution of 1,1'-(7,8-dihydro-6H-dibenzo[f,h][1,5]dioxonine-3,11-diyl)diethanone (1a) (0.29 g, 0.93 mmol) in CHCl₃ (10 mL) was added bromine (0.2 mL, 3.74 mmol) at 0° C. under a nitrogen atmosphere. The cooling bath was removed, the reaction mixture was warmed to room temperature and stirred for 2 h. Water was added to the reaction mixture and the organic contents were separated. The organic layer was washed with sodium bisulphate solution and brine, dried over sodium sulfate and evaporated under reduced pressure to yield a yellow coloured solid of 1b which was used in the next step without further purification (0.38 g, 87%). m/z 626.7 (M+).

¹H NMR (400 MHz, CDCl₃): δ 7.90-7.87 (m, 4H), 7.45-7.43 (m, 2H), 6.72 (s, 2H), 4.50-4.47 (m, 4H), 2.11-2.09 (m, 2H).

Step 3: 1,1'-(7,8-dihydro-6H-dibenzo[f,h][1,5]dioxonine-3,11-diyl)bis(2-bromoethanone) (1c)

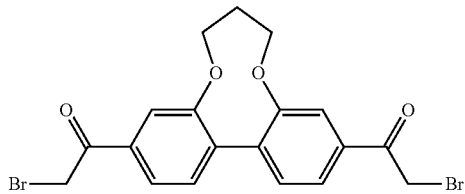 [SMILES: O=C(CBr)c1ccc2c(c1)OCCCOc1cc(C(=O)CBr)ccc1-2]

To a solution of 1,1'-(7,8-dihydro-6H-dibenzo[f,h][1,5]dioxonine-3,11-diyl)bis(2,2-dibromoethanone) (1b) (0.38 g, 0.61 mmol) in THF (7 mL) at 0° C. was added Et₃N (0.09 mL, 0.61 mmol) and diethyl phosphite (0.24 mL, 1.82 mmol). The reaction mixture was gradually warmed to room temperature, stirred for 1 h and concentrated under reduced pressure. The residual contents were partitioned between EtOAc and water. The organic layer was washed with brine, dried over sodium sulfate and concentrated under reduced pressure to yield an yellow oil (1c) which was used in the next step without further purification (0.15 g, 53%). m/z 468.9 (M+).

¹H NMR (400 MHz, CDCl₃): δ 7.78-7.76 (m, 4H), 7.44-7.42 (m, 2H), 4.49-4.46 (m, 8H), 2.11-2.06 (m, 2H).

Step 4: Synthesis of (2S,2'S)-1-di-tert-butyl O'²,O²-((7,8-dihydro-6H-dibenzo[f,h][1,5]dioxonine-3,11-diyl)bis(2-oxoethane-2,1-diyl))bis(pyrrolidine-1,2-dicarboxylate) (1d)

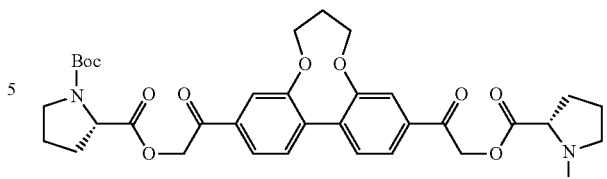

To a solution of 1,1'-(7,8-dihydro-6H-dibenzo[f,h][1,5]dioxonine-3,11-diyl)bis(2-bromoethanone) (1c) (0.15 g, 0.32 mmol) in acetonitrile (3 mL) DIPEA (0.06 mL, 0.32 mmol) was added. The reaction mixture was stirred at room temperature for 5 min. after which (S)-1-(tert-butoxycarbonyl)-pyrrolidine-2-carboxylic acid (0.15 g, 0.67 mmol) was added. The reaction mixture was stirred at room temperature for 3 h after which water was added. The organic contents were washed with brine, dried over sodium sulfate and concentrated under reduced pressure to yield a yellow foam (1d) that was used in the next step without further purification (0.22 g, 93%). m/z 637.3 [(M+H)⁺−100] (Boc cleavage).

¹H NMR (400 MHz, CDCl₃): δ 7.70-7.65 (m, 4H), 7.42-7.39 (m, 2H), 5.43-5.31 (m, 4H), 4.50-4.44 (m, 4H), 3.64-3.53 (m, 2H), 3.49-3.41 (m, 2H), 2.38-2.32 (m, 4H), 2.12-2.02 (m, 4H), 1.99-1.93 (m, 4H), 1.51-1.39 (m, 18H).

Step 5: Synthesis of (2S,2'S)-di-tert-butyl 2,2'-(5,5'-(7,8-dihydro-6H-dibenzo[f,h][1,5]dioxonine-3,11-diyl)bis(1H-imidazole-5,2-diyl))bis(pyrrolidine-1-carboxylate) (1e)

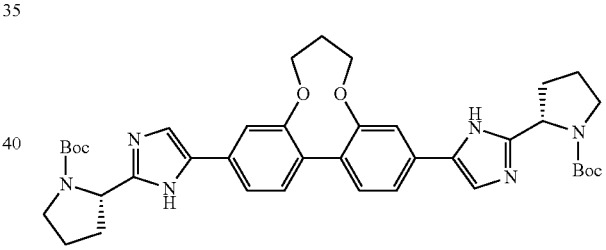

To a 25 mL sealed tube, (2S,2'S)-1-di-tert-butyl O'²,O²-((7,8-dihydro-6H-dibenzo[f,h][1,5]dioxonine-3,11-diyl)bis(2-oxoethane-2,1-diyl))bis(pyrrolidine-1,2-dicarboxylate) (1d) (0.22 g, 0.30 mmol) was added in toluene (10 mL). Ammonium acetate (0.46 g, 5.97 mmol) was added thereafter. The mixture was heated at 115° C. for 18 h. The reaction mixture was evaporated under reduced pressure followed by addition of water. The aqueous content was extracted with EtOAc. The organic layer was washed with brine, dried over sodium sulfate and purified by flash column chromatography (4% MeOH-DCM) to yield an off-white foam (1e) (0.12 g, 58%). m/z 697.4 (M+H)⁺.

¹H NMR (400 MHz, CDCl₃): δ 7.77-7.28 (m, 6H), 7.25 (s, 2H), 4.45 (m, 4H), 3.43 (m, 4H), 2.19 (m, 4H), 2.10-1.99 (m, 8H), 1.52-1.46 (m, 18H).

Step 6: dimethyl ((2S,2'S)-((2S,2'S)-2,2'-(5,5'-(7,8-dihydro-6H-dibenzo[f,h][1,5]dioxonine-3,11-diyl)bis(1H-imidazole-5,2-diyl))bis(pyrrolidine-2,1-diyl))bis(3-methyl-1-oxobutane-2,1-diyl))dicarbamate (Compound 1)

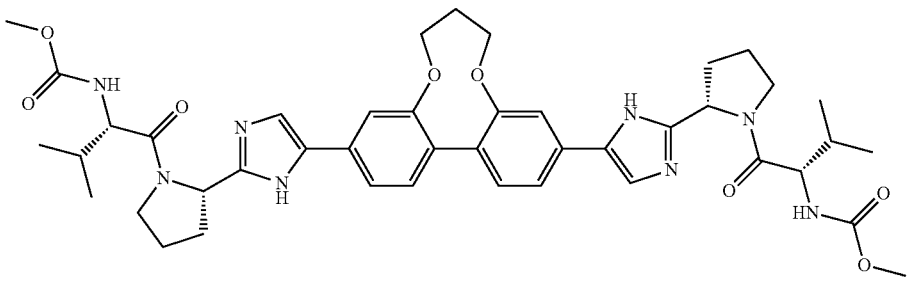

To a solution of (2S,2'S)-di-tert-butyl 2,2'-(5,5'-(7,8-dihydro-6H-dibenzo[f,h][1,5]dioxonine-3,11-diyl)bis(1H-imidazole-5,2-diyl))bis(pyrrolidine-1-carboxylate) (1e) (0.09 g, 0.12 mmol) in DCM at 0° C., trifluoroacetic acid (0.05 mL, 0.62 mmol) was added. The reaction mixture was warmed to 25° C. and stirred for 2 h. The reaction mixture was concentrated under reduced pressure. The content was taken up in DMF (2 mL) and cooled to 0° C., after which DIPEA (0.09 mL, 0.49 mmol) was added and the reaction mixture was stirred for 10 min. (S)-2-((methoxycarbonyl)-amino)-3-methylbutanoic acid (0.04 g, 0.25 mmol) and HATU (0.09 g, 0.25 mmol) were added to the reaction mixture at 0° C. The reaction mixture was gradually warmed to 25° C. and stirred for 18 h. Crushed ice was added to the reaction mixture and the precipitate was filtered. Purification by preparative HPLC yielded an off-white solid (0.04 g, 40%). m/z 811.5 (M+H)$^+$.

$^1$H NMR (400 MHz, CDCl$_3$): δ 7.59-7.48 (m, 4H), 7.35-7.28 (m, 4H), 5.44 (d, J=8.8 Hz, 2H), 5.32-5.28 (m, 2H), 4.44-4.33 (m, 2H), 3.86-3.76 (m, 2H), 3.72 (s, 6H), 3.67-3.64 (m, 3H), 3.12-2.97 (m, 3H), 2.37 (m, 2H), 2.37-2.16 (m, 2H), 2.12-1.97 (m, 8H), 1.12-0.81 (m, 12H).

EXAMPLE 2

Synthesis of methyl ((S)-1-((S)-2-(5-(11-(2-((S)-1-((S)-2-(methoxycarbonyl)amino-3-methylbutanoyl)pyrrolidin-2-yl)-1H-imidazol-5-yl)-7,8-dihydro-6H-dibenzo[f,h][1,5]dioxonin-3-yl)-4-chloro-1H-imidazol-2-yl)pyrrolidin-1-yl)-3-methyl-1-oxobutan-2-yl)carbamate (Compound 2)

Step 1: (S)-tert-butyl 2-(5-(11-(2-((S)-1-(tert-butoxycarbonyl)pyrrolidin-2-yl)-1H-imidazol-5-yl)-7,8-dihydro-6H-dibenzo[f,h][1,5]dioxonin-3-yl)-4-chloro-1H-imidazol-2-yl)pyrrolidine-1-carboxylate (2a)

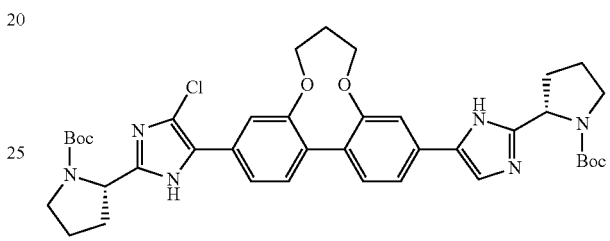

To a solution of (2S,2'S)-di-tert-butyl 2,2'-(5,5'-(7,8-dihydro-6H-dibenzo[f,h][1,5]dioxonine-3,11-diyl)bis(1H-imidazole-5,2-diyl))bis(pyrrolidine-1-carboxylate) (1e), (0.30 g, 0.43 mmol) in DMF (3 ml) was added NCS (0.12 g, 0.86 mmol) and the mixture was heated at 45° C. for 90 min after which the contents were added to water. The aqueous contents were extracted with EtOAc and the organic layer was washed with brine. The organic layer was dried over sodium sulphate and purified by flash chromatography (30% EtOAc-hexane) to yield an off-white foam of (S)-tert-butyl 2-(5-(11-(2-((S)-1-(tert-butoxycarbonyl)pyrrolidin-2-yl)-1H-imidazol-5-yl)-7,8-dihydro-6H-dibenzo[f,h][1,5]dioxonin-3-yl)-4-chloro-1H-imidazol-2-yl)pyrrolidine-1-carboxylate (2a) (0.05 g). m/z 731.4 (M+H)$^+$.

$^1$H-NMR (400 MHz, CDCl$_3$): δ 7.45-7.44 (m, 2H), 7.35-7.34 (m, 4H), 7.25 (s, 1H), 4.97-4.96 (m, 2H), 4.43-4.42 (m, 4H), 3.50-3.43 (m, 4H), 2.91-2.90 (m, 2H), 2.19-1.98 (m, 8H), 1.52-1.46 (m, 18H).

Step 2: methyl ((S)-1-((S)-2-(5-(11-(2-((S)-1-((S)-2-(methoxycarbonyl)amino-3-methylbutanoyl)pyrrolidin-2-yl)-1H-

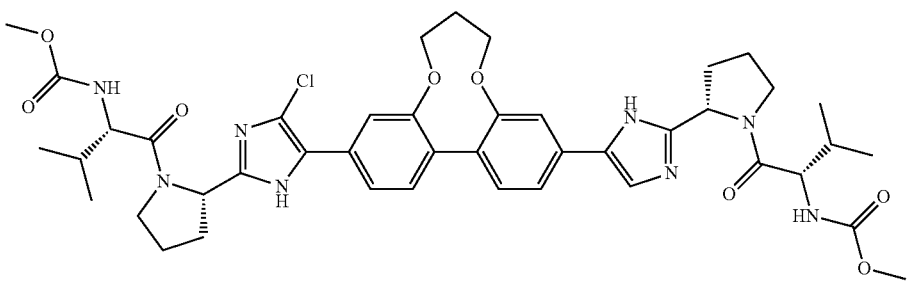

imidazol-5-yl)-7,8-dihydro-6H-dibenzo[f,h][1,5]dioxonin-3-yl)-4-chloro-1H-imidazol-2-yl)pyrrolidin-1-yl)-3-methyl-1-oxobutan-2-yl)carbamate (2b)

Step 1: (2S,2'S)-di-tert-butyl 2,2'-(5,5'-(7,8-dihydro-6H-dibenzo[f,h][1,5]dioxonine-3,11-diyl)bis(4-chloro-1H-imidazole-5,2-diyl))bis(pyrrolidine-1-carboxylate) (3a)

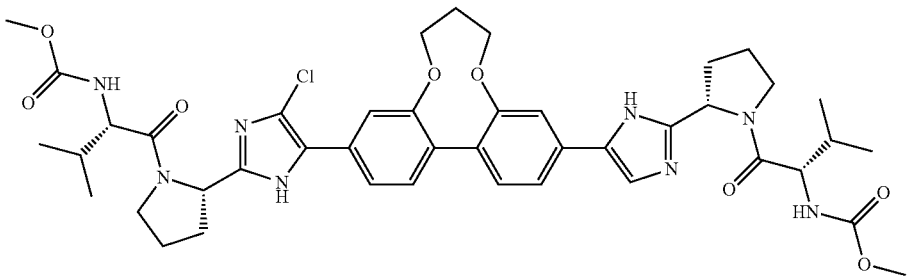

To a solution of (S)-tert-butyl 2-(5-(11-(2-((S)-1-(tert-butoxycarbonyl)pyrrolidin-2-yl)-1H-imidazol-5-yl)-7,8-dihydro-6H-dibenzo[f,h][1,5]dioxonin-3-yl)-4-chloro-1H-imidazol-2-yl)pyrrolidine-1-carboxylate (2a, 0.05 g, 0.07 mmol) at 0° C. in DCM (1 ml) was added trifluoroacetic acid (0.17 g, 1.50 mmol). The reaction mixture was warmed to 25° C. and stirred for 2 hours after which all the volatiles were removed under reduced pressure. The contents were taken up in ACN (8 ml) and cooled to 0° C. after which diisopropylethyl amine (DIPEA) (0.06 g, 0.45 mmol), 1H-benzo-[d][1,2,3]-triazol-1-ol hydrate (0.03 g, 0.19 mmol) and EDCl (0.04 g, 0.19 mmol) were added. The reaction mixture was stirred for 10 minutes after which (S)-2-((methoxycarbonyl)-amino)-3-methylbutanoic acid (0.03 g, 0.19 mmol) was added. The reaction mixture was gradually warmed to 25° C. and stirred for 18 hr. The reaction mixture was evaporated to dryness followed by addition of crushed ice to precipitate solid product. The solid product was filtered and purified by preparative HPLC yielded an off-white solid (0.04 g, 40%) of methyl ((S)-1-((S)-2-(5-(11-(2-((S)-1-((S)-2-(methoxycarbonyl)amino-3-methylbutanoyl)pyrrolidin-2-yl)-1H-imidazol-5-yl)-7,8-dihydro-6H-dibenzo[f,h][1,5]dioxonin-3-yl)-4-chloro-1H-imidazol-2-yl)pyrrolidin-1-yl)-3-methyl-1-oxobutan-2-yl)carbamate. m/z 845.4 (M$^+$+1); $^1$H-NMR (400 MHz, CDCl$_3$) δ (ppm): 7.67-7.20 (m, 7H), 5.26-5.43 (m, 2H), 4.42-4.27 (m, 6H), 3.85-3.58 (m, 10H), 3.14-2.97 (m, 2H), 2.37 (br m, 2H), 2.12-1.97 (m, 8H), 1.12-0.81 (m, 12H).

EXAMPLE 3 dimethyl ((2S,2'S)-((2S,2'S)-2,2'-(5,5'-(7,8-dihydro-6H-dibenzo[f,h][1,5]dioxonine-3,11-diyl)bis(4-chloro-1H-imidazole-5,2-diyl))bis(pyrrolidine-2,1-diyl))bis(3-methyl-1-oxobutane-2,1-diyl))dicarbamate (Compound 3)

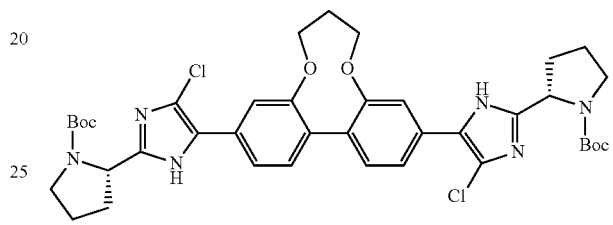

To a solution of (2S,2'S)-di-tert-butyl 2,2'-(5,5'-(7,8-dihydro-6H-dibenzo[f,h][1,5]dioxonine-3,11-diyl)bis(1H-imidazole-5,2-diyl))bis(pyrrolidine-1-carboxylate) (1e), (0.30 g, 0.43 mmol) in DMF (3 ml) was added NCS (0.12 g, 0.86 mmol) and the mixture was heated at 45° C. for 90 min after which the contents were added to water. The aqueous contents were extracted with EtOAc and the organic layer was washed with brine. The organic layer was dried over sodium sulphate and purified by flash chromatography (30% EtOAc-hexane) to yield off-white foam of (2S,2'S)-di-tert-butyl 2,2'-(5,5'-(7,8-dihydro-6H-dibenzo[f,h][1,5]dioxonine-3,11-diyl)bis(4-chloro-1H-imidazole-5,2-diyl))bis(pyrrolidine-1-carboxylate) (3a) (0.12 g). m/z 765.4 (M+H)$^+$.

$^1$H-NMR (400 MHz, CDCl$_3$): δ 7.45 (m, 2H), 7.35 (m, 4H), 4.97-4.96 (m, 2H), 4.45-4.42 (m, 4H), 3.44-3.38 (m, 4H), 2.94-2.90 (m, 2H), 2.20-1.98 (m, 8H), 1.52-1.46 (m, 18H).

Step 2: dimethyl ((2S,2'S)-((2S,2'S)-2,2'-(5,5'-(7,8-dihydro-6H-dibenzo[f,h][1,5]dioxonine-3,11-diyl)bis(4-chloro-1H-imidazole-5,2-diyl))bis(pyrrolidine-2,1-diyl))bis(3-methyl-1-oxobutane-2,1-diyl))dicarbamate (3b)

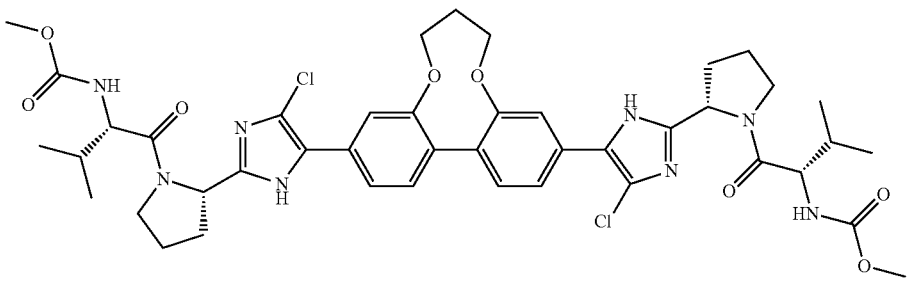

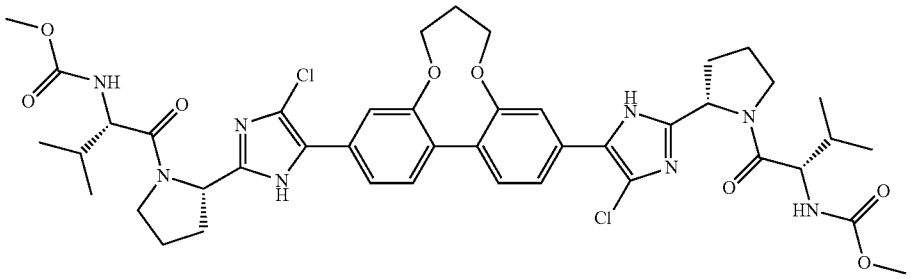

To a solution of (2S,2'S)-di-tert-butyl 2,2'-(5,5'-(7,8-dihydro-6H-dibenzo[f,h][1,5]dioxonine-3,11-diyl)bis(4-chloro-1H-imidazole-5,2-diyl))bis(pyrrolidine-1-carboxylate) (3a, 0.11 g, 0.14 mmol) in DCM (1 ml) at 0° C. was added trifluoroacetic acid (0.33 g, 2.87 mmol). The reaction mixture was warmed to 25° C. and stirred for 2 hour after which all the volatiles were removed under reduced pressure. The contents were taken up in ACN (10 ml) and cooled to 0° C. after which diisopropylethyl amine (DIPEA) (0.11 g, 0.86 mmol), 1H-benzo-[d][1,2,3]-triazol-1-ol hydrate (0.06 g, 0.36 mmol) and EDCl (0.07 g, 0.36 mmol) were added. The reaction mixture was stirred for 10 minutes after which (S)-2-((methoxycarbonyl)-amino)-3-methylbutanoic acid (0.06 g, 0.36 mmol) was added. The reaction mixture was gradually warmed to 25° C. and stirred for 18 hr. The reaction mixture was evaporated to dryness followed by addition of crushed ice to precipitate solid product. The precipitated product was filtered and purified by preparative HPLC yielded an off-white solid (0.04 g, 40%) of dimethyl ((2S,2'S)-((2S,2'S)-2,2'-(5,5'-(7,8-dihydro-6H-dibenzo[f,h][1,5]dioxonine-3,11-diyl)bis(4-chloro-1H-imidazole-5,2-diyl))bis(pyrrolidine-2,1-diyl))bis(3-methyl-1-oxobutane-2,1-diyl))dicarbamate. m/z 879.5 (M$^+$+1); $^1$H-NMR (400 MHz, DMSO-d$_6$) δ (ppm: 7.47-7.46 (m, 4H), 7.32-7.36 (m, 4H), 4.99-5.01 (m, 2H), 4.37 (m, 4H), 4.03-4.07 (m, 2H), 3.78-3.80 (m, 4H), 3.53 (s, 6H), 1.91-2.18 (m, 12H), 0.81-1.12 (m, 12H).

EXAMPLE 4

Synthesis of dimethyl ((2S,2'S)-((2S,2'S)-2,2'-(5,5'-(6,7,8,9-tetrahydrodibenzo[b,d][1,6]dioxecine-3,12-diyl)bis(1H-imidazole-5,2-diyl))bis(pyrrolidine-2,1-diyl))bis(3-methyl-1-oxobutane-2,1-diyl)) dicarbamate (Compound 4)

Step 1: 1,1'-(6,7,8,9-tetrahydrodibenzo[b,d][1,6]dioxecine-3,12-diyl)diethanone (4a)

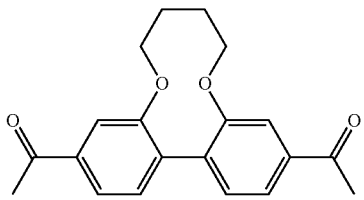 [SMILES: CC(=O)c1ccc2c(c1)OCCCCOc1cc(C(C)=O)ccc1-2]

was synthesized from 1,1'-(2,2'-dihydroxy-[1,1'-biphenyl]-4,4'-diyl)-diethanone and 1,4-dibromobutane by following an analogous procedure described in Step 1, Example 1. m/z 325.2 (M+H)$^+$.

$^1$H NMR (400 MHz, CDCl$_3$): δ 7.68-7.61 (m, 4H), 7.46-7.37 (m, 2H), 4.27 (t, J=9.6 Hz, 4H), 2.65 (s, 6H), 2.00-1.86 (m, 4H).

Step 2: 1,1'-(6,7,8,9-tetrahydrodibenzo[b,d][1,6]dioxecine-3,12-diyl)bis(2,2-dibromoethanone) (4b)

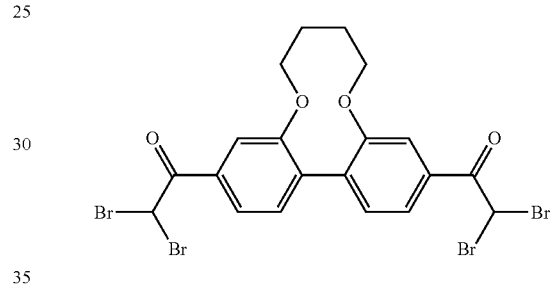

was synthesized from 1,1'-(6,7,8,9-tetrahydrodibenzo[b,d][1,6]dioxecine-3,12-diyl)diethanone and bromine by following an analogous procedure described in Step 2, Example 1. m/z 640.7 (M+H)$^+$.

$^1$H NMR (400 MHz, CDCl$_3$): δ 7.82-7.79 (m, 4H), 7.46-7.41 (m, 2H), 6.72 (s, 2H), 4.26 (t, J=9.6 Hz, 4H), 2.06-1.92 (m, 4H).

Step 3: 1,1'-(6,7,8,9-tetrahydrodibenzo[b,d][1,6]dioxecine-3,12-diyl)bis(2-bromoethanone) (4c)

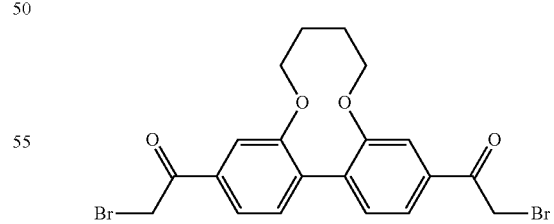

was synthesized from 1,1'-(6,7,8,9-tetrahydrodibenzo[b,d][1,6]dioxecine-3,12-diyl)bis(2,2-dibromoethanone) by following an analogous procedure described in Step 3, Example 1.

$^1$H NMR (400 MHz, CDCl$_3$): δ 7.71-7.63 (m, 4H), 7.45-7.40 (m, 2H), 4.74-4.57 (m, 2H), 4.31-4.27 (m, 4H), 2.06-1.89 (m, 4H).

Step 4: (2S,2'S)-1-di-tert-butyl O'²,O²-((6,7,8,9-tetrahydrodibenzo[b,d][1,6]dioxecine-3,12-diyl)bis(2-oxoethane-2,1-diyl)) bis(pyrrolidine-1,2-dicarboxylate) (4d)

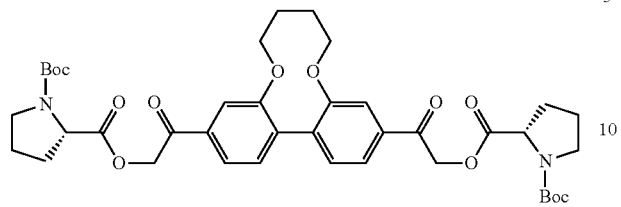

was synthesized from 1,1'-(6,7,8,9-tetrahydrodibenzo[b,d][1,6]dioxecine-3,12-diyl)bis(2-bromoethanone) and (S)-1-(tert-butoxycarbonyl)-pyrrolidine-2-carboxylic acid by following an analogous procedure described in Step 4, Example 1. m/z 651.2 [(M+H)⁺−100] (Boc cleavage).

¹H NMR (400 MHz, CDCl₃): δ 7.70-7.28 (m, 6H), 5.56-5.33 (m, 4H), 4.53-4.10 (m, 6H), 3.59-3.35 (m, 4H), 2.36-2.26 (m, 3H), 2.11-2.00 (m, 4H), 1.99-1.89 (m, 5H), 1.69-1.49 (m, 18H).

Step 5: (2S,2'S)-di-tert-butyl 2,2'-(5,5'-(6,7,8,9-tetrahydrodibenzo[b,d][1,6]dioxecine-3,12-diyl)bis(1H-imidazole-5,2-diyl))bis(pyrrolidine-1-carboxylate) (4e)

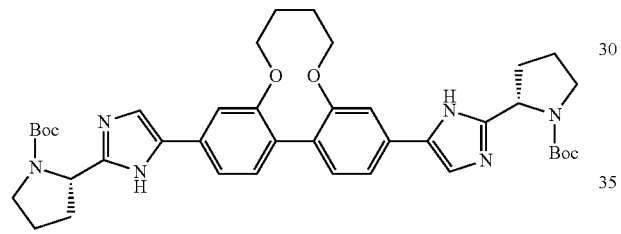

was synthesized from (2S,2'S)-1-di-tert-butyl O'²,O²-((6,7,8,9-tetrahydrodibenzo[b,d][1,6]dioxecine-3,12-diyl)bis(2-oxoethane-2,1-diyl)) bis(pyrrolidine-1,2-dicarboxylate) by following an analogous procedure described in Step 5, Example 1. m/z 711.3 (M+H)⁺.

¹H NMR (400 MHz, CDCl₃): δ 7.85-7.30 (m, 6H), 7.24 (s, 2H), 4.56-4.54 (m, 2H), 4.37-4.25 (m, 3H), 3.56-3.36 (m, 4H), 2.26-2.18 (m, 4H), 2.04-1.90 (m, 9H), 1.52-1.27 (m, 18H).

Step 6: dimethyl ((2S,2'S)-((2S,2'S)-2,2'-(5,5'-(6,7,8,9-tetrahydrodibenzo[b,d][1,6]dioxecine-3,12-diyl)bis(1H-imidazole-5,2-diyl))bis(pyrrolidine-2,1-diyl))bis(3-methyl-1-oxobutane-2,1-diyl))dicarbamate (Compound 4)

was synthesized from (2S,2'S)-di-tert-butyl 2,2'-(5,5'-(6,7,8,9-tetrahydrodibenzo[b,d][1,6]dioxecine-3,12-diyl)bis(1H-imidazole-5,2-diyl))bis(pyrrolidine-1-carboxylate) and (S)-2-((methoxycarbonyl)-amino)-3-methylbutanoic acid by following an analogous procedure described in Step 6, Example 1. m/z 825.4 (M+H)⁺.

¹H NMR (400 MHz, CDCl₃): δ 7.70-7.30 (m, 6H), 7.22 (s, 2H), 5.47 (d, J=9.2 Hz, 2H), 4.54-4.53 (m, 2H), 4.37-4.28 (m, 4H), 3.88-3.72 (m, 2H), 3.68 (s, 6H), 3.67-3.61 (m, 2H), 2.36-2.30 (m, 2H), 2.25-2.09 (m, 6H), 2.04-1.70 (m, 8H), 1.14-0.88 (m, 12H).

EXAMPLE 5

Synthesis of dimethyl ((2S,2'S)-((2S,2'S)-2,2'-(5,5'-(7,7-dimethyl-7,8-dihydro-6H-dibenzo[f,h][1,5]dioxonine-3,11-diyl)bis(1H-imidazole-5,2-diyl))bis(pyrrolidine-2,1-diyl))bis(3-methyl-1-oxobutane-2,1-diyl))dicarbamate (Compound 5)

Step 1: 1,1'-(7,7-dimethyl-7,8-dihydro-6H-dibenzo[f,h][1,5]dioxonine-3,11-diyl)diethanone (5a)

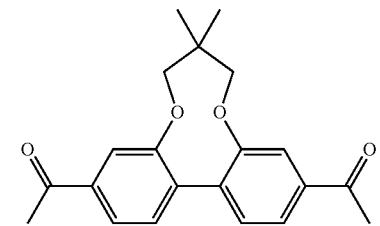

To a solution of 1,1'-(2,2'-dihydroxy-[1,1'-biphenyl]-4,4'-diyl)-diethanone (0.2 g, 0.74 mmol) (synthesized according to WO 2010/111673) in anhydrous DMF (10 mL), NaOH (0.08 g, 1.85 mmol) and 2,2-dimethylpropane-1,3-diyl-bis-(4-methylbenzenesulfonate) (0.37 g, 0.89 mmol) (synthesized according to US 2005/0113374) were added successively and the suspension was stirred at 150° C. for 20 h under nitrogen atmosphere. The reaction mixture was brought to room temperature, crushed ice was added and stirred vigorously for 15 min. The contents were extracted with ethyl acetate. The organic layer was washed with brine, dried over sodium sulfate and purified by flash column chromatography (20% Ethyl acetate-Hexane) to yield a white solid (0.08 g, 32%). m/z 339.3 (M+H)⁺.

¹H NMR (400 MHz, CDCl₃): δ 7.75-7.70 (m, 4H), 7.41-7.39 (d, J=8 Hz, 2H), 4.32-4.30 (d, J=11 Hz, 2H), 4.08-4.06 (d, J=11 Hz, 2H), 2.65 (s, 6H), 0.89 (s, 6H).

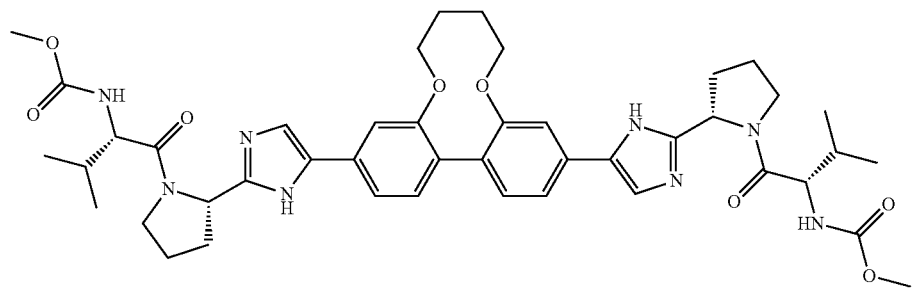

Step 2: 1,1'-(7,7-dimethyl-7,8-dihydro-6H-dibenzo[f,h][1,5]dioxonine-3,11-diyl)bis(2,2-dibromoethanone) (5b)

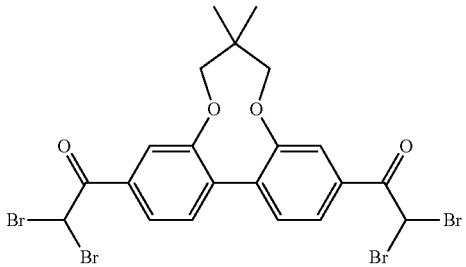 [SMILES: CC1(C)COc2cc(C(=O)C(Br)Br)ccc2-c2ccc(C(=O)C(Br)Br)cc2OC1]

was synthesized from 1,1'-(7,7-dimethyl-7,8-dihydro-6H-dibenzo[f,h][1,5]dioxonine-3,11-diyl)diethanone and bromine by following an analogous procedure described in Step 2, Example 1.

$^1$H NMR (400 MHz, CDCl$_3$): δ 7.88-7.84 (m, 4H), 7.45-7.43 (d, J=8 Hz, 2H), 6.70 (s, 2H), 4.49-4.30 (m, 4H), 0.96 (s, 6H).

Step 3: 1,1'-(7,7-dimethyl-7,8-dihydro-6H-dibenzo[f,h][1,5]dioxonine-3,11-diyl)bis(2-bromoethanone) (5c)

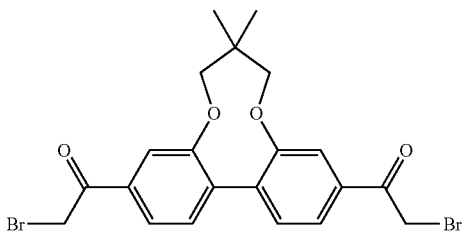 [SMILES: CC1(C)COc2cc(C(=O)CBr)ccc2-c2ccc(C(=O)CBr)cc2OC1]

was synthesized from 1,1'-(7,7-dimethyl-7,8-dihydro-6H-dibenzo[f,h][1,5]dioxonine-3,11-diyl)bis(2,2-dibromoethanone) by following an analogous procedure described in Step 3, Example 1. m/z 494.9 (M+H)$^+$.

$^1$H NMR (400 MHz, CDCl$_3$): δ 7.80-7.73 (m, 4H), 7.44-7.42 (d, J=8 Hz, 2H), 4.49-4.25 (m, 8H), 0.95 (s, 6H).

Step 4: Synthesis of ((2S,2'S)-1-di-tert-butyl O'$^2$,O$^2$-((7,7-dimethyl-7,8-dihydro-6H-dibenzo[f,h][1,5]dioxonine-3,11-diyl)bis(2-oxoethane-2,1-diyl)) bis(pyrrolidine-1,2-dicarboxylate) (5d)

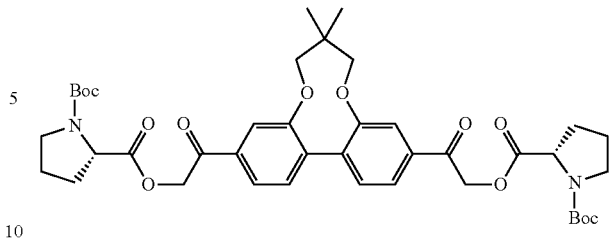

The above compound was synthesized from 1,1'-(7,7-dimethyl-7,8-dihydro-6H-dibenzo[f,h][1,5]dioxonine-3,11-diyl)bis(2-bromoethanone) and (S)-1-(tert-butoxycarbonyl)-pyrrolidine-2-carboxylic acid by following an analogous procedure described in Step 4, Example 1.

$^1$H NMR (400 MHz, CDCl$_3$): δ 7.70-7.63 (m, 4H), 7.42-7.40 (d, J=8 Hz, 2H), 5.55-5.25 (m, 4H), 4.50-4.30 (m, 4H), 3.60-3.40 (m, 6H), 2.30-1.95 (m, 8H), 1.51-1.39 (m, 18H), 0.95 (s, 6H).

Step 5: (2S,2'S)-di-tert-butyl 2,2'-(5,5'-(7,7-dimethyl-7,8-dihydro-6H-dibenzo[f,h][1,5]dioxonine-3,11-diyl)bis(1H-imidazole-5,2-diyl))bis(pyrrolidine-1-carboxylate) (5e)

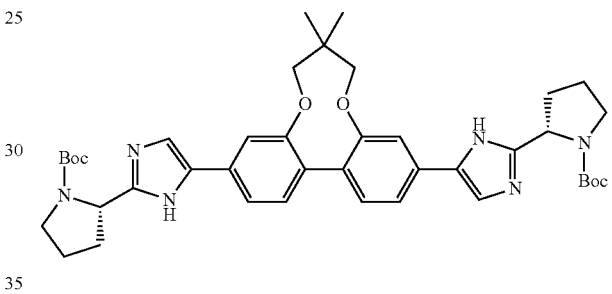

was synthesized from ((2S,2'S)-1-di-tert-butyl O'$^2$,O$^2$-((7,7-dimethyl-7,8-dihydro-6H-dibenzo[f,h][1,5]dioxonine-3,11-diyl)bis(2-oxo ethane-2,1-diyl)) bis(pyrrolidine-1,2-dicarboxylate) by following an analogous procedure described in Step 5, Example 1. m/z 725 (M+H)$^+$.

$^1$H NMR (400 MHz, CDCl$_3$): 7.32-7.28 (m, 6H), 7.25 (s, 2H), 5.09-5.01 (m, 2H), 4.24-4.11 (m, 4H), 3.44-3.40 (m, 4H), 2.19-2.10 (m, 8H), 1.52-1.46 (m, 18H), 0.95 (s, 6H).

Step 6: Synthesis of dimethyl ((2S,2'S)-((2S,2'S)-2,2'-(5,5'-(7,7-dimethyl-7,8-dihydro-6H-dibenzo[f,h][1,5]dioxonine-3,11-diyl)bis(1H-imidazole-5,2-diyl))bis(pyrrolidine-2,1-diyl))bis(3-methyl-1-oxobutane-2,1-diyl))dicarbamate (Compound 5)

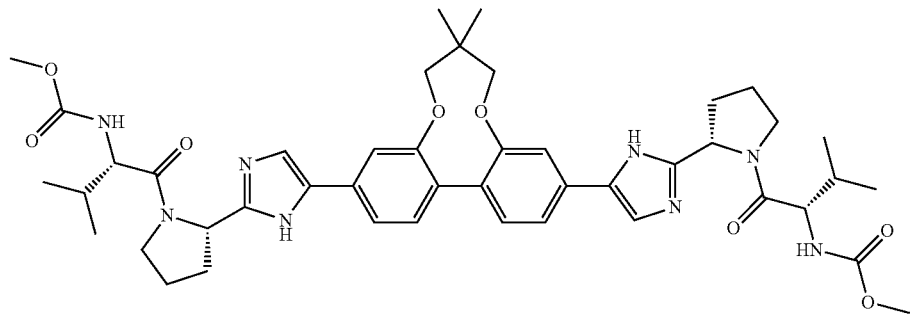

The above compound was synthesized from (2S,2'S)-di-tert-butyl 2,2'-(5,5'-(7,7-dimethyl-7,8-dihydro-6H-dibenzo[f,h][1,5]dioxonine-3,11-diyl)bis(1H-imidazole-5,2-diyl))bis(pyrrolidine-1-carboxylate) and (S)-2-((methoxycarbonyl)-amino)-3-methylbutanoic acid by following an analogous procedure described in Step 6, Example 1. m/z 839.4 (M+H)+.

$^1$H NMR (400 MHz, DMSO-$d_6$): δ 7.52-7.51 (m, 4H), 7.42-7.40 (m, 2H), 7.34-7.31 (m, 2H), 7.18-7.14 (m, 2H), 5.08-5.06 (m, 2H), 4.35-4.05 (m, 6H), 3.90-3.80 (m, 4H), 3.72 (s, 6H), 2.37-2.33 (m, 2H), 2.12-1.97 (m, 8H), 1.12-0.81 (m, 18H).

EXAMPLE 6

Synthesis of methyl ((S)-1-((S)-2-(5-(11-(2-((S)-1-((S)-2-(methoxycarbonyl)amino-3-methylbutanoyl)pyrrolidin-2-yl)-4-chloro-1H-imidazol-5-yl)-7,7-dimethyl-7,8-dihydro-6H-dibenzo[f,h][1,5]dioxonin-3-yl)-1H-imidazol-2-yl)pyrrolidin-1-yl)-3-methyl-1-oxobutan-2-yl)carbamate (Compound 6)

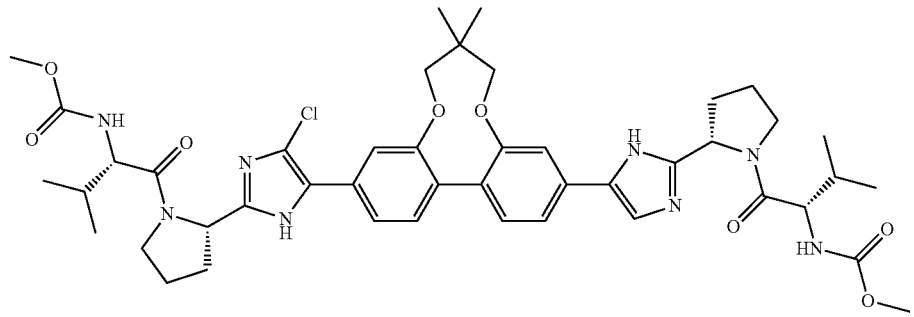

The above compound was synthesized from dimethyl ((2S,2'S)-((2S,2'S)-2,2'-(5,5'-(7,7-dimethyl-7,8-dihydro-6H-dibenzo[f,h][1,5]dioxonine-3,11-diyl)bis(1H-imidazole-5,2-diyl))bis(pyrrolidine-2,1-diyl))bis(3-methyl-1-oxobutane-2,1-diyl))dicarbamate (Compound 5)) and NCS by following an analogous procedure described in Step 1, Example 2 to yield methyl ((S)-1-((S)-2-(5-(11-(2-((S)-1-((S)-2-(methoxycarbonyl)amino-3-methylbutanoyl)pyrrolidin-2-yl)-4-chloro-1H-imidazol-5-yl)-7,7-dimethyl-7,8-dihydro-6H-dibenzo[f,h][1,5]dioxonin-3-yl)-1H-imidazol-2-yl)pyrrolidin-1-yl)-3-methyl-1-oxobutan-2-yl)carbamate. m/z 873.4 (M+H)+.

$^1$H NMR (400 MHz, CDCl$_3$): δ 10.80 (br s, 1H), 10.40 (br s, 1H), 7.50-7.45 (m, 2H), 7.40-7.20 (m, 5H), 5.50-5.45 (m, 2H), 5.30-5.20 (m, 2H), 4.45-4.05 (m, 6H), 3.90-3.80 (m, 2H), 3.75 (s, 6H), 3.70-3.60 (m, 2H), 3.02-2.90 (m, 2H), 2.40-1.90 (m, 8H), 1.12-0.81 (m, 18H).

EXAMPLE 7

Synthesis of dimethyl ((2S,2'S)-((2S,2'S)-2,2'-(5,5'-(7,7-dimethyl-7,8-dihydro-6H-dibenzo[f,h][1,5]dioxonine-3,11-diyl)bis(4-chloro-1H-imidazole-5,2-diyl))bis(pyrrolidine-2,1-diyl))bis(3-methyl-1-oxobutane-2,1-diyl))dicarbamate (Compound 7)

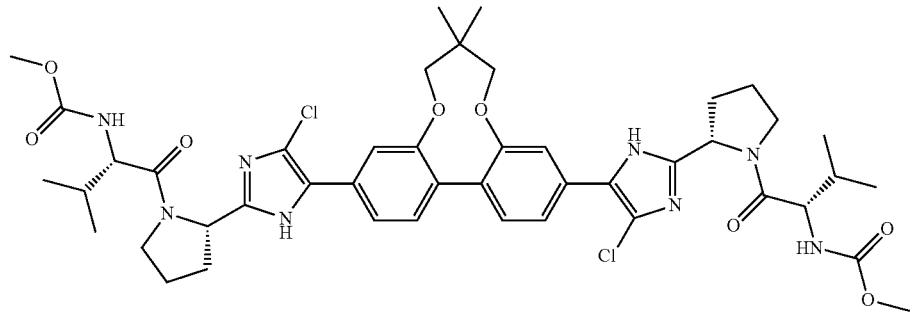

The above compound was synthesized from dimethyl ((2S,2'S)-((2S,2'S)-2,2'-(5,5'-(7,7-dimethyl-7,8-dihydro-6H-dibenzo[f,h][1,5]dioxonine-3,11-diyl)bis(1H-imidazole-5,2-diyl))bis(pyrrolidine-2,1-diyl))bis(3-methyl-1-oxobutane-2,1-diyl))dicarbamate (Compound 5) and NCS by following an analogous procedure described in Step 1, Example 3 to yield dimethyl ((2S,2'S)-((2S,2'S)-2,2'-(5,5'-(7,7-dimethyl-7,8-dihydro-6H-dibenzo[f,h][1,5]dioxonine-3,11-diyl)bis(4-chloro-1H-imidazole-5,2-diyl))bis(pyrrolidine-2,1-diyl))bis(3-methyl-1-oxobutane-2,1-diyl))dicarbamate. m/z 907.5 (M+H)⁺.

¹H NMR (400 MHz, CDCl₃): δ 10.90-10.80 (br s, 2H), 7.46-7.44 (m, 2H), 7.35-7.30 (m, 4H), 5.50-5.40 (m, 2H), 5.30-5.20 (m, 2H), 4.45-4.05 (m, 6H), 3.90-3.80 (m, 2H), 3.75 (s, 6H), 3.70-3.60 (m, 2H), 3.02-2.90 (m, 2H), 2.40-1.90 (m, 8H), 1.12-0.81 (m, 18H).

EXAMPLE 8

Synthesis of dimethyl ((2S,2'S)-((2S,2'S)-2,2'-(5,5'-(7,7-dimethyl-7,8-dihydro-6H-dibenzo[f,h][1,5]dioxonine-3,11-diyl)bis(4-ethyl-1H-imidazole-5,2-diyl))bis(pyrrolidine-2,1-diyl))bis(3-methyl-1-oxobutane-2,1-diyl))dicarbamate (Compound 8)

Step 1: (2S,2'S)-di-tert-butyl 2,2'-(5,5'-(7,7-dimethyl-7,8-dihydro-6H-dibenzo[f,h][1,5]dioxonine-3,11-diyl)bis(4-bromo-1H-imidazole-5,2-diyl))bis(pyrrolidine-1-carboxylate) (8a)

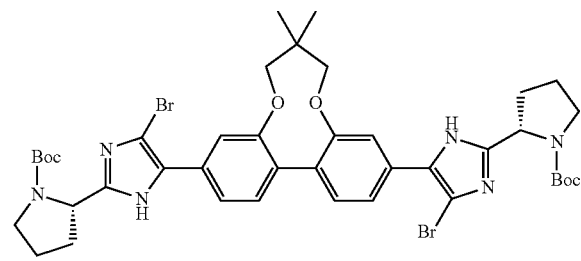 [SMILES: CC1(C)COc2cc(-c3[nH]c([C@@H]4CCCN4C(=O)OC(C)(C)C)nc3Br)ccc2-c2ccc(-c3[nH]c([C@@H]4CCCN4C(=O)OC(C)(C)C)nc3Br)cc2OC1]

To a solution of (2S,2'S)-di-tert-butyl 2,2'-(5,5'-(7,7-dimethyl-7,8-dihydro-6H-dibenzo[f,h][1,5]dioxonine-3,11-diyl)bis(1H-imidazole-5,2-diyl))bis(pyrrolidine-1-carboxylate) (5e) (0.5 g, 0.69 mmol) in THF (40 ml) was added phenyl trimethyl ammonium tribromide (0.65 g, 1.72 mmol) at 0° C. under nitrogen atmosphere. The cooling bath was removed and the reaction mixture was warmed to RT and stirred for 2 h, when the starting material was consumed and a non-polar spot was formed. The reaction mixture was concentrated under reduced pressure and DCM was added to it and the organic contents were washed with water, brine, and dried over sodium sulfate and evaporated under reduced pressure to yield an yellow solid which was used in the next step without purification (0.35 g, 57%). m/z 887.7 (M+H)⁺.

¹H NMR (400 MHz, DMSO-d₆): δ 7.97-7.95 (m, 1H), 7.67-7.58 (m, 3H), 7.56-7.38 (m, 2H), 4.90-4.70 (m, 2H), 4.30-3.90 (m, 4H), 3.50-3.45 (m, 4H), 2.30-1.60 (m, 8H), 1.38-1.20 (m, 18H), 0.89 (s, 6H).

Step 2: Synthesis of (2S,2'S)-di-tert-butyl 2,2'-(5,5'-(7,7-dimethyl-7,8-dihydro-6H-dibenzo[f,h][1,5]dioxonine-3,11-diyl)bis(4-ethyl-1H-imidazole-5,2-diyl))bis(pyrrolidine-1-carboxylate) (8b)

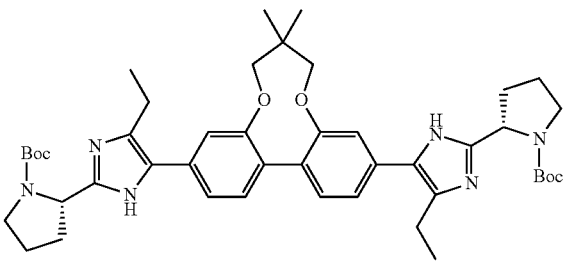 [SMILES: CCc1nc([C@@H]2CCCN2C(=O)OC(C)(C)C)[nH]c1-c1ccc2c(c1)OCC(C)(C)COc1cc(-c3[nH]c([C@@H]4CCCN4C(=O)OC(C)(C)C)nc3CC)ccc1-2]

To a degassed solution of (2S,2'S)-di-tert-butyl 2,2'-(5,5'-(7,7-dimethyl-7,8-dihydro-6H-dibenzo[f,h][1,5]dioxonine-3,11-diyl)bis(4-bromo-1H-imidazole-5,2-diyl))bis(pyrrolidine-1-carboxylate) (8a, 0.25 g, 0.28 mmol) and ethylboronic acid (0.05 g, 0.62 mmol) in a mixture of toluene (10 ml) and water (2 ml) was added potassium phosphate tribasic (0.24 g, 1.13 mmol), tricyclohexylphosphine (6.35 mg, 0.03 mmol) followed by palladium acetate(II) (5.09 mg, 0.03 mmol) and the contents were heated at 110° C. for 45 min in a microwave vial. The reaction was monitored by TLC. The reaction mixture was cooled to RT and water was added and the contents were extracted with EtOAc. The organic layer was washed with brine, dried over sodium sulphate and concentrated under reduced pressure and purified by flash column chromatography (50-60% EtOAc:Hexane) to yield a pale brown solid. m/z 781.5 (M+H)⁺.

Step 3: Synthesis of dimethyl ((2S,2'S)-((2S,2'S)-2,2'-(5,5'-(7,7-dimethyl-7,8-dihydro-6H-dibenzo[f,h][1,5]dioxonine-3,11-diyl)bis(4-ethyl-1H-imidazole-5,2-diyl))bis(pyrrolidine-2,1-diyl))bis(3-methyl-1-oxobutane-2,1-diyl))dicarbamate (Compound 8)

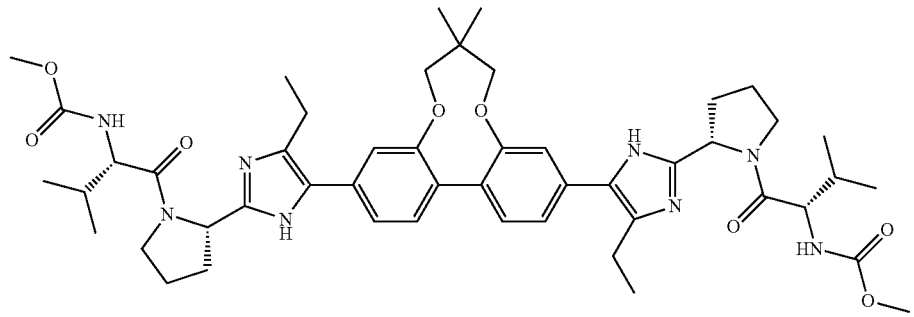

The above compound was synthesized from (2S,2'S)-di-tert-butyl 2,2'-(5,5'-(7,7-dimethyl-7,8-dihydro-6H-dibenzo

[f,h][1,5]dioxonine-3,11-diyl)bis(4-ethyl-1H-imidazole-5,2-diyl))bis(pyrrolidine-1-carboxylate) and (S)-2-((methoxycarbonyl)-amino)-3-methylbutanoic acid by following an analogous procedure described in Step 6, Example 1. m/z 895.5 (M+H)⁺.

¹H NMR (400 MHz, CDCl₃): δ 10.31 (br s, 1H) 10.16 (br s, 1H), 7.41-7.33 (m, 5H), 7.05-7.10 (m, 1H), 5.47-5.44 (m, 2H), 5.30-5.22 (m, 2H), 4.40-4.10 (m, 6H), 3.85-3.81 (m, 2H), 3.71 (s, 6H), 3.65-3.61 (m, 2H), 3.15-3.00 (m, 2H), 2.90-2.80 (m, 2H), 2.40-1.95 (m, 10H), 1.24-0.89 (m, 24H).

EXAMPLE 9

Synthesis of dimethyl ((2S,2'S)-((2S,2'S)-2,2'-(5,5'-(7,7-dimethyl-7,8-dihydro-6H-dibenzo[f,h][1,5]dioxonine-3,11-diyl)bis(4-cyclopropyl-1H-imidazole-5,2-diyl))bis(pyrrolidine-2,1-diyl))bis(3-methyl-1-oxobutane-2,1-diyl))dicarbamate. (Compound 9)

Step 1: (2S,2'S)-di-tert-butyl 2,2'-(5,5'-(7,7-dimethyl-7,8-dihydro-6H-dibenzo[f,h][1,5]dioxonine-3,11-diyl)bis(4-cyclopropyl-1H-imidazole-5,2-diyl))bis(pyrrolidine-1-carboxylate) (9a)

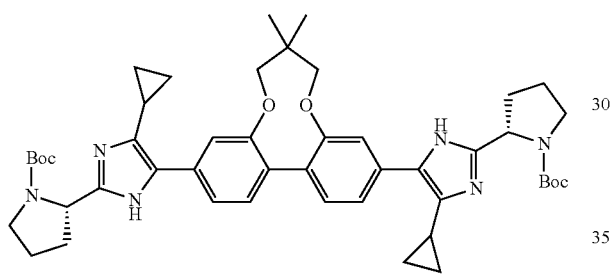

was synthesized from (2S,2'S)-di-tert-butyl 2,2'-(5,5'-(7,7-dimethyl-7,8-dihydro-6H-dibenzo[f,h][1,5]dioxonine-3,11-diyl)bis(4-bromo-1H-imidazole-5,2-diyl))bis(pyrrolidine-1-carboxylate) (8a) and cyclopropyl boronic acid by following an analogous procedure described in Step 2 of Example 8. m/z 805.5 (M+H)⁺.

Step 2: dimethyl ((2S,2'S)-((2S,2'S)-2,2'-(5,5'-(7,7-dimethyl-7,8-dihydro-6H-dibenzo[f,h][1,5]dioxonine-3,11-diyl)bis(4-cyclopropyl-1H-imidazole-5,2-diyl))bis(pyrrolidine-2,1-diyl))bis(3-methyl-1-oxobutane-2,1-diyl))dicarbamate (9b)

was synthesized from (2S,2'S)-di-tert-butyl 2,2'-(5,5'-(7,7-dimethyl-7,8-dihydro-6H-dibenzo[f,h][1,5]dioxonine-3,11-diyl)bis(4-cyclopropyl-1H-imidazole-5,2-diyl))bis(pyrrolidine-1-carboxylate) (9a) and (S)-2-((methoxycarbonyl)-amino)-3-methylbutanoic acid by following an analogous procedure described in Step 6, Example 1. m/z 919.4 (M+H)⁺.

¹H NMR (400 MHz, CDCl₃): δ 10.29 (br s, 1H), 10.00 (br s, 1H), 7.70-7.60 (m, 3H), 7.31-7.27 (m, 3H), 5.43-5.41 (m, 2H), 5.30-5.22 (m, 2H), 4.38-4.13 (m, 6H), 3.85-3.81 (m, 4H), 3.71 (s, 6H), 3.65-3.61 (m, 2H), 3.15-2.95 (m, 4H), 2.40-1.95 (m, 10H), 1.08-0.88 (m, 18H), 0.70-0.55 (m, 4H).

EXAMPLE 10

Synthesis of dimethyl ((2S,2'S)-((2S,2'S)-2,2'-(5,5'-(6',8'-dihydrospiro[cyclopropane-1,7'-dibenzo[f,h][1,5]dioxonine]-3',11'-diyl)bis(1H-imidazole-5,2-diyl))bis(pyrrolidine-2,1-diyl))bis(3-methyl-1-oxobutane-2,1-diyl))dicarbamate (Compound 10)

Step 1: 1,1'-(6',8'-dihydrospiro[cyclopropane-1,7'-dibenzo[f,h][1,5]dioxonine]-3',11'-diyl)diethanone (10a)

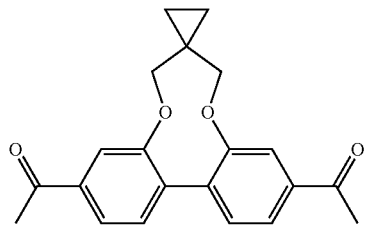

To a stirred suspension of 1.1'-(2,2'-dihydroxy-[1,1'-biphenyl]-4,4'-diyl)-diethanone (0.6 g, 2.22 mmol) (synthesized according to WO 2010/111673), cyclopropane-1,1'-diyldimethanol (0.23 g, 2.22 mmol) (prepared according to WO 2005/30694) and triphenylphosphine (1.7 g, 6.66 mmol) in DCM-toluene-THF (20 mL, 2:1:1) was added DIAD (1.3 g, 6.66 mol) at 0° C. The resulting mixture was stirred at room temperature overnight and partitioned between aqueous and organic layer. The organic layer was washed with water and brine, dried over sodium sulfate and purified by flash column chromatography (30% EtOAc-Hexane) to give the title compound as a white solid (0.28 g, 37%).

¹H NMR (400 MHz, DMSO-d₆): δ 7.75 (d, J=1.6 Hz, 1H), 7.74-7.73 (m, 3H), 7.41 (d, J=7.6 Hz, 2H), 4.29 (s, 2H), 4.17 (s, 2H), 2.65 (s, 6H), 0.59-0.53 (m, 4H).

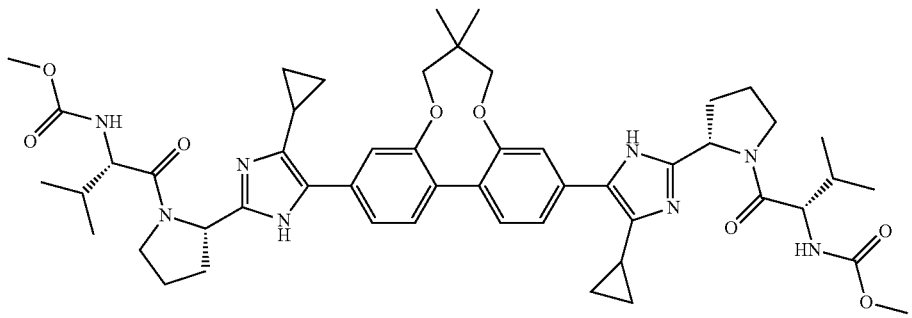

Step 2: 1,1'-(6',8'-dihydrospiro[cyclopropane-1,7'-dibenzo[f,h][1,5]dioxonine]-3',11'-diyl)bis(2-bromoethanone) (10b)

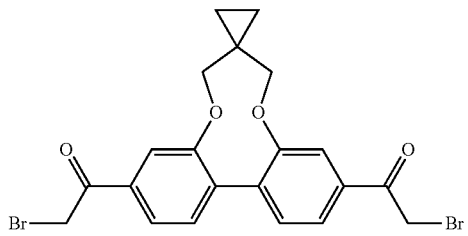 [SMILES: O=C(CBr)c1ccc2c(c1)OCC1(CC1)COc1cc(C(=O)CBr)ccc1-2]

was synthesized from 1,1'-(6',8'-dihydrospiro[cyclopropane-1,7'-dibenzo[f,h][1,5]dioxonine]-3',11'-diyl)diethanone (10a) and bromine by following an analogous procedure described in Step 2, Example 1. m/z 493 (M+H)+.

$^1$H NMR (400 MHz, CDCl$_3$): δ 7.78 (d, J=1.6 Hz, 1H), 7.77-7.53 (m, 3H), 7.44 (d, J=7.6 Hz, 2H), 4.50-4.46 (m, 4H), 4.24-4.20 (m, 4H), 0.60-0.55 (m, 4H).

Step 3: (2S,2'S)-1-di-tert-butyl O'$^2$,O$^2$-((6',8'-dihydro spiro[cyclopropane-1,7'-dibenzo[f,h][1,5]dioxonine]-3',11'-diyl)bis(2-oxoethane-2,1-diyl))bis(pyrrolidine-1,2-dicarboxylate) (10c)

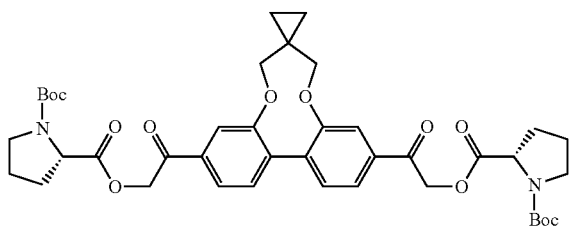

was synthesized from 1,1'-(6',8'-dihydrospiro[cyclopropane-1,7'-dibenzo[f,h][1,5]dioxonine]-3',11'-diyl)bis(2-bromo ethanone) (10b) and (S)-1-(tert-butoxycarbonyl)-pyrrolidine-2-carboxylic acid by following an analogous procedure described in Step 4, Example 1. m/z 663 [(M+H)+–100] (Boc cleavage).

$^1$H NMR (400 MHz, CDCl$_3$): δ 7.68-7.62 (m, 4H), 7.43-7.41 (d, J=7.6 Hz, 2H), 5.63-5.59 (m, 1H), 5.43-5.39 (m, 2H), 5.27-5.23 (m, 1H), 4.53-4.50 (m, 1H), 4.45-4.42 (m, 1H), 4.17-4.11 (m, 4H), 3.64-3.41 (m, 4H), 2.38-2.32 (m, 4H), 2.12-1.93 (m, 4H), 1.49 (s, 18H), 0.59-0.52 (m, 4H).

Step 4: (2S,2'S)-di-tert-butyl 2,2'-(5,5'-(6',8'-dihydrospiro[cyclopropane-1,7'-dibenzo[f,h][1,5]dioxonine]-3',11'-diyl)bis(1H-imidazole-5,2-diyl))bis(pyrrolidine-1-carboxylate) (10d)

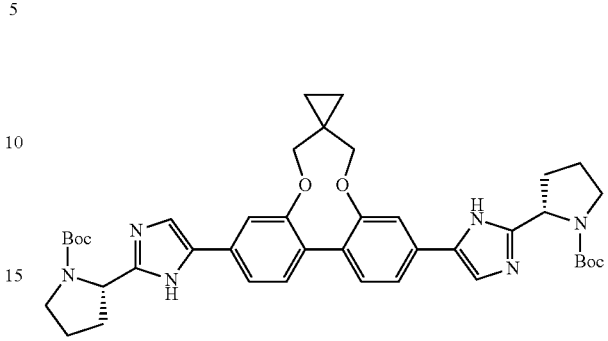

was synthesized from (2S,2'S)-1-di-tert-butyl O'$^2$,O$^2$-((6',8'-dihydrospiro[cyclopropane-1,7'-dibenzo[f,h][1,5]dioxonine]-3',11'-diyl)bis(2-oxoethane-2,1-diyl))bis(pyrrolidine-1,2-dicarboxylate) (10c) by following an analogous procedure described in Step 5, Example 1. m/z 723 (M+H)+.

$^1$H NMR (400 MHz, CDCl$_3$): δ 7.52 (s, 2H), 7.46-7.44 (d, J=8 Hz, 2H), 7.39 (s, 2H), 7.27-7.25 (d, J=8 Hz, 2H), 5.01-4.99 (m, 2H), 4.25 (s, 4H), 3.72-3.68 (m, 2H), 3.55-3.49 (m, 2H), 2.43-2.40 (m, 2H), 2.11-1.95 (m, 6H), 1.49 (s, 6H), 1.27 (s, 12H), 0.58 (s, 4H).

Step 5: dimethyl ((2S,2'S)-((2S,2'S)-2,2'-(5,5'-(6',8'-dihydrospiro[cyclopropane-1,7'-dibenzo[f,h][1,5]dioxonine]-3',11'-diyl)bis(1H-imidazole-5,2-diyl))bis(pyrrolidine-2,1-diyl))bis(3-methyl-1-oxobutane-2,1-diyl))dicarbamate (Compound 10)

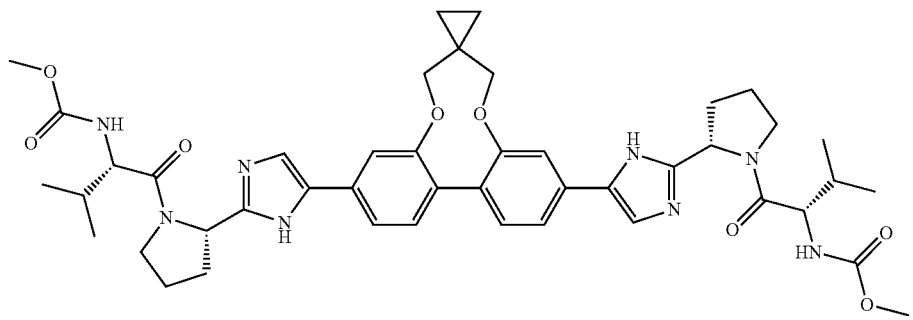

was synthesized from (2S,2'S)-di-tert-butyl 2,2'-(5,5'-(6',8'-dihydrospiro[cyclopropane-1,7'-dibenzo[f,h][1,5]dioxonine]-3',11'-diyl)bis(1H-imidazole-5,2-diyl))bis(pyrrolidine-1-carboxylate) (10d) and (S)-2-((methoxycarbonyl)-amino)-3-methylbutanoic acid by following an analogous procedure described in Step 6, Example 1. m/z 837 (M+H)+.

$^1$H NMR (400 MHz, CD$_3$OD): δ 7.49-7.25 (m, 8H), 5.18-5.16 (m, 2H), 4.25-4.23 (m, 4H), 4.11-3.99 (m, 2H), 3.91-3.85 (m, 2H), 3.66 (s, 6H), 3.31-3.23 (m, 2H), 2.38-1.95 (m, 10H), 1.05-0.91 (m, 12H), 0.57 (s, 4H).

EXAMPLE 11

Synthesis of dimethyl ((2S,2'S)-((2S,2'S)-2,2'-(5,5'-(6,11-dihydrotribenzo[b,d,h][1,6]dioxecine-3,14-diyl)bis(1H-imidazole-5,2-diyl))bis(pyrrolidine-2,1-diyl))bis(3-methyl-1-oxobutane-2,1-diyl)) dicarbamate (Compound 11)

Step 1: 1,1'-(6,11-dihydrotribenzo[b,d,h][1,6]dioxecine-3,14-diyl)diethanone (11a)

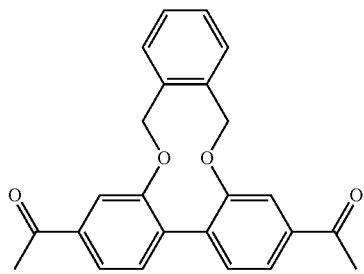 [SMILES: CC(=O)c1ccc2c(c1)OCc1ccccc1COc1cc(C(C)=O)ccc1-2]

was synthesized from 1,1'-(2,2'-dihydroxy-[1,1'-biphenyl]-4,4'-diyl)-diethanone and 1,2-bis(bromomethyl)benzene by following an analogous procedure described in Step 1, Example 1. m/z 373.2 (M+H)⁺.

¹H NMR (400 MHz, DMSO-d₆): δ 7.80 (s, 2H), 7.66 (dd, J=8 Hz, 1.6 Hz, 2H), 7.56-7.54 (m, 2H), 7.42 (d, J=8 Hz, 2H), 7.38-7.35 (m, 2H), 5.48-5.46 (m, 2H), 5.35-5.31 (m, 2H), 2.61 (s, 6H).

Step 2: 1,1'-(6,11-dihydrotribenzo[b,d,h][1,6]dioxecine-3,14-diyl)bis(2-bromoethanone) (11b)

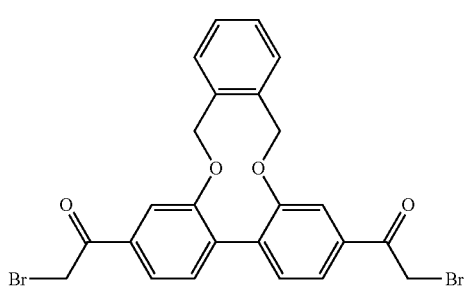 [SMILES: O=C(CBr)c1ccc2c(c1)OCc1ccccc1COc1cc(C(=O)CBr)ccc1-2]

was synthesized from 1,1'-(6,11-dihydrotribenzo[b,d,h][1,6]dioxecine-3,14-diyl)diethanone (11a) and bromine by following an analogous procedure described in Step 2, Example 1. m/z 530.9 (M+H)⁺.

¹H NMR (400 MHz, CDCl₃): δ 7.82 (d, J=1.6 Hz, 2H), 7.71-7.68 (m, 2H), 7.50-7.48 (m, 2H), 7.43-7.27 (m, 4H), 5.47-5.43 (m, 2H), 7.31-7.28 (m, 2H), 4.52-4.42 (m, 4H).

Step 3: (2S,2'S)-1-di-tert-butyl O'²,O²-((6,11-dihydrotribenzo[b,d,h][1,6]dioxecine-3,14-diyl)bis(2-oxoethane-2,1-diyl)) bis(pyrrolidine-1,2-dicarboxylate) (11c)

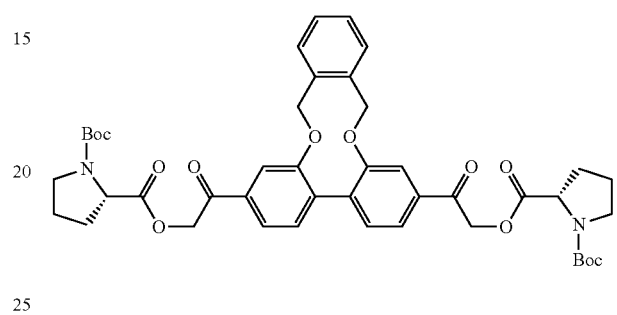

was synthesized from 1,1'-(6,11-dihydrotribenzo[b,d,h][1,6]dioxecine-3,14-diyl)bis(2-bromoethanone) (11b) and (S)-1-(tert-butoxycarbonyl)-pyrrolidine-2-carboxylic acid by following an analogous procedure described in Step 4, Example 1.

Step 4: Synthesis of (2S,2'S)-di-tert-butyl 2,2'-(5,5'-(6,11-dihydrotribenzo[b,d,h][1,6]dioxecine-3,14-diyl)bis(1H-imidazole-5,2-diyl))bis(pyrrolidine-1-carboxylate) (11d)

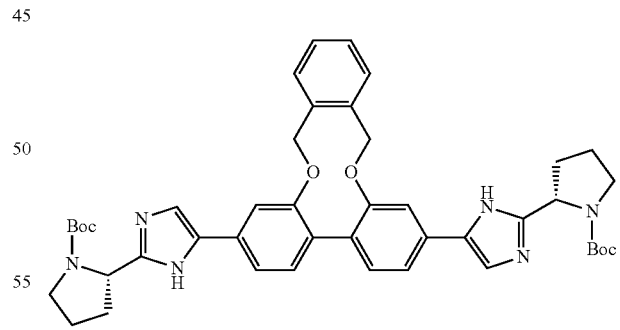

was synthesized from (2S,2'S)-1-di-tert-butyl O'²,O²-((6,11-dihydrotribenzo[b,d,h][1,6]dioxecine-3,14-diyl)bis(2-oxoethane-2,1-diyl)) bis(pyrrolidine-1,2-dicarboxylate) (11c) by following an analogous procedure described in Step 5, Example 1. m/z 759.5 (M+H)⁺.

Step 5: Synthesis of dimethyl ((2S,2'S)-((2S,2'S)-2,2'-(5,5'-(6,11-dihydrotribenzo[b,d,h][1,6]dioxecine-3,14-diyl)bis(1H-imidazole-5,2-diyl))bis(pyrrolidine-2,1-diyl))bis(3-methyl-1-oxobutane-2,1-diyl))dicarbamate (Compound 11)

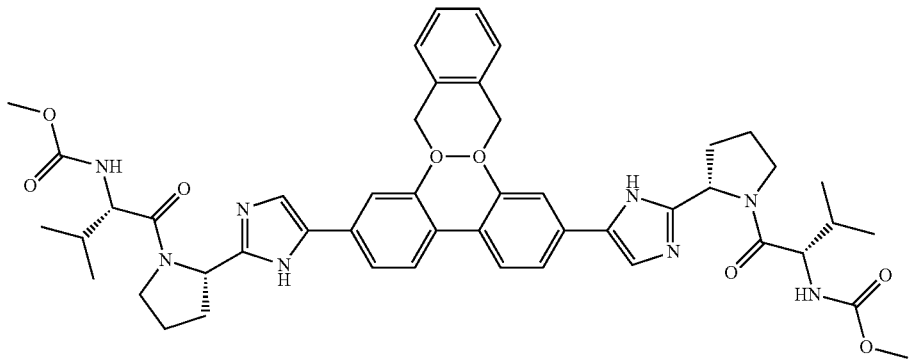

The above compound was synthesized from (2S,2'S)-di-tert-butyl 2,2'-(5,5'-(6,11-dihydrotribenzo[b,d,h][1,6]dioxecine-3,14-diyl)bis(1H-imidazole-5,2-diyl))bis(pyrrolidine-1-carboxylate) and (S)-2-((methoxycarbonyl)-amino)-3-methylbutanoic acid by following an analogous procedure described in Step 6, Example 1. m/z 873.5 (M+H)$^+$.

EXAMPLE 12

Biological Activity

Anti-viral activity of the compounds of the invention was monitored using an HCV replicon assay. The Huh7.5/Con1/SG-Neo(I)hRluc2aUb cell line persistently expressing a bicistronic genotype 1b replicon in Huh 7.5 cells and the Huh7.5/J6/JFH1/EMCVIRES/hRlucNeo cell line expressing a bicistronic genotype 2a replicon in Huh 7.5 cells were obtained from Apath LLC. These cell lines were used to test inhibition of replicon levels by test compound using *Renilla* luciferase enzyme activity readout as a measure of viral replication efficiency.

Briefly, 7000-7500 cells were seeded in 96 well black clear bottom plates and allowed to adhere overnight. The next day each compound was added in triplicate to the cells at the desired concentration with a final DMSO concentration of 0.5%. Cells in media alone and cells incubated without drug with 0.5% DMSO served as controls. The plates were incubated for 72 h at 37° C. prior to running the luciferase assay. Enzyme activity was measured using *Renilla-Glo* Luciferase Assay kit from Promega as per the manufacturer's instructions. The following equation was used to generate the percent inhibition value for each test concentration.

$$\% \text{ Inhibition} = \frac{\text{Average Control (cells alone} + 0.5\% \ DMSO) - \text{Average compound value(cells} + \text{drug)}}{\text{Average Control (cells alone} + 0.5\% \ DMSO)} \times 100$$

The IC$_{50}$ value was determined using GraphPad Prism and the following equation:

$$Y=\text{Bottom}+(\text{Top}-\text{Bottom})/(1+10\hat{\ }((\text{LogIC}_{50}-X)*\text{Hill slope}))$$

IC$_{50}$ values/% inhibitions of compounds were determined 2-3 times in the replicon assays.

Compounds of the present invention exhibited IC$_{50}$ values in the range of 1 pM to 100 nM for inhibition of genotype 1b and 2a replicon of HCV, some of the representative results are provided below in table 1

TABLE 1

| Compound | Gt1b IC$_{50}$ | Gt2a IC$_{50}$ |
|---|---|---|
| Compound 2 | 51 pM | 53 pM |
| Compound 3 | 18 pM | 37 pM |
| Compound 6 | 21 pM | 671 pM |
| Compound 7 | 4 pM | 249 pM |

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A compound of formula (I), a tautomeric form, a stereoisomer, or a pharmaceutically acceptable salt thereof,

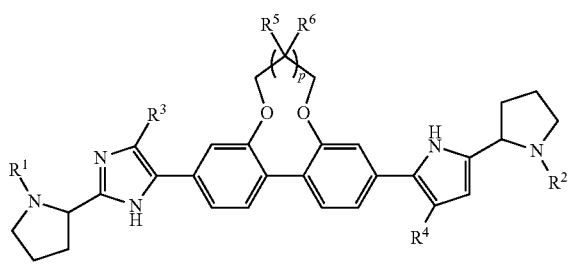

(I)

wherein, $R^1$ and $R^2$ are each independently selected from hydrogen, substituted- or unsubstituted-alkyl, substituted- or unsubstituted-cycloalkyl, substituted- or unsubstituted-aryl, substituted- or unsubstituted-heteroaryl, substituted- or unsubstituted-heterocyclyl, $R^{7a}C(=O)—$, $R^{7a}S(=O)_2—$, $R^{7a}OC(=O)—$, $(R^8)R^7NC(=O)—$, $R^{7a}OC(=O)N(R^8)CR^b(R^a)C(=O)—$, $R^{7a}OC(=O)N(R^8)CR^b(R^a)C(R^d)(R^c)C(=O)—$, $R^{7a}C(=O)N(R^8)C(R^b)(R^a)C(=O)—$, $R^{7a}C(=O)N(R^8)CR^b(R^a)C(R^d)(R^c)C(=O)—$, $(R^8)R^7NC(=O)N(R^9)C(R^b)(R^a)C(=O)—$, and $R^8(R^7)NC(=O)N(R^9)CR^b(R^a)C(R^d)(R^c)C(=O)—$;

$R^3$ and $R^4$ are each independently selected from hydrogen, halogen, substituted- or unsubstituted-alkyl, and substituted- or unsubstituted-cycloalkyl;

$R^5$ and $R^6$ are independently selected form hydrogen and substituted- or unsubstituted-alkyl; or $R^5$ and $R^6$ are groups, which together with the carbon atom to which they are attached form a substituted- or unsubstituted-3 to 6 membered carbocycie or a substituted- or unsubstituted-5 to 6 membered heterocycle; or $R^5$ and $R^6$ are groups, wherein two $R^5$ groups attached to two different carbon atoms, two $R^6$ groups attached to two different carbon atoms, or an $R^5$ group attached to one carbon atom and an $R^6$ group attached to a different carbon atom, together with the carbon atoms to which they are attached form a substituted- or unsubstituted-3 to 6 membered carbocycle or a substituted- or unsubstituted-5 to 6 membered heterocycle;

$R^7$ is selected from hydrogen, substituted- or unsubstituted-alkyl, substituted- or unsubstituted-cycloalkyl, substituted- or unsubstituted-aryl, substituted- or unsubstituted-heteroary, and substituted- or unsubstituted-heterocyclyl;

$R^8$ and $R^9$ are each independently selected from hydrogen and substituted- or unsubstituted-alkyl;

$R^{7a}$ is independently selected from substituted- or unsubstituted-alkyl, substituted- or unsubstituted-cycloalkyl, substituted- or unsubstituted-aryl, substituted- or unsubstituted-heteroaryl, and substituted- or unsubstituted-heterocyclyl;

$R^a$, $R^b$, $R^c$ and $R^d$ are independently selected from hydrogen, substituted- or unsubstituted-$C_{1-6}$ alkyl, substituted- or unsubstituted-aryl, substituted- or unsubstituted-heteroaryl, substituted- or unsubstituted-cycloalkyl, and substituted- or unsubstituted-heterocyclyl, or $R^a$, $R^b$, $R^c$ and $R^d$ together with the carbon atom(s) to which they are attached forming substituted- or unsubstituted-carbocycle, substituted- or unsubstituted-heterocycle;

p is an integer selected from 1, 2, and 3;

when the alkyl group is a substituted alkyl group, the alkyl is substituted with 1 to 4 substituents selected independently from oxo, halogen, cyano, perhaloalkyl, cycloalkyl, aryl, heteroaryl, heterocyclyl, $R^{10a}O—$, $(alkyl)S(=O)_2—$, $(alkyl)C(=O)—$, $(alkyl)OC(=O)—$, $(alkyl)C(=O)O—$, $R^{10}N(H)C(=O)—$, $R^{10}(alkyl)NC(=O)—$, $(alkyl)C(=O)N(H)—$, $R^{10}N(H)—$, $R^{10}(alkyl)N—$, $R^{10}(H)NC(=O)N(H)—$, and $R^{10}(alkyl)NC(=O)N(H)—$;

when the 'cycloalkyl' and the carbocyclic groups are substituted, each of them is substituted with 1 to 3 substituents selected independently from oxo, halogen, cyano, $C_{1-6}$ alkyl, perhaloalkyl, $R^{10a}O—$, $(alkyl)S(=O)_2—$, $(alkyl)C(=O)—$, $(alkyl)OC(=O)—$, $(alkyl)C(=O)O—$, $R^{10}(H)NC(=O)—$, $R^{10}(alkyl)NC(=O)—$, $(alkyl)C(=O)N(H)—$, $R^{10}(H)N—$, $R^{10}(alkyl)N—$, $R^{10}(H)NC(=O)N(H)—$, and $R^{10}(alkyl)NC(=O)N(H)—$;

when the aryl group is substituted, it is substituted with 1 to 3 substituents selected independently from halogen, cyano, hydroxy, $C_{1-6}$ alkyl, perhaloalkyl, alkyl-O—, perhaloalkyl-O—, alkyl(alkyl)N—, alkyl(H)N—, $H_2N—$, alkyl-S(=O)$_2$—, alkyl-C(=O)(alkyl)N—, alkyl-C(=O)N(H)—, alkyl(alkyl)NC(=O)—, alkyl(H)NC(=O)—, $H_2NC(=O)—$, alkyl(alkyl)NS(=O)$_2$—, alkyl(H)NS(=O)$_2$—, and $H_2NS(=O)_2—$;

when the heteroaryl group is substituted, it is substituted with 1 to 3 substituents selected independently from halogen, cyano, hydroxy, $C_{1-6}$ alkyl, perhaloalkyl, alkyl-O—, perhaloalkyl-O—, alkyl(alkyl)N—, alkyl(H)N—, $H_2N—$, alkyl-S(=O)$_2$—, alkyl-C(=O)(alkyl)N—, alkyl-C(=O)N(H)—, alkyl(alkyl)NC(=O)—, alkyl(H)NC(=O)—, $H_2NC(=O)—$, alkyl(alkyl)NS(=O)$_2$—, alkyl(H)NS(=O)$_2$—, and $H_2NS(=O)_2—$;

when the heterocyclic group is substituted, it can be substituted either on a ring carbon atom or a ring heteroatom; when it is substituted on a ring carbon atom, it is substituted with 1-3 substituents selected independently from halogen, cyano, oxo, $C_{1-6}$ alkyl, perhaloalkyl, $R^{10a}O—$, (alkyl)OC(=O)—, (alkyl)C(=O)O—, $R^{10}(H)NC(=O)—$, $R^{10}(alkyl)NC(=O)—$, (alkyl)C(=O)N(H)—, $R^{10}(H)N—$, $R^{10}(alkyl)N—$, $R^{10}(H)NC(=O)N(H)—$, and $R^{10}(alkyl)NC(=O)N(H)—$;

when the 'heterocyclic' group is substituted on a ring heteroatom, it is substituted with 1 or more substituents selected from $C_{1-6}$ alkyl, (alkyl)SO$_2$—, (alkyl)C(=O)—, (alkyl)OC(=O)—, $R^{10}(H)NC(=O)—$, and $R^{10}(alkyl)NC(=O)—$;

$R^{10}$ is selected from hydrogen, alkyl, cycloalkyl, aryl, heteroaryl, and heterocyclyl; and $R^{10a}$ is selected from hydrogen, alkyl, perhaloalkyl, cycloalkyl, aryl, heteroaryl, and heterocyclyl.

2. The compound of formula (I), its tautomeric form, its stereoisomer, or its pharmaceutically acceptable salt, as claimed in claim 1, wherein compound of formula I is selected from

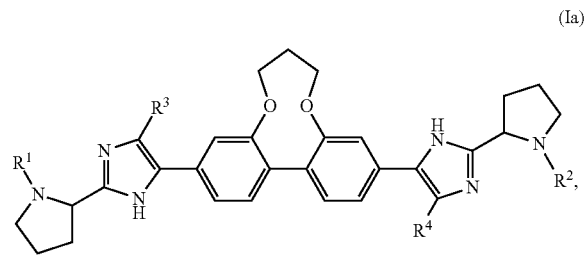
(Ia)

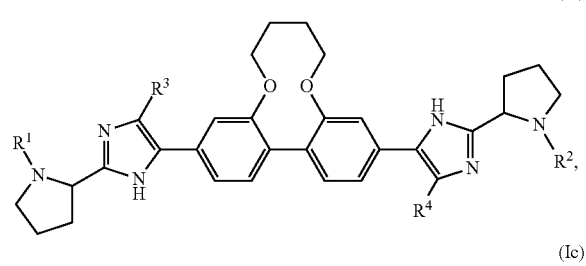
(Ib)

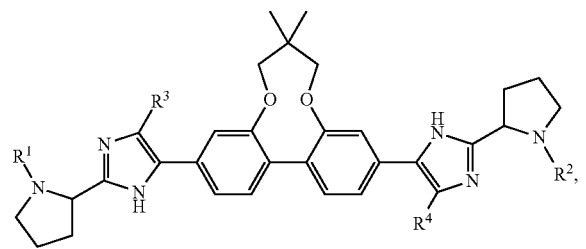
(Ic)

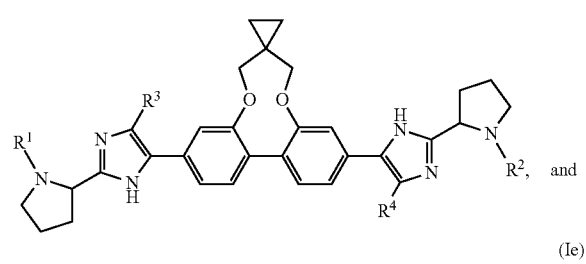
(Id)

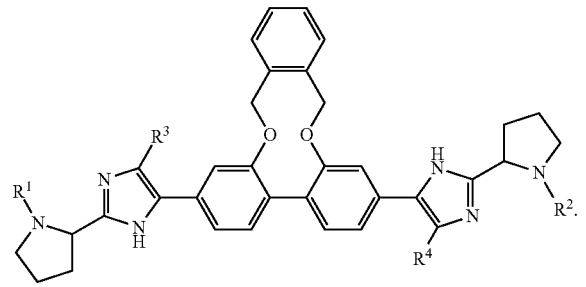
(Ie)

3. The compound of formula (I), its tautomeric form, its stereoisomer, or its pharmaceutically acceptable salt, as claimed in claim 1, wherein $R^1$ and $R^2$ are selected from $R^{7a}C(=O)-$, $R^{7a}S(=O)_2-$, $R^{7a}OC(=O)-$, $(R^8)R^7NC(=O)-$, $R^{7a}OC(=O)N(R^8)CR^b(R^a)C(=O)-$, $R^{7a}OC(=O)N(R^8)CR^b(R^a)C(R^d)(R^c)C(=O)-$, $R^{7a}C(=O)N(R^8)C(R^b)(R^a)C(=O)-$, $R^{7a}C(=O)N(R^8)CR^b(R^a)C(R^d)(R^c)C(=O)-$, $(R^8)R^7NC(=O)N(R^9)C(R^b)(R^a)C(=O)-$, and $R^8(R^7)NC(=O)N(R^9)CR^b(R^a)C(R^d)(R^c)C(=O)-$.

4. The compound of formula (I), its tautomeric form, its stereoisomer, or its pharmaceutically acceptable salt, as claimed in claim 1, wherein $R^1$ and $R^2$ are selected from $R^{7a}OC(=O)N(R^8)CR^b(R^a)C(=O)-$, $R^{7a}OC(=O)N(R^8)CR^b(R^a)C(R^d)(R^c)C(=O)-$, $R^{7a}C(=O)N(R^8)C(R^b)(R^a)C(=O)-$, $R^{7a}C(=O)N(R^8)CR^b(R^a)C(R^d)(R^c)C(=O)-$, $(R^8)R^7NC(=O)N(R^9)C(R^b)(R^a)C(=O)-$, and $R^8(R^7)NC(=O)N(R^9)CR^b(R^a)C(R^d)(R^c)C(=O)-$.

5. The compound of formula (I), its tautomeric form, its stereoisomer or its pharmaceutically acceptable salt, as claimed in claim 1, wherein $R^1$ and $R^2$ both are $R^{7a}OC(=O)N(R^8)CR^b(R^a)C(=O)-$.

6. The compound of formula (I), its tautomeric form, its stereoisomer, or its pharmaceutically acceptable salt, as claimed in claim 1, wherein $R^3$ and $R^4$ are selected independently from hydrogen, chloro, ethyl, and cyclopropyl.

7. The compound of formula (I), its tautomeric form, its stereoisomer, or its pharmaceutically acceptable salt, as claimed in claim 1, wherein the compound is selected from
  dimethyl ((2S,2'S)-((2S,2'S)-2,2'-(5,5'-(7,8-dihydro-6H-dibenzo[f,h][1,5]dioxonine-3,11-diyl)bis(1H-imidazole-5,2-diyl))bis(pyrrolidine-2,1-diyl))bis(3-methyl-1-oxobutane-2,1-diyl))dicarbamate;
  methyl ((S)-1-((S)-2-(5-(11-(2-((S)-1-((S)-2-(methoxycarbonyl)amino-3-methylbutanoyl)pyrrolidin-2-yl)-1H-imidazol-5-yl)-7,8-dihydro-6H-dibenzo[f,h][1,5]dioxonin-3-yl)-4-chloro-1H-imidazol-2-yl)pyrrolidin-1-yl)-3-methyl-1-oxobutan-2-yl)carbamate;
  dimethyl ((2S,2'S)-((2S,2'S)-2,2'-(5,5'-(7,8-dihydro-6H-dibenzo[f,h][1,5]dioxonine-3,11-diyl)bis(4-chloro-1H-imidazole-5,2-diyl))bis(pyrrolidine-2,1-diyl))bis(3-methyl-1-oxobutane-2,1-diyl))dicarbamate;
  dimethyl ((2S,2'S)-((2S,2'S)-2,2'-(5,5'-(6,7,8,9-tetrahydrodibenzo[b,d][1,6]dioxecine-3,12-diyl)bis(1H-imidazole-5,2-diyl))bis(pyrrolidine-2,1-diyl))bis(3-methyl-1-oxobutane-2,1-diyl))dicarbamate;
  dimethyl ((2S,2'S)-((2S,2'S)-2,2'-(5,5'-(7,7-dimethyl-7,8-dihydro-6H-dibenzo[f,h][1,5]dioxonine-3,11-diyl)bis(1H-imidazole-5,2-diyl))bis(pyrrolidine-2,1-diyl))bis(3-methyl-1-oxobutane-2,1-diyl))dicarbamate;
  methyl ((S)-1-((S)-2-(5-(11-(2-((S)-1-((S)-2-(methoxycarbonyl)amino-3-methylbutanoyl)pyrrolidin-2-yl)-4-chloro-1H-imidazol-5-yl)-7,7-dimethyl-7,8-dihydro-6H-dibenzo[f,h][1,5]dioxonin-3-yl)-1H-imidazol-2-yl)pyrrolidin-1-yl)-3-methyl-1-oxobutan-2-yl)carbamate;
  dimethyl ((2S,2'S)-((2S,2'S)-2,2'-(5,5'-(7,7-dimethyl-7,8-dihydro-6H-dibenzo[f,h][1,5]dioxonine-3,11-diyl)bis(4-chloro-1H-imidazole-5,2-diyl))bis(pyrrolidine-2,1-diyl))bis(3-methyl-1-oxobutane-2,1-diyl))dicarbamate;
  dimethyl ((2S,2'S)-((2S,2'S)-2,2'-(5,5'-(7,7-dimethyl-7,8-dihydro-6H-dibenzo[f,h][1,5]dioxonine-3,11-diyl)bis(4-ethyl-1H-imidazole-5,2-diyl))bis(pyrrolidine-2,1-diyl))bis(3-methyl-1-oxobutane-2,1-diyl))dicarbamate;
  dimethyl ((2S,2'S)-((2S,2'S)-2,2'-(5,5'-(7,7-dimethyl-7,8-dihydro-6H-dibenzo[f,h][1,5]dioxonine-3,11-diyl)bis(4-cyclopropyl-1H-imidazole-5,2-diyl))bis(pyrrolidine-2,1-diyl))bis(3-methyl-1-oxobutane-2,1-diyl))dicarbamate;
  dimethyl ((2S,2'S)-((2S,2'S)-2,2'-(5,5'-(6',8'-dihydrospiro[cyclopropane-1,7'-dibenzo[f,h][1,5]dioxonine]-3',11'-diyl)bis(1H-imidazole-5,2-diyl))bis(pyrrolidine-2,1-diyl))bis(3-methyl-1-oxobutane-2,1-diyl))dicarbamate; and
  dimethyl ((2S,2'S)-((2S,2'S)-2,2'-(5,5'-(6,11-dihydrotribenzo[b,d,h][1,6]dioxecine-3,14-diyl)bis(1H-imidazole-5,2-diyl))bis(pyrrolidine-2,1-diyl))bis(3-methyl-1-oxobutane-2,1-diyl))dicarbamate.

8. A pharmaceutical composition comprising a compound or a combination of compounds according to claim 1, a tautomeric form, a stereoisomer, or a pharmaceutically acceptable salt thereof, in combination with a pharmaceutically acceptable carrier or excipient.

9. A method of inhibiting the replication of an RNA-containing virus comprising contacting said virus with a therapeutically effective amount of a compound or combination of compounds of claim 1, a tautomeric form, a stereoisomer or a pharmaceutically acceptable salt thereof.

10. A method of treating or preventing infection caused by an RNA-containing virus comprising administering to a patient in need of such treatment or prevention a therapeutically effective amount of a compound or combination of compounds of claim 1, a tautomeric form, a stereoisomer or a pharmaceutically acceptable salt thereof.

11. The method of claim 10, wherein the RNA-containing virus is hepatitis C virus.

12. The method of claim 10, further comprising the step of co-administering one or more agents selected from a host immune modulator and an antiviral agent, or a combination thereof.

13. The method of claim 12, wherein the host immune modulator is selected from interferon-alpha, pegylated-interferon-alpha, interferon-beta, interferon-gamma, consensus interferon, a cytokine, and a vaccine.

14. The method of claim 12, wherein the antiviral agent inhibits replication of HCV by inhibiting a host cellular function associated with viral replication.

15. The method of claim 12, wherein the antiviral agent inhibits the replication of HCV by targeting a protein of the viral genome.

16. The method of claim 12, wherein said antiviral agent is an inhibitor of a HCV viral protein, a replication process or a combination thereof, wherein said targeting protein or replication process is selected from helicase, protease, polymerase, metalloprotease, NS4A, NS4B, NS5A, assembly, entry, and IRES.

17. The method of claim 12, further comprising the step of co-administering an agent or combination of agents that treat or alleviate symptoms of HCV infection selected from cirrhosis and inflammation of the liver.

18. The method of claim 12, further comprising the step of co-administering one or more agents that treat patients for disease caused by hepatitis B (HBV) infection.

19. The method of claim 12, further comprising the step of co-administering one or more agents that treat patients for disease caused by human immunodeficiency virus (HIV) infection.

20. The pharmaceutical composition of claim 8, further comprising an agent selected from interferon, pegylated interferon, ribavirin, amantadine, an HCV protease inhibitor, an HCV polymerase inhibitor, an HCV helicase inhibitor, or an internal ribosome entry site inhibitor.

21. The composition of claim 8, further comprising a cytochrome P450 monooxygenase inhibitor or a pharmaceutically acceptable salt thereof.

22. A method of treating hepatitis C infection in a subject in need thereof comprising co-administering to said subject a cytochrome P450 monooxygenase inhibitor or a pharmaceutically acceptable salt thereof, and a compound of claim 1, a tautomeric form, a stereoisomer, or a pharmaceutically acceptable salt thereof.

* * * * *